(12) United States Patent
Ward et al.

(10) Patent No.: US 8,048,918 B2
(45) Date of Patent: Nov. 1, 2011

(54) TREATMENT OF HYPERPROLIFERATIVE DISEASES

(75) Inventors: Simon Ward, Sheffield (GB); Claes Bavik, Sheffield (GB); Michael Cork, Sheffield (GB); Rachid Tazi-Aahnini, Sheffield (GB)

(73) Assignee: Vampex Limited, Manchester (GB)

( * ) Notice: Subject to any disclaimer, the term of this patent is extended or adjusted under 35 U.S.C. 154(b) by 385 days.

(21) Appl. No.: 10/085,239

(22) Filed: Feb. 27, 2002

(65) Prior Publication Data

US 2003/0119715 A1 Jun. 26, 2003

Related U.S. Application Data

(63) Continuation-in-part of application No. PCT/GB01/03694, filed on Aug. 17, 2001.

(30) Foreign Application Priority Data

Aug. 17, 2000 (GB) .................................. 0020351.3

(51) Int. Cl.
- *A01N 37/02* (2006.01)
- *A01N 37/10* (2006.01)
- *A61K 31/22* (2006.01)
- *A61K 31/19* (2006.01)

(52) U.S. Cl. ........................................ 514/546; 514/569

(58) Field of Classification Search ................... 514/476, 514/406, 504, 703
See application file for complete search history.

(56) References Cited

U.S. PATENT DOCUMENTS

| | | | | |
|---|---|---|---|---|
| 4,870,101 A | * | 9/1989 | Ku et al. ........................ | 514/476 |
| 5,438,073 A | * | 8/1995 | Saurat et al. .................... | 514/452 |
| 5,858,750 A | * | 1/1999 | Bandman et al. ............. | 435/190 |
| 5,917,082 A | * | 6/1999 | Vuligonda et al. ............ | 560/100 |

FOREIGN PATENT DOCUMENTS

| | | |
|---|---|---|
| EP | 0284879 A2 | 10/1988 |
| EP | 0610511 | 8/1994 |
| GB | 2023001 A * | 12/1979 |
| WO | WO 97/15298 | 5/1999 |
| WO | WO 01/30383 | 5/2001 |
| WO | WO 02/002074 | 1/2002 |
| WO | WO 02/072084 | 9/2002 |

OTHER PUBLICATIONS

Napoli JL. "Retinol Metabolism in LLC-PK1 Cells. Characterization of Retinoic Acid Synthesis by an Established Mammalian Cell Line." Journal of Biological Chemistry, 1986;261(29):13592-13597.*
"Glucocorticoid". Stedman's Medical Dictionary (Twenty-Second Edition). The Williams and Wilkins Company, 1972. p. 527.*
Ghosh et al. "Mechanism of Inhibition of 3alpha,20beta-hydroxysteroid Dehydrogenase by a Licorice-Derived Steroidal Inhibitor". Structure, Oct. 15, 1994; 2(10):973-980.*
Kelloff et al. "Chemopreventive Drug Development: Perspectives and Progress". Cancer Epidemiology, Biomarkers and Prevention. 3, 1994:85-98.*
Bavik, Claes et al., "Retinol-Binding Protein Mediates Uptake of Retinol to Cultured Human Keratinocytes", *Exp. Cell Res.*, vol. 216, pp. 358-62 (1996).
Melhus, Hakan et al., "Epitope Mapping of a Monoclonal Antibody that Blocks the Binding of Retinol-Binding Protein to its Receptor", *Biochem. Biophys. Res. Comm.*, vol. 210, pp. 105-112 (1995).
Connor, M.J. "Modulation of Tumor Promotion in Mouse Skin by the Food Additive Citral (3,7-dimethyl-2,6-octadienal)", *Cancer Lett.*, vol. 56, pp. 25-28 (1991).
Estrov, Zeev et al., "Neoplasia: Phenylarsine Oxide Blocks Interleukin-1β-Induced Activation of the Nuclear Transcription Factor NF-kB, Inhibits Proliferation and Induces Apoptosis of Acute Myelogenous Leukemia Cells", *Blood*, pp. 2844-2853 (1999).

* cited by examiner

*Primary Examiner* — Leslie A Royds Draper
(74) *Attorney, Agent, or Firm* — Mintz Levin Cohn Ferris Glovsky and Popeo, P.C.

(57) ABSTRACT

We describe methods and compositions for treating a patient suffering from a hyperproliferative disorder or photoageing. Our methods involve blocking the activity of a retinol binding protein receptor (RBPr) in cells of the patient, and/or administering to the patient an antagonist of a retinol binding protein receptor (RBPr) and/or lowering the endogenous level of retinoic acid (RA) in cells of said patient.

8 Claims, 11 Drawing Sheets

RoH normal skin

RBPr normal skin

RoH psoriatic skin

RBPr psoriatic skin

KGM  
Ca2+

KGM  
Ca2+  
P142  
RBP

KGM  
Ca2+  
RBP

| KGM | KGM | KGM | KGM |
| Ca2+ | Ca2+ | Ca2+ | Ca2+ |
|  | RBP | RBP | RBP |
|  |  | Peptide 589 | Peptide 592 |

| KGM | KGM | KGM | KGM |
| Ca2+ | Ca2+ | Ca2+ | Ca2+ |
|  | ROL | ROL | ROL |
|  |  | Disulfiram | Citral |

SEQUENCE LISTING

```
<160> NUMBER OF SEQ ID NOS: 23

<210> SEQ ID NO 1
<211> LENGTH: 17
<212> TYPE: DNA
<213> ORGANISM: Artificial Sequence
<220> FEATURE:
<223> OTHER INFORMATION: Example of retinoic response element found in
      humans and/or mice
<220> FEATURE:
<221> NAME/KEY: misc_feature
<222> LOCATION: (7)..(7)
<223> OTHER INFORMATION: "n" can be a,t,g, or c
<220> FEATURE:
<221> NAME/KEY: misc_feature
<222> LOCATION: (8)..(8)
<223> OTHER INFORMATION: "n" can be a,t,g, or c
<220> FEATURE:
<221> NAME/KEY: misc_feature
<222> LOCATION: (9)..(9)
<223> OTHER INFORMATION: "n" can be a,t,g, or c
<220> FEATURE:
<221> NAME/KEY: misc_feature
<222> LOCATION: (10)..(10)
<223> OTHER INFORMATION: "n" can be a,t,g or c
<220> FEATURE:
<221> NAME/KEY: misc_feature
<222> LOCATION: (11)..(11)
```

<223> OTHER INFORMATION: "n" can be a,t,g, or c

<400> SEQUENCE: 1
aggtcannnn naggtca					17

<210> SEQ ID NO 2
<211> LENGTH: 14
<212> TYPE: DNA
<213> ORGANISM: Unknown
<220> FEATURE:
<223> OTHER INFORMATION: Example of DR-2 retinoic response element found
      in humans and/or mice
<220> FEATURE:
<221> NAME/KEY: misc_feature
<222> LOCATION: (7)..(7)
<223> OTHER INFORMATION: "n" can be a,t,g, or c
<220> FEATURE:
<221> NAME/KEY: misc_feature
<222> LOCATION: (8)..(8)
<223> OTHER INFORMATION: "n" can be a,t,g, or c

<400> SEQUENCE: 2
aggtcannag gtca					14

<210> SEQ ID NO 3
<211> LENGTH: 15
<212> TYPE: DNA
<213> ORGANISM: Unknown
<220> FEATURE:
<223> OTHER INFORMATION: example of consensus vitamin D response element
      found in humans and/or mice
<220> FEATURE:
<221> NAME/KEY: misc_feature
<222> LOCATION: (7)..(7)
<223> OTHER INFORMATION: "n" can be a,t,g or c
<220> FEATURE:
<221> NAME/KEY: misc_feature
<222> LOCATION: (8)..(8)
<223> OTHER INFORMATION: "n" can be a,t,g or c

<400> SEQUENCE: 3
gggtganngg gggca					15

<210> SEQ ID NO 4
<211> LENGTH: 15
<212> TYPE: DNA
<213> ORGANISM: Unknown
<220> FEATURE:
<223> OTHER INFORMATION: example of vitamin D response element found in
      humans and/or mice
<220> FEATURE:
<221> NAME/KEY: misc_feature
<222> LOCATION: (7)..(7)
<223> OTHER INFORMATION: "n" can be a,t,g, or c
<220> FEATURE:
<221> NAME/KEY: misc_feature
<222> LOCATION: (8)..(8)
<223> OTHER INFORMATION: "n" can be a,t,g, or c
<220> FEATURE:
<221> NAME/KEY: misc_feature
<222> LOCATION: (9)..(9)
<223> OTHER INFORMATION: "n" can be a,t,g, or c

<400> SEQUENCE: 4
aggtcannna ggtca					15

<210> SEQ ID NO 5
<211> LENGTH: 13
<212> TYPE: DNA
<213> ORGANISM: Unknown
<220> FEATURE:
<223> OTHER INFORMATION: example of Peroxisome Profliferator-Activated -continued

```
      Receptor Response Element found in humans and/or mice
<220> FEATURE:
<221> NAME/KEY: misc_feature
<222> LOCATION: (6)..(6)
<223> OTHER INFORMATION: "n" can be a,t,g, or c

<400> SEQUENCE: 5
aggtcnaagg tca                                                         13

<210> SEQ ID NO 6
<211> LENGTH: 16
<212> TYPE: DNA
<213> ORGANISM: Unknown
<220> FEATURE:
<223> OTHER INFORMATION: example of thyroid response element found in
      humans and/or mice
<220> FEATURE:
<221> NAME/KEY: misc_feature
<222> LOCATION: (7)..(7)
<223> OTHER INFORMATION: "n" can be a,t,g or c
<220> FEATURE:
<221> NAME/KEY: misc_feature
<222> LOCATION: (8)..(8)
<223> OTHER INFORMATION: "n" can be a,t,g or c
<220> FEATURE:
<221> NAME/KEY: misc_feature
<222> LOCATION: (9)..(9)
<223> OTHER INFORMATION: "n" can be a,t,g or c
<220> FEATURE:
<221> NAME/KEY: misc_feature
<222> LOCATION: (10)..(10)
<223> OTHER INFORMATION: "n" can be a,t,g or c

<400> SEQUENCE: 6
aggtcannnn aggtca                                                      16

<210> SEQ ID NO 7
<211> LENGTH: 13
<212> TYPE: DNA
<213> ORGANISM: chicken
<220> FEATURE:
<221> NAME/KEY: misc_feature
<222> LOCATION: (7)..(7)
<223> OTHER INFORMATION: "n" can be a,t,g, or c

<400> SEQUENCE: 7
aggtcanagg tca                                                         13

<210> SEQ ID NO 8
<211> LENGTH: 9
<212> TYPE: DNA
<213> ORGANISM: homo sapiens
<220> FEATURE:
<221> NAME/KEY: misc_feature
<222> LOCATION: (2)..(2)
<223> OTHER INFORMATION: "n" can be a,t,g, or c
<220> FEATURE:
<221> NAME/KEY: misc_feature
<222> LOCATION: (9)..(9)
<223> OTHER INFORMATION: "h" can be a, c or t/u
<220> FEATURE:
<221> NAME/KEY: misc_feature
<222> LOCATION: (7)..(7)
<223> OTHER INFORMATION: "h" can be a, c or t/u
<220> FEATURE:
<221> NAME/KEY: misc_feature
<222> LOCATION: (1)..(1)
<223> OTHER INFORMATION: "v" can be a, g or c
<220> FEATURE:
<221> NAME/KEY: misc_feature
<222> LOCATION: (8)..(8)
<223> OTHER INFORMATION: "n" can be a,t,g, or c

<400> SEQUENCE: 8
``` vngatahnh                                                                9

<210> SEQ ID NO 9
<211> LENGTH: 22
<212> TYPE: DNA
<213> ORGANISM: homo sapiens

<400> SEQUENCE: 9
gcatcattgc tgaggtcaag gc                                                22

<210> SEQ ID NO 10
<211> LENGTH: 18
<212> TYPE: DNA
<213> ORGANISM: homo sapiens

<400> SEQUENCE: 10
cgataccaag acctccac                                                     18

<210> SEQ ID NO 11
<211> LENGTH: 13
<212> TYPE: PRT
<213> ORGANISM: Artificial Sequence
<220> FEATURE:
<223> OTHER INFORMATION: Peptide 589 synthesised to mimic the proposed
      binding regions of RBP to its receptor

<400> SEQUENCE: 11

Gly Arg Val Arg Leu Leu Asn Asn Trp Asp Val Cys Ala
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Peptide 592 synthesised to mimic the proposed
      binding regions of RBP to its receptor

<400> SEQUENCE: 12

Met Lys Tyr Trp Gly Val Ala Ser Phe Leu Gln Lys Gly Asn Asp
1               5                   10                  15

<210> SEQ ID NO 13
<211> LENGTH: 18
<212> TYPE: DNA
<213> ORGANISM: Artificial Sequence
<220> FEATURE:
<223> OTHER INFORMATION: Primer sense 726-743 used to make probe against
      K10

<400> SEQUENCE: 13
tggaggctga catcaacg                                                     18

<210> SEQ ID NO 14
<211> LENGTH: 22
<212> TYPE: DNA
<213> ORGANISM: Artificial Sequence
<220> FEATURE:
<223> OTHER INFORMATION: Primer antisense 1257-1278 used to make probe
      against K10

<400> SEQUENCE: 14
tattcagtat tctggcactc gg                                                22

<210> SEQ ID NO 15
<211> LENGTH: 22

```
<212> TYPE: DNA
<213> ORGANISM: Artificial Sequence
<220> FEATURE:
<223> OTHER INFORMATION: Primer sense 195-217 used to make probe against
      K10

<400> SEQUENCE: 15
caggtggcta tggaggatta gg                                              22

<210> SEQ ID NO 16
<211> LENGTH: 22
<212> TYPE: DNA
<213> ORGANISM: Artificial Sequence
<220> FEATURE:
<223> OTHER INFORMATION: Primer antisense 687-708 used to make probe
      against K10

<400> SEQUENCE: 16
acctcattct catacttcag cc                                              22

<210> SEQ ID NO 17
<211> LENGTH: 22
<212> TYPE: DNA
<213> ORGANISM: Artificial Sequence
<220> FEATURE:
<223> OTHER INFORMATION: Primer sense 1046-1067 used to make probe
      against K1

<400> SEQUENCE: 17
gcatcattgc tgaggtcaag gc                                              22

<210> SEQ ID NO 18
<211> LENGTH: 18
<212> TYPE: DNA
<213> ORGANISM: Artificial Sequence
<220> FEATURE:
<223> OTHER INFORMATION: Primer antisense 1613-1630 used to make probe
      against K1

<400> SEQUENCE: 18
cacctccaga accatagc                                                   18

<210> SEQ ID NO 19
<211> LENGTH: 20
<212> TYPE: DNA
<213> ORGANISM: Artificial Sequence
<220> FEATURE:
<223> OTHER INFORMATION: Primer sense 422-441 used to make probe against
      K1

<400> SEQUENCE: 19
gtggttatgg tcctgtctgc                                                 20

<210> SEQ ID NO 20
<211> LENGTH: 22
<212> TYPE: DNA
<213> ORGANISM: Artificial Sequence
<220> FEATURE:
<223> OTHER INFORMATION: Primer antisense 1046-1067 used to make probe
      against K1

<400> SEQUENCE: 20
gccttgacct cagcaatgat gc                                              22

<210> SEQ ID NO 21
<211> LENGTH: 22
<212> TYPE: DNA
<213> ORGANISM: Artificial Sequence
```

-continued

```
<220> FEATURE:
<223> OTHER INFORMATION: Primer sense 214-235 used to make probe against
      CRABP II

<400> SEQUENCE: 21
atgtgatgct gaggaagatt gc                                              22

<210> SEQ ID NO 22
<211> LENGTH: 22
<212> TYPE: DNA
<213> ORGANISM: Artificial Sequence
<220> FEATURE:
<223> OTHER INFORMATION: Primer antisense 466-487 used to make probe
      against CRABP II

<400> SEQUENCE: 22
tcgttggtca gttctctggt cc                                              22

<210> SEQ ID NO 23
<211> LENGTH: 6
<212> TYPE: DNA
<213> ORGANISM: Unknown
<220> FEATURE:
<223> OTHER INFORMATION: Example of retinoic response element found in
      humans and/or mice

<400> SEQUENCE: 23 aggtca                                                                 6
```

TREATMENT OF HYPERPROLIFERATIVE DISEASES

CROSS REFERENCE TO RELATED APPLICATIONS

This application is a continuation-in-part of international application PCT/GB01/03694, filed Aug. 17, 2001 and claims priority from Great Britain Application No. 0020351.3, filed Aug. 17, 2000. The above-mentioned applications, as well as all documents cited herein and documents referenced or cited in documents cited herein, are hereby incorporated herein by reference.

FIELD

This invention relates to the treatment of diseases associated with cellular hyperproliferation in a patient, including psoriasis and cancer. The invention also relates to the treatment or alleviation of symptoms associated with photoageing.

BACKGROUND

A number of diseases are associated with hyperproliferation of cells, including psoriasis, the ichthyoses, cancer and cutaneous viral infections. Psoriasis is a chronic inflammatory disease characterised by hyperproliferation and impaired differentiation of keratinocytes. Currently, the symptoms of psoriasis are treated in a number of ways, including topical administration of retinoids to the patient. Other diseases such as acne vulgaris and photoageing also respond to retinoid therapy and are believed to involve additional retinoid-mediated mechanisms.

Retinoids have also been used for both treatment and prevention of the development of cancers (e.g. treatment of acute promyelocytic leukaemia and prevention of the development of cutaneous malignancies in renal transplant patients).

Current retinoid therapy is based upon the effect of carboxylic acid derivatives of vitamin A (in particular, retinoic acid, the endogenously active compound) which are able to transcriptionally regulate target genes. Exposure to retinoic acid and retinoids results in proliferating cells withdrawing from the cell cycle and differentiating in response to retinoic acid-induced transcription of a possible excess of 300 target genes. This is a "forced" differentiation that represents a reprogramming of the normal cell fate and can be considered as an instructive differentiation. Treatment with retinoids has been found to be effective in controlling psoriasis, tumours and in relieving the symptoms of photoageing.

However, despite the beneficial effects of retinoid treatment, its benefits are limited by potentially serious adverse effects including hepatotoxicity, hyperlipidaemia, inhibition of bone growth, cutaneous irritation, photosensitivity, alopecia and teratogenicity (Kemmett and Hunter, 1988, *Hospital Update*. March 1988, pp 1301-1313). These effects are related to the pharmacological dosages needed to achieve a therapeutic response. To date, the search for alternative retinoids and methods to use retinoids has produced only marginal reductions in the cutaneous adverse effects.

It is therefore an aim of the present invention to provide for a method of treatment of hyperproliferative diseases and diseases associated with photoageing which avoids the adverse effects of retinoid administration.

SUMMARY

The invention is based on the surprising discovery that it is possible to mimic the desirable physiological effects of retinoids on hyperproliferative cells, i.e., reduced proliferation and/or enhanced differentiation, as well as reversing the effects of photoageing, without exposing cells of a diseased or affected patient to pharmacological doses of retinoids. Such pharmacological doses are described below.

We have found that these physiological effects of retinoid therapy are achieved by reducing the endogenous level of retinoic acid in hyperproliferative cells or cells suffering from photoageing. Reduction of the endogenous level of retinoic acid in cells may be achieved in various ways, for example, by blocking the activity of a retinol binding protein receptor (RBPr) which transports retinol into the cell. Such blocking may be done by administering an antagonist of retinol binding protein receptor to the patient. The antagonist as described above preferably comprises an agent which is capable of inhibiting the interaction of retinol binding protein receptor with retinol binding protein. The antagonist may inhibit the interaction by binding to one or other, or both, of the retinol binding protein receptor and the retinol binding protein. Furthermore, inhibition of any of the enzymatically catalysed reactions in a pathway responsible for retinoic acid biosynthesis may also be used to reduce retinoic acid levels in the cell.

According to a first aspect of the invention, we provide a method of treating a patient suffering from a hyperproliferative disorder or photoageing, which method comprises lowering the endogenous level or activity of retinoic acid (RA) in a cell of the patient. Other aspects of the invention, and preferred embodiments, are set out in the independent and dependent claims as well as in the description.

DETAILED DESCRIPTION

Figure 1:
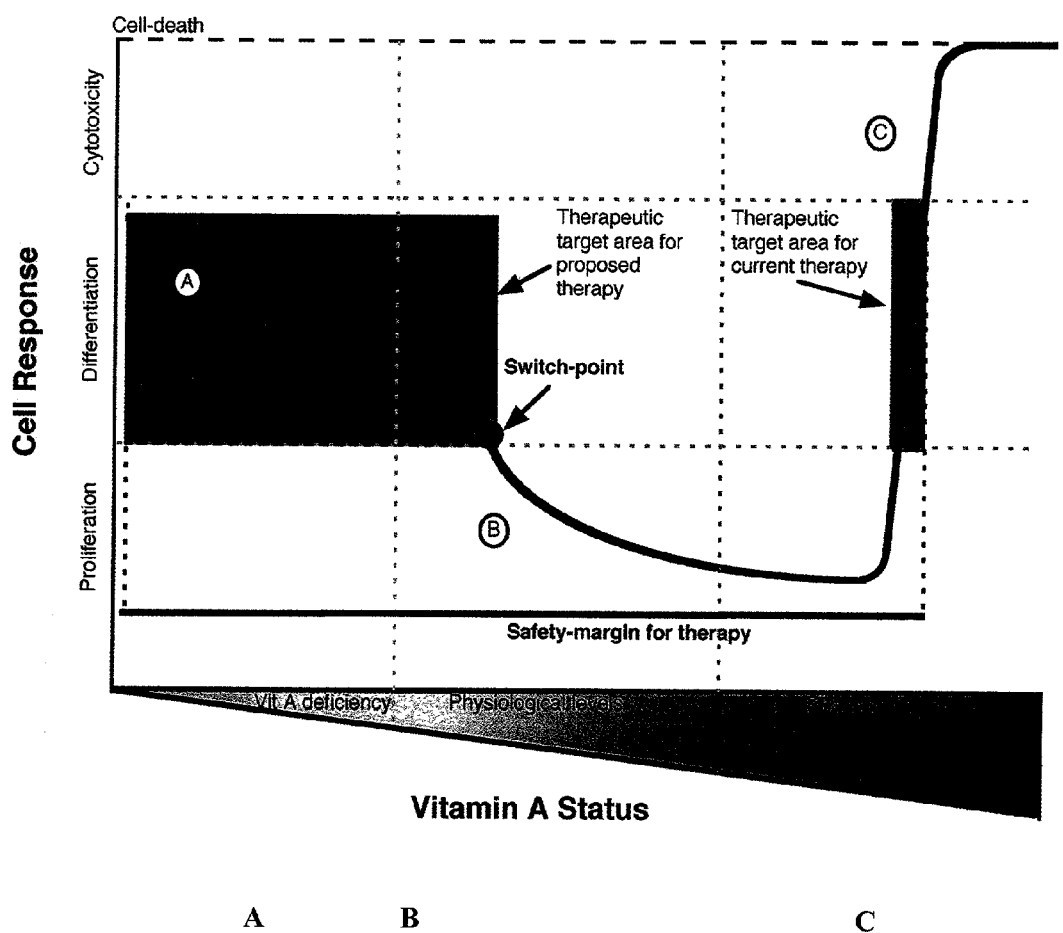
FIG. 1 is a diagram representing the relationship between current forms of retinoid therapy and an embodiment of a method according to our invention. The figure shows cell response, as measured by its resting state of proliferation, differentiation or death (cytotoxicity leading to necrosis), to increasing concentrations of retinoic acid (endogenous vitamin A signal derived from retinol in the blood and delivered to the cell by retinol binding protein-retinol binding protein receptor interaction).

The present invention is based on a novel mechanism to reduce proliferation and/or force differentiation in hyperproliferative cells of disease tissues, by mimicking the physiological effects of retinoids without the use of exposure to pharmacological levels of retinoic acid. We have discovered that reducing the endogenous concentration of retinoic acid in the cell similarly reduces proliferation. The methods according to our invention therefore generally rely on lowering the endogenous level of retinoic acid in the cells of a patient.

Thus, we find that blocking the activity of a retinol binding protein receptor involved in cellular accumulation of retinol from the systemic circulation ready for cellular uptake reduces proliferation. In addition, blocking the activity of a retinol binding protein receptor also reduces the effects of photoageing in cells of a patient. Thus, in one embodiment, therapy may be effected by reducing retinol binding protein uptake, for example, by administering to a patient an antagonist of a retinol binding protein receptor.

The retinol binding protein receptor is involved in uptake of retinol, which is converted into retinoic acid, the bioactive compound. Accordingly, when the biosynthesis of retinoic acid is inhibited, cells display reduced proliferation. In another embodiment therefore, the endogenous levels of retinoic acid are reduced.

Other methods besides targeting reduction of retinol uptake or retinoic acid synthesis may be employed, so long as their effect is reduce the endogenous level of retinoic acid within the cell. Such methods include modulation of expression, activity or degradation of any element of the machinery which ultimately results in retinoic acid synthesis. Thus, the expression of a retinol binding protein receptor may be down-regulated, by for example, antisense oligonucleotides to an mRNA coding for retinol binding protein receptor, or by down-regulation of transcription of such an mRNA, or by modulation of mRNA transport, processing, degradation, etc. Translation of retinol binding protein receptor from retinol binding protein receptor mRNA may also be regulated as a means of down-regulating the expression of this protein. Such down-regulation or modulation may make use of methods known in the art, for example, by use of inhibitors of transcription or translation. Likewise, the expression, activity or degradation of any retinoic acid synthesis enzyme may be regulated to achieve reduction in endogenous retinoic acid levels.

A combination of two or more inhibitors may be used, for example, a combination of blocking retinol binding protein receptor and inhibiting a retinoic acid synthesis enzyme. Thus, an inhibitor of retinol uptake may be administered together with an inhibitor of retinol dehydrogenase, or an inhibitor of retinal dehydrogenase, or both. Furthermore, an inhibitor of retinol dehydrogenase may be used in combination with an inhibitor of retinal dehydrogenase. Such multiple treatments may be administered simultaneously or sequentially, for example, in rotation.

The methods and compositions described here work by reducing the endogenous retinoic acid level typically to at about or below a physiological concentration of that species. In contrast, therapies for the diseases described here have typically employed higher doses, often far higher doses of retinoids. We now find that similar therapeutic effects may be achieved without the administration of such pharmacological doses of retinoids.

By the term "pharmacological dose" (or "dosage" or associated forms such as "pharmacological range" or "pharmacological level"), we mean a dose of retinoids as currently used in conventional retinoid therapy. Such doses are typically in the range of milligrams per kilogram of body weight per day. For example, the oral dose for isotretinoin (Roacutane) is 1 mg per kg; for a person weighing 70 kg, the oral dose is 70 mg once per day for 4 months. As a further example, the dose for Acitretin (Neotigason) is 25 to 50 mg per day. Thus, a "pharmacological dose" when applied orally may be considered a dose of 0.1 to 1 mg per kilogram per person per day. When applied topically, retinoids such as all trans retinoic acid in topical formulations have been applied typically at 0.2 grams of a 0.025% preparation once per day. The concentration of retinoic acid in cells treated with conventional pharmacological doses is typically in the micromolar range, typically between 1.3 to 2.1 micromolar (Formelli et al., British Journal of Cancer 76:1655-1660, 1997). However, the term "pharmacological dose" may be taken to mean between 1 to 2.5 micromolar, or between 0.5 to 3 micromolar, preferably, 0.5, 1, 1.5, 2, 2.5, 3, 3.5, 4, 4.5 or 5 micromolar.

In contrast, the methods and compositions of our invention rely on reducing the endogenous level of retinoic acid, and operate on levels of retinoic acid far below the pharmacological dose range. Typically, therefore, the methods and compositions described here operate at, for example, below micromolar concentrations, preferably below 1.3 micromolar concentration, most preferably at nanomolar (1 nanomolar to 999 nanomolar, preferably below 900 nanomolar, more preferably below 800, 700, 600, 500, 400, 300, 200, 100, 50 or below) or even sub-nanomolar concentrations of retinoic acid.

Preferably, the level of endogenous retinoic acid is reduced by 10%, 20%, 30%, 40%, 50%, 60%, 70%, 80% or more by the methods described here.

According to our methods, the concentration of retinoic acid is varied about the switch point in order to effect the therapy or effects described here. Most preferably, the level of endogenous retinoic acid is reduced to about or below the "switch point".

The "switch point" is the concentration of retinoic acid in the cell about which a change in concentration of retinoic acid in either direction (i.e., increase or reduction) will change the differentiation or proliferative fate of a cell. Concentrations of retinoic acid above the switch point cause the cell to undergo proliferation, while concentrations of retinoic acid below the switch point cause the cell to undergo differentiation. The switch point may therefore be determined in any cell or cell type or disease state according to this criterion, by methods known in the art and also described here.

In a normal undiseased cell, the switch point is typically at or about the physiological retinoic acid concentration; as described above, this will be below the concentration of retinoic acid used in conventional pharmacological therapy. The physiological retinoic acid concentration in a normal cell is between about $4 \times 10^{-9}$ molar and $1 \times 10^{-8}$ molar (i.e., between about 4 to 10 nanomolar), and accordingly, this range may be taken as a working range for the switch point.

In a highly preferred embodiment of the invention, the endogenous level of retinoic acid is reduced by 10%, 20%, 30%, 40%, 50%, 60%, 70%, 80% or more below the switch point. Thus, in one embodiment, the methods and compositions rely on reducing the endogenous retinoic acid level in a relevant cell, for example, a diseased cell or a cell in a diseased individual, to below about 10 nanomolar, preferably below about 4 nanomolar, more preferably below 1 about nanomolar, most preferably below about 750 picomolar, below about 500 picomolar, below about 50 picomolar or below about 1 picomolar.

Preferably, the concentration of endogenous retinoic acid is reduced below the switch point, but is maintained at a high enough level to avoid cell death.

Endogenous or intracellular retinoic acid levels may be assayed by various means as known in the art. For example, endogenous retinoic acid levels may be measured by staining cells with an antibody against retinoic acid and quantitating fluorescence levels by microscopy or fluorescence activated cell sorting. Direct analysis by High Pressure Liquid Chromatography (HPLC) or Gas Chromatography may also be used. Retinoic acid levels may also be measured by assaying the expression of a reporter construct comprising a reporter gene, such as lacZ expressing β-galactocidase, linked to a Retinoic Acid Response element (RPE). Construction of such retinoid-sensitive reporter constructs and assays for reporter gene activity are known in the art and are disclosed, for example, in Mendelsohn et al., *Development* 113:723-734, 1991 and Rossant et al., *Genes and Development* 5:1333-1344, 1991.

Although the primary benefit of the methods and compositions of our invention is the reduction of cellular proliferation, treating the hyperproliferative cells or photoaged cells may induce differentiation as an additional benefit.

The methods and compositions of our invention are useful for treatment of a variety of hyperproliferative diseases including psoriasis and cancer. In particular, the methods and compositions of our invention are especially useful for the treatment of psoriasis. Our invention is also useful in treating or alleviating the symptoms of photoageing or photodamage. It will be appreciated however that cells of patients suffering from skin hyperproliferative diseases (as described in further detail below), photoaged or photodamaged cells, as well as cancer cells may share many properties with each other. For example, cells of a patient exposed to ultraviolet radiation may display symptoms of photoageing; in addition, these cells may develop into various carcinomas such as basal cell carcinoma or squamous cell carcinoma as a result of such exposure.

In general, the methods and compositions described here are may be used to treat or alleviate the symptoms of a patient suffering from any disease in which there is an imbalance between proliferation and differentiation. Thus, any condition, etc, in which there is a failure in the normal controls which regulate the differentiative or proliferative fate of the cell may be treated. Such a disease will typically involve a cell or tissue type proliferating which normally (i.e., depending on the developmental stage or tissue type) does not or should not proliferate, or which fails to differentiate when the corresponding normal cell or tissue type is in a differentiated state. In a particular embodiment, the methods and compositions are suitable for treating, etc, a hyperproliferative disease, in particular a hyperproliferative disease which affects the skin. Photoageing, neoplasms and cancer are also suitably treated, and other diseases and conditions are disclosed below.

The methods of our invention result in a reduction of proliferation, preferably proliferation in vivo, of the hyperproliferative cells. More preferably, proliferation of a population of cells is reduced to 90%, 80% 70%, 60%, 50%, 40%, 30%, 20%, or less compared to a similar population of untreated cells. Most preferably, proliferation is reduced to 0%, i.e., the cells cease dividing completely.

A preferred method of assaying reduction of proliferation is by measurement of mitotic index. "Mitotic index" as used here means the percentage of cells in a given population which are undergoing mitosis and/or cell division. Other assays are possible, for example, measurement of cell cycle period.

As used here, the term "proliferation" is intended to mean the division of cells resulting in growth of a tissue. Proliferative cells are actively dividing, and undergo such cell cycle processes as DNA replication, mitosis, cell division etc. Various methods are known by which proliferation may be assayed, for example, by radiolabelling with radioactive nucleotide triphosphates, tritiated thymidine, bromodeoxyuridine etc to detect replicating cells, by visual examination for mitotic cells etc. Proliferation may also assayed by expression of markers such as Ki-67, or by determining the increase in cell numbers by direct counting of cultured cells under different conditions.

By "hyperproliferation" we mean increased proliferation compared to expected proliferation for a cell type, given its stage of development and function. The term is not intended to include transient increased proliferation of cells within a population, for example in response to a stimulus, which response is expected. For example, it is known that cells in tissues will exhibit increased proliferation when a tissue is injured and more cells are needed to repair a defect in tissue or to replace dead cells. Thus, "hyperproliferation" is specifically intended to refer to increased proliferation in the context of a diseased or otherwise abnormal state, for example, increased proliferation in the case of cancers and psoriasis.

In a highly preferred embodiment of the invention, our methods result in cell differentiation occurring within some or all of the population of treated cells. Preferably, 10% or more of a hyperproliferative cell population undergoes differentiation after treatment according to our invention compared with a population of untreated cells. More preferably, this percentage is 20%, 30%, 40%, 50%, 60%, 70%, 80% or more. Most preferably, 90%, 95% or 100% of the cell population undergoes differentiation.

"Differentiation" refers to the process by which unspecialised cells of tissues become specialised for particular functions. Differentiation of a cell may be assessed in various ways, for example morphologically, or by assaying expression of protein markers specific for the differentiated cell type as known in the art. For example, K1 and K10 keratin are markers for commitment to terminal differentiation of epidermal keratinocytes, and expression is increased when cellular differentiation occurs. In addition to K1 and K10 keratin, other keratin subtypes may be used as markers for different differentiation stages, for example, K5, K14, K16 and K17. Other non-keratin markers, for example EGF-receptor and β-1 integrin, may also be used as markers for cellular differentiation.

We have found that lowering of retinoic acid levels within the cells triggers a permissive differentiation that allows the cells to achieve their normal cell fate. Physiological concentrations of retinoic acid allow both cell proliferation and differentiation, whereas very low or pharmacological concentrations result in cell differentiation. Antagonising the retinol binding protein receptor (RBPr), and/or inhibition of the synthesis of retinoic acid, can therefore be used as the basis of therapeutic treatment of any disease where hyperproliferation is a component of the pathophysiology of the disease. Thus, the method described here may be used to treat any disease which is treatable by administration of retinoids, i.e., a retinoid sensitive disorder. Such a retinoid sensitive disorder is typically treated, in the art, by administration of retinoid to the patient so that higher than physiological levels of retinoid exist within his cells. Examples of such disorders are known in the art, and include psoriasis, acne, photoageing, cancer, acute promyelocytic leukaemia, psoriasis, disorders of keratinisation e.g. the ichthyoses and keratodermos, scleroderma, vitiligo, eczema, acne vulgaris and acne rosacea, lichen planus, cutaneous lupus erythematosus, pre-malignant conditions, e.g. melanocytic naevus, mrelodysplastic syndrome, among others.

Other types of diseases which are suitably treated by the methods described here include diseases which involve gene expression from any of several classes of response elements, including the retinoic acid response element (RARE), the vitamin D response element (VDRE), the peroxisome proliferator activated receptor response element (PPAR), and the thyroid hormone receptor (TRE) response element, and the peroxisome proliferator-activated response element (PPAR). Other response elements include the chicken ovalbumin upstream transcription factor (COUP-FF) response element and the apoAI regulatory protein-1 (ARP-1) response element. Thus, the methods as described here are suitable for treating or alleviating the symptoms of a patient suffering from a disease characterised by ectopic, over- or otherwise abnormal expression of a RARE responsive gene, a VDRE responsive gene, or a PPAR responsive gene or a TR responsive gene. The retinoid responsive retinoid X receptor forms heterodimers with the retinoic acid receptors, vitamin D receptor, thyroid hormone receptors and the peroxisome proliferator-activated receptor; the RXR dimers may be used as markers of this signaling function of these hormones.

According to the principle disclosed, modulating endogenous retinoic acid levels in a cell causes a shift in the proliferative/differentiative fate of the cell. Specifically, we have found that lowering the endogenous RA level causes a cell to cease proliferating, and/or start differentiating. Thus, our methods are generally suitable for treating or alleviating the symptoms of a patient suffering from any disease characterised by an imbalance between proliferation and differentiation, including cancer, tumours, and other skin hyperproliferative diseases as detailed in this document. An imbalance between proliferation and differentiation refers to an increase in the proportion of cells in a tissue engaged in mitosis over that which is normal for that tissue, or a decrease in the proportion of cells in a tissue engaged in mitosis below that which is normal for that tissue, or both. Other methods of detecting and assaying an imbalance are described elsewhere in this document.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, e.g., J. Sambrook, E. F. Fritsch, and T. Maniatis, 1989, *Molecular Cloning: A Laboratory Manual*, Second Edition, Books 1-3, Cold Spring Harbor Laboratory Press; B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts are herein incorporated by reference.

Reduction of Endogenous Retinoic Acid Levels

Our invention in one aspect relies on the fact that that reducing the physiological quantity of vitamin A available to a hyperproliferative cell, in other words, the endogenous levels of retinoic acid, to a cell is found to result in its terminal differentiation.

FIG. 1 shows the response of a typical "normal" (i.e., not diseased) cell, as measured by its resting state of proliferation, differentiation or death (cytotoxicity leading to necrosis), to increasing endogenous concentrations of retinoic acid. A similar response is shown by a hyperproliferative cell. As described in further detail elsewhere in this document, the concentration of retinoic acid within the cell is dependent on uptake of retinol. One of the ways retinol is taken into the cell is by means of the retinol binding protein receptor, which binds to and uptakes retinol from the retinol binding protein complex. The concentration of retinoic acid within the cell is also dependent on the activity of the retinoic acid biosynthetic pathways as described elsewhere in this document.

Point C of FIG. 1 represents a higher than physiological concentration of retinoic acid. This region represents current pharmacological therapy for hyperproliferative diseases such as psoriasis and cancer as well as photoageing. Initial slight increases in retinoic acid concentrations cause further cell proliferation. After this, higher retinoic acid concentrations rapidly cause cytotoxicity and cell death. The transition between proliferation and cytotoxicity defines a region where the cell phenotype is essentially scrambled by ectopic retinoic acid-induced gene transcriptional regulation. This altered phenotype is the current basis for therapy. The marginal difference, and probably random distribution, accounts for the associated toxicology of this retinoid therapy. Therefore, use of pharmacological levels of retinoic acid is limited by adverse effects as evidenced by the proximity of the pharmacological, therapeutic concentration range to the toxic threshold.

Point B of FIG. 1, on the other hand, represents a physiological concentration of retinoic acid. In this region a cell processes the vitamin A signal (i.e., retinoic acid) and uses it to decide upon whether it should remain in a proliferative state or differentiate. We have discovered that it is a drop in vitamin A-signalling that initiates cell differentiation. Physiological levels of retinoic acid are not likely to be associated with significant toxicity.

Point A represents a lower than physiological concentration of retinoic acid. Such levels are associated with vitamin A deficiency (VAD). In one aspect, the invention encompasses lowering the endogenous levels of retinoic acid to below physiological concentrations, as well as complete deprivation of retinoic acid signal, to reduce proliferation and enhance cellular differentiation.

As can be seen in FIG. 1, there exists a concentration of intracellular retinoic acid about which the proliferative/differentiative fate is capable of being switched. This concentration is shown in FIG. 1 as the "switch point". At concentrations of retinoic acid which are above the switch point, the cell undergoes proliferation; at concentrations below this switch point, the cell undergoes differentiation. The switch point concentration is approximately, but need not necessarily be, the same as the physiological concentration of retinoic acid of the relevant cell.

A method according to a preferred embodiment of our invention relies on reducing the endogenous or intracellular concentration of retinoic acid in a hyperproliferative cell to below the switch point of a particular cell, in order to cause it to reduce or stop proliferation, and optionally to undergo differentiation. Preferably, the endogenous levels of retinoic acid are lowered to only such an extent as to reduce or stop proliferation, i.e., just below the switch point. However, as indicated above, the retinoic acid concentration within a cell may be reduced further (i.e., to below the switch point, for example, complete deprivation of retinoic acid) to achieve these aims.

It will be appreciated that this switch-point is not in proximity to concentrations of retinoic acid that cause toxicity. Therefore, the methods according to our invention are advantageous in that they would not be expected to have the adverse side effects of cytotoxicity and cell death.

The retinoic acid concentration in the cell may be assayed by various means as known in the art, for example, HPLC of a sample as described in Pappas R S, Newcombe M E. and Ong D E, *Biology of Reproduction* 48:235-247, 1993

Retinoids

According to one aspect of the invention, beneficial therapeutic effects are achieved by reducing the endogenous retinoic acid level in a cell. The methods of our invention may be used to treat diseases which are associated with hyperproliferation of cells or with photoageing. These diseases are conventionally treated by administration of high levels of retinoids. Furthermore, our methods are suitable for treating or alleviating the symptoms of a patient suffering from a retinoid sensitive disorder, which retinoid sensitive disorder is a disorder which is treatable by administration of retinoids. Such a retinoid sensitive disorder may be a disorder which is treated or whose symptoms are alleviated by administration of higher than physiological levels of retinoid to the patient.

The above methods preferably comprise inhibiting the activity of a retinol binding protein receptor in cells of the patient, and/or inhibiting the biosynthesis of retinoic acid in the cells of the patient.

"Retinoids" are a class of compounds consisting of four isoprenoid units joined in a head-to-tail manner. All retinoids may be formally derived from a monocyclic parent compound containing five carbon-carbon double bonds and a functional group at the terminus of the acyclic portion. Furthermore, several synthetic compounds with retinoic acid-like activity have recently been developed and are included in the term 'retinoids', e.g. the arotenoids. As employed herein, the term "retinoids" refers to naturally occurring compounds with vitamin A activity, synthetic analogs, and various metabolites thereof.

Numerous retinoids have been identified, as described, for example, by Sporn, Roberts and Goodman in the two volume treatise entitled The Retinoids (Academic Press, N.Y., 1984), to which the reader is directed for further detail. Exemplary retinoids include retinol, retinyl acetate, retinyl hexadecanoate, α-retinyl, 4,14-retroretinol, deoxyretinol, anhydroretinol, 3,4-didehydroretinol, 15,15-dimethyl retinol, retinyl methyl ether, retinyl phosphate, mannosyl retinyl phosphate, retinol thioacetate, retinal (retinaldehyde), 3,4-didehydroretinal, retinylidene acetylacetone, retinylidene-1, 3-cyclopentanedione, retinal oxime, retinaldehyde acetylhydrazone, retinoic acid, 4-hydroxyretinoic acid, 4-oxoretinoic acid, 5,6-dihydroretinoic acid, 5,6-epoxyretinoic acid, 5,8-epoxyretinoic acid, the open-chain $C_{20}$ analog of retinoic acid (i.e., (all-E-3,7,11,15-tetramethyl-2,4,6,8,10,12,14-hexadecaheptaenoic acid), 7,8-didehydroretinoic acid, 7,8-dihydroretinoic acid, "Acid" (E,E)-3-methyl-5-(2,6,6-trimethyl-2-cyclohexen-1-yl)-2,4-pentanedioic acid), "$C_{17}$ Acid" ((E, E,E)-5-methyl-7-(2,6,6-trimethyl-1-cyclohexen-1-yl)-2,4,6-hepatrienoic acid), "$C_{22}$ Acid" (14'-apo-γ, psi.-carotenoic acid), retinoic acid esters (e.g., methyl ester, ethyl ester, etc.), retinoic acid ethylamide, retinoic acid 2-hydroxyethylamide, methyl retinone, "$C_{18}$ Ketone" 6-methyl-8-(2,6,6-trimethyl-1-cyclohexen-1-yl)-3,5,7-ocatrien-2-one), and the like.

The term "retinoic acid" includes the compounds known as tretinoin, vitamin A acid and vitamin A1 acid, and derivatives having the biological activity of retinoic acid.

As used here, the term "retinol" is intended include a compound (2E,4E,6E,8E)-3,7-dimethyl-9-(2,6,6-trimethyl-cyclohex-1-en-1-yl)nona-2,4,6,8-tetraen-1-ol, also known as vitamin A, vitamin A alcohol, vitamin A1, vitamin A1 alcohol, axerophthol or axerol. The term also includes retinoids exhibiting qualitatively the biological activity of retinol, as well as derivatives of any of the above compounds having the activity of retinol.

Reference may also be made to the definitions of these terms according to the 1981 Recommendations on the Nomenclature of Retinoids, as published by the IUPAC-IUB Joint Commission on Biochemical Nomenclature (JCBN). The reader is referred to G. P. Moss (*Arch. Biochem. BIophys.*, 1983, 224, 728-731; *Eur. J. Biochem.*, 1982, 129, 1-5; *J. Biol. Chem.*, 1983, 258, 5329-5333; *Pure Appl. Chem.*, 1983, 55, 721-726; *Biochemical Nomenclature and Related Documents*, 2nd edition. Portland Press, 1992, pages 247-251), and the on-line copy of the Nomenclature of Retinoids, Recommendations 1981 as provided by the School of Biological & Chemical Sciences at Queen Mary, University of London.

The body's requirement for vitamin A (retinol) must be satisfied by an adequate dietary intake. Vitamin A is obtained from two sources, firstly as retinyl esters within animal fats and secondly as β-carotene from vegetable sources. β-carotene is a member of a family of molecules known as carotenoids. β-carotene is also referred to as the provitaminn form of vitamin A.

Ingested β-carotene is cleaved in the lumen of the intestine by β-carotene dioxygenase to yield retinal. Retinal is reduced to retinol by retinaldehyde reductase, an NADPH requiring enzyme within the intestines. Retinol is esterified mainly to palmitic acid and delivered to the blood via chylomicrons. The uptake of chylomicron remnants by the liver results in delivery of retinol to this organ for storage as a lipid ester within lipocytes or stellate cells. Transport of retinol from the liver to extrahepatic tissues occurs by binding of hydrolyzed retinol to retinol binding protein (RBP). The retinol-retinol binding protein complex is then transported to the cell surface within the Golgi and secreted.

The retinol binding protein bound retinol can then interact with cell surface receptors on target tissues, in particular, the retinol binding protein receptor, which regulates the cellular uptake of retinol. The cellular retinol binding protein (CRBP) is ready to bind any retinol that is taken up by the cell. CRBP transports the retinol to oxidising enzymes such as retinol dehydrogenase and retinal dehydrogenase which convert the retinol to its biologically active metabolite retinoic acid (RA).

The first, and rate limiting, step in retinoic acid synthesis involves the oxidation of retinol to retinal by means of retinol dehydrogenase. Thus, it is known that a family of microsomal short-chain retinol dehydrogenases (RDH) enzymes are able to catalyze the oxidation of retinol to retinal. Such enzymes include RoDH1, RoDH2, RoDH3, RoDH4, CRAD1, CRAD2, RDH5 and retSDR1. The substrate preference and expression domains of these enzymes vary and the enzyme most likely to be physiological in the human skin is RoDH4 (Genbank accession number AF086735; Jurukovski et al, 1999., Mol. Genet. Metab. 67 (1), 62-73, 1999.). A family of cytosolic medium chain alcohol dehydrogenases has also been suggested to be important for oxidation of retinol to retinal, namely, ADH1, ADH2 and ADH4.

The final step to generate RA is mediated by a family of cytosolic enzymes called retinal dehydrogenases (RalDH), including ALDH1, ALDH6, RALDH2 and ALDH-t. The the most likely physiological enzyme in human skin is RALDH2. Two RalDHs have been shown to be physiologically important for RA synthesis (RalDH1 and RalDH2): Haselbeck et al. Distinct functions for Aldh1 and Raldh2 in the Control of Ligand Production for Embryonic Retinoid Signaling Pathways. Developmental Genetics 25:353-364, 1999. Like the RDHs the substrate preference and expression domains of the RalDHs vary. Neiderreither et al. Embryonic retinoic acid synthesis is essential for early mouse post-implantation development. Nature genetics 21:444-448, 1999.

The accession numbers of the above enzymes are RoDH4 (XM 006765), ADH1 (XM052368), ADH2 (M32657), ADH4 (XM 052361), ALDH1 (NM000689), ALDH6 (U07919), RALDH1 (XM030472), RALDH2 (NM003888), RDH5 (XM006732) and retSDR1 (AF061741).

Within cells both retinol and retinoic acid bind to specific receptor proteins, namely, retinoic acid receptors (RAR) and retinoid X receptors (RXR). Following binding, the receptor-vitamin complex interacts with specific sequences in several genes involved in growth and differentiation and affects expression of these genes. Thus, the RAR and RXR form heterodimers that interact with retinoic acid response elements (RARE) within genes to modulate their transcription.

Inhibition of Retinoic Acid Biosynthesis

According to one aspect of the invention, endogenous retinoic acid levels within a cell are reduced by interfering with retinoic acid biosynthesis. Thus, the native retinoid metabolic pathway may be targeted as a means of reducing endogenous retinoid levels and achieving the beneficial effects disclosed here. Reduction of endogenous retinoic acid levels may be achieved by inhibiting retinoic acid synthesis, for example, by inhibiting any retinoic acid synthesis enzyme. Specifically, we disclose that inhibitors of retinol dehydrogenase and/or retinal dehydrogenase will lower retinoic acid availability and result in alterations of gene expression affecting the balance between cellular proliferation and differentiation.

Any step in the biosynthetic pathway may be targeted for inhibition, including oxidation of retinol to retinal, oxidation of retinal to retinoic acid, as well as upstream and downstream steps. Preferably, an upstream step such as cellular uptake of retinol from holo-RBP is inhibited. Furthermore, synthesis of retinol binding protein in the liver, or export of retinol from the liver, could also be inhibited. The reduction in endogenous retinoic acid levels may also be effected by regulation of degradation of retinoic acid. For example, metabolic enzymes which degrade retinoic acid, such as CYP26, may be upregulated in order to reduce retinoic acid levels.

Binding of retinoic acid to a receptor, for example a nuclear receptor, maybe targeted by use of specific antagonists of RAR/RXR, for example. Such RAR/RXR antagonists are described in WO 94/14777, Yoshimura et al. *J Med. Chem.* 38: 3163-3173 (1995). Kaneko et al. *Med. Chem Res.* 1:220-225 (1991); Apfel et al. *Proc. Natl. Acad. Sci. USA* 89: 7129-7133 Augusty 1992 *Cell Biology*; Eckhardt et al. *Toxicology Letters* 70:299-308 (1994); Keidel et al. *Molecular and Cellular Biology* 14:287-298 (1994); and Eyrolles et al. *J. Med. Chem.* 37: 1508-1517 (1994). Any of these steps may be targeted alone or in combination with others.

In a preferred embodiment, the activity of a retinoic acid synthesis enzyme is antagonised or inhibited. This term should be taken to refer to any enzyme involved in any pathway which leads directly or indirectly to the production or synthesis or retinoic acid, or to an increase in retinoic acid level.

Any agent, antagonist or inhibitor of any retinoid biosynthetic step may be used. Included are antibodies against an enzyme involved in biosynthesis of retinoic acid, as well as inhibitors, which may be competitive or non-competitive. Thus, a molecule which binds to the active site of an enzyme (or indeed to any other part of the enzyme, preferably near the active site) in the retinoid synthesis pathway in a manner which interferes with the activity of the enzyme may be used for the purposes of this invention. The molecule may be a small molecule, or it may be a peptide, for example, a fragment of a natural substrate such as retinoic acid for the enzyme. Furthermore, the molecule may be a peptide capable of interfering with the interaction of CRBPI or II with the enzyme. Use of such a molecule inhibits the delivery of the substrate without interacting or interfering with active site of the enzyme.

The molecule may be a known inhibitor of the enzyme, or may be identified by means known in the art, for example, by screening a library of molecules (for example, a combinatorial library) for compounds which interfere with the enzyme activity.

Furthermore, other means of disrupting enzyme function may be used, for example, antisense nucleic acids, including antisense DNA, RNA or PNA (protein-nucleic acid). Other means of antagonising the activity of a retinoid synthesis enzyme may be derived from the section describing "Antagonists" below.

Known inhibitors of retinol dehydrogenase include Carbenoxolone, Phenylarsine and Citral. Both short chain alcohol dehydrogenase specific inhibitors as well as medium chain alcohol dehydrogenase specific inhibitors may be employed. Examples of these include:

Carbenoxolone which may be used at 0.5 mM in vitro-microsomes as described in *Cloning & characterization of retinol dehydrogenase transcripts expressed in human*

*keratinocytes*, Jurukovski V., Markova N. G., Karaman-Jurukovska N., Randolph R. K., Su J., Napoli J. L., Simon M. *Mol Gen. Met.* 67:62-73, 1999. An IC50 of 55 microM is established by Boerman M. H., Napoli J. L. *Characterization of a microsomal retinol dehydrogenase: a short-chain alcohol dehydrogenase with integral and peripheral membrane forms that interact with holo-CRBP (type* 1). *Biochemistry* 34:7027-37, 1995

Phenylarsine oxide which has an IC50 of 5 microM as described in Boerman M. H., Napoli J. L. Characterization of a microsomal retinol dehydrogenase: a short-chain alcohol dehydrogenase with integral and peripheral membrane forms that interact with holo-CRBP (type 1). Biochemistry 34:7027-37, 1995

Citral (3,7-dimethyl-2,6-octadienal), which may be used at 20 μM, as described in Gough W. H., VanOoteghem., Sint T., Kedishvili Y. cDNA cloning and characterization of a new human microsomal NAD+-dependent dehydrogenase that oxidizes all-trans-retinol and 3α-hydroxysteroids. JBC 273:19778-85, 1998. Citral may be used at a concentration of 11 μM topical on skin, as described in Connor M. J., Smit M. H. Terminal-group oxidation of retinol by mouse epidermis. Inhibition in vitro and in vivo. Biochemical Journal 244:489-92, 1987

4-Methylpyrazole may be used at 0.2 mM, as described in Baum et al. Fomepizole treatment of ethylene glycol poisoning in an infant. Pedriatics 106:1489-1491, 2000.

Known inhibitors of retinal dehydrogenase include Citral and Disulphiram (aka disulfuram).

Disulphiram was used at $10^{-5}$ M in whole mouse embryo culture as described by Antoni. *The role of retinoic acid during the early development of the vertebrate limb*. M. Phil University of Sheffield, August 2000. It inhibits all retinal dehydrogenases and has been used for preventing retinoic acid synthesis in developmental studies (Stratford T., Horton C., Maden M. Retinoic acid is required for the initiation of outgrowth in the chick limb bud. Current Biology 6:1124-33, 1996; Xavier-Neto et al. A retinoic acid-inducible transgenic marker of sino-atrial development in the mouse heart. Development 126:2677-2687, 1999, in which 1.33 mg disulfiram/g in DMEM is injected subcutaneous into pregnant female mice at e6.5.

Citral has an IC50 of 1 microM for RalDHI and an IC50 of 12 microM for RalDHII, as described by Penzes P., Wang X., Napoli J. L. Enzymatic characterization of retinal dehydrogenase type 1 expressed in *Esherichia coli*. Biochimica et Biophysica Acta. 1342:175-81, 1997; Chen H., Juchau M. R Biotransformation of all-trans-retinal, 13-cis-retinal, and 9-cis-retinal catalyzed by conceptual cytosol and microsomes. Biochemical Pharmacology 53:877-85, 1997.

Other suitable enzyme inhibitors, as known in the art, may also be used.

Retinol Binding Protein and Receptor

According to one aspect of the invention, beneficial therapeutic effects are achieved by reducing the endogenous retinoic acid level in a cell, by blocking a retinol binding protein receptor, specifically, blocking the uptake of retinol binding protein by this receptor.

As used here, the term "retinol binding protein" refers to a protein capable of binding retinol; more specifically, it refers to a protein carrier of retinol as described above. Retinol binding protein is also known as "plasma retinol binding protein". Specifically, the term is preferably intended to refer to a mammalian retinol binding protein, more preferably a human retinol binding protein. Examples of retinol binding protein include the following from the GenBank database:

P02753 RETB_HUMAN PLASMA RETINOL-BINDING PROTEIN PRECURSOR (PRBP) (RBP)-HOMO

Q28369 RETINOL BINDING PROTEIN PRECURSOR-EQUUS CABALLUS (HORSE).

P27485 RETB_PIG PLASMA RETINOL-BINDING PROTEIN PRECURSOR (PRBP) (RBP)-SUS

P06912 RETB_RABIT PLASMA RETINOL-BINDING PROTEIN PRECURSOR (PRBP) (RBP)-ORYC

P18902 RETB_BOVIN PLASMA RETINOL-BINDING PROTEIN (PRBP) (RBP)-BOS TAURUS (BO

Q00724 RETB_MOUSE PLASMA RETINOL-BINDING PROTEIN PRECURSOR (PRBP) (RBP)-MUS

P04916 RETB_RAT PLASMA RETINOL-BINDING PROTEIN PRECURSOR (PRBP) (RBP)-RATT

P41263 RETB_CHICK PLASMA RETINOL-BINDING PROTEIN PRECURSOR (PRBP)-GALLUS GAL

P24775 RET2_ONCMY PLASMA RETINOL-BINDING PROTEIN II (PRBP-II)-ONCORHYNCHUS M

P24774 RET1_ONCMY PLASMA RETINOL-BINDING PROTEIN I (PRBP-I)-ONCORHYNCHUS MYK

P06172 RETB_XENLA PLASMA RETINOL-BINDING PROTEIN PRECURSOR (PRBP)-XENOPUS LA

P08938 PURP_CHICK PURPURIN PRECURSOR-GALLUS GALLUS (CHICKEN)

In a highly preferred embodiment, the retinol binding protein is a human retinol binding protein having GenBank Accession Number P02753 (GI: 132404).

Reviews of retinol binding proteins are provided in Goodman, in Sporn et al., Eds. The Retinols: 41-88 (Academic Press, 1984) and Blaner, 1989, *Endocrine Rev.* 10 308-316 (1989). Retinol binding protein is a well characterized 21 KDa protein and both the primary and tertiary structures are known (Newcomer et al., *EMBO J* 3: 1451-1454 (1984); Rask et al., *FEBS Letters* 104: 55-58 (1980)).

Retinol binding protein is structurally related to a number of extracellular proteins involved in the transport of small hydrophobic compounds, called the lipocalins (Pervaiz et al., *FASEB J* 1:209-214 (1987); Flower, 1996, *Biochem J.* 318 1-14 (1996)). Well known members of the lipocalin group of protein include β-lactoglobulin (Godovach-Zimmerman et al., *Hoppe-Seyler Biological Chemistry* 366:431-434 (1985)) apolipoprotein D (Drayna et al., *J. Biol. Chem.* 261: 16535-16539 (1986)), olfactory binding protein (Lee et al., *Science* 235:1053-1056 (1987)) and protein HC (Lopez et al., *Biochem. & Biophys. Res. Comm.* 103:919-925 (1981)).

A "retinol binding protein receptor" refers to a receptor which is capable of binding retinol binding protein, as described above.

The cloning and sequence of a bovine retinol binding protein receptor is disclosed in U.S. Pat. No. 5,573,939 (Accession Number I28766) and 5,679,772, as well as Bavik et al., 1993, *J Biol Chem,* 268(27):20540-6 (GenBank Accession Number X66277). These documents also describe the production of monoclonal and polyclonal antibodies to retinol binding protein receptor.

Nicoletti et al., 1995, *Hum. Mol. Genet.* 4 (4), 641-649 describes the cloning and characterisation of a human retinol binding protein receptor gene (GenBank Accession Number NM_000329). The gene encodes a 61kDa protein from retinal pigment epithelium, RPE65, which is 98.7% identical to the bovine.

A rat homologue of retinol binding protein receptor is described by Manes et al., 1998, *FEBS Lett.* 423 (2), 133-137. This document also describes the expression pattern of rat RPE65 mRNA using RT-PCR. The sequence has been deposited with GenBank Accession Number AF035673.

A tissue distribution of the retinol binding protein receptor is disclosed in Smeland et al., 1995, *Biochem J,* 305 (Pt 2):419-24.000. Isolation of a human retinol binding protein receptor is described in Sivaprasadarao et al., 1994, *Biochem J* 302 (Pt 1):245-51. Bavik et al., 1991, *Journal Of Biological Chemistry.* 266:14978-14985 describes assays for retinol binding protein receptor activity. An assay for retinol binding protein receptor activity using preferential precipitation of $^{125}$I-retinol binding protein-receptor complex with poly(ethylene glycol) is described in Sivaprasadarao et al., 1994 (supra).

Preferably, the retinol binding protein receptor is a mammalian retinol binding protein receptor expressed in keratinocytes. Methods of identifying and cloning such receptors are described in this document. More preferably, the mammalian retinol binding protein receptor is a homologue of a receptor having accession number I28766, X66277, NM_000329, I28766 (GI1819542), X66277 (GI563) or NM_000329 (GI4506590).

Nuclear Receptors and Response Elements

We further describe a method of treating or alleviating the symptoms of a patient suffering from a disease characterised by or associated with ectopic, over- or otherwise abnormal expression of a nuclear receptor response element regulated gene.

Nuclear receptors include receptors for glucocorticoids (GRs), androgens (ARs), mineralocorticoids (MRs), progestins (PRs), estrogens (ERs), thyroid hormones (TRs), vitamin D (VDRs), retinoids (RARs and RXRs), peroxisomes (XPARs and PPARs) and icosanoids (IRs). A nuclear receptor response element may therefore include a retinoic acid receptor response element (RARE), a vitamin D response element (VDRE), a thyroid hormone receptor response element or a peroxisome proliferator-activated receptor (PPAR) response element. Other response elements include chicken ovalbumin upstream transcription factor (COUP-FF) response element and the apoAI regulatory protein-1 (ARP-1) response element. Such a method comprises reducing the endogenous level or activity of retinoic acid (RA) in a cell of the patient, as described elsewhere in this document.

Preferably, the nuclear receptor is one which interacts with its cognate response elements as a heterodimer with the retinoid X receptor (RXR). Thus, preferably, the nuclear receptor is one which forms a heterodimer, preferably with the retinoid X receptor, and is capable of recognising a response element in which two AGGTCA (SEQ ID NO: 23) binding sites are arranged in tandem. Preferably, binding and recognition is capable of causing modulation of gene expression of a gene linked to the response element. The response element may be in any control region of a gene, for example, in an upstream control region such as a promoter or enhancer. Target selection by the complexes requires the spacing between the binding sites to act as the identity element.

Accordingly, any disease characterised or associated with ectopic expression, over-expression or abnormal expression from any nuclear receptor response element, preferably a nuclear response element or receptor as identified above, may be suitably treated (or a symptom or condition alleviated) by the methods and compositions described here.

Nuclear receptors represent a superfamily of proteins that specifically bind a physiologically relevant small molecule, such as hormone or vitamin. As a result of a molecule binding to a nuclear receptor, the nuclear receptor changes the ability of a cell to transcribe DNA, i.e. nuclear receptors modulate the transcription of DNA, although they may have transcription independent actions. Unlike integral membrane receptors and membrane associated receptors, the nuclear receptors reside in either the cytoplasm or nucleus of eukaryotic cells. Thus, nuclear receptors comprise a class of intracellular, soluble ligand-regulated transcription factors.

Nuclear receptors include receptors for glucocorticoids (GRs), androgens (ARs), mineralocorticoids (MRs), progestins (PRs), estrogens (ERs), thyroid hormones (TRs), vitamin D (VDRs), retinoids (RARs and RXRs), peroxisomes (XPARs and PPARs) and icosanoids (IRs). The so called "orphan receptors" are also part of the nuclear receptor superfamily, as they are structurally homologous to the classic nuclear receptors, such as steroid and thyroid receptors.

Generally, nuclear receptors specifically bind physiologically relevant small molecules with high affinity and apparent Kd's are commonly in the 0.01-20 nM range, depending on the nuclear receptor/ligand pair.

Proteins of the nuclear receptor superfamily display substantial regions of amino acid homology. Members of the nuclear receptor family display an overall structural motif of three modular domains: 1) a variable amino-terminal domain; 2) a highly conserved DNA-binding domain (DBD); and 3) a less conserved carboxyl-terminal ligand binding domain (LBD).

Nuclear receptors can exist in a variety of isoforms. For example, GR subfamily members have usually one receptor encoded by a single gene, although there are exceptions. For example, there are two PR isoforms, A and B, translated from the same mRNA by alternate initiation from different AUG codons. There are two GR forms, one of which does not bind ligand. The thyroid receptor usually has several receptors that are encoded by two (alpha and beta) genes, while RAR, RXR, and PPAR receptors are encoded by three (alpha, beta and gamma) genes. Alternate RNA splicing may also give rise to isoforms.

Nuclear receptor response elements are conserved sequences which are found in the upstream regions (promoters or enhancers) of genes whose expression is regulated by nuclear receptors. Such response elements are known in the art, and examples are disclosed below. They may be identified by empirical studies, homology searching, or by comparing upstream sequences of a gene of interest with computer programs, such as the MOTIF program. Expression of genes containing such response elements are likely to be modulated by the particular nuclear receptors. The methods described here are suitable for treating diseases associated with abnormal, ectopic or over-expression of such nuclear receptor response element mediated or responsive genes. Such diseases may be identified by methods known in the art, for example, by biochemical assays of diseased cells, by linkage studies, etc.

Retinoic Acid Response Element

Retinoids affect DNA transcription in a wide variety of mammalian cells. Retinoids exert their effects on transcriptional activity through intracellular retinoid receptors, which when complexed as heterodimers with a functional ligand bind to a specific retinoid response element, and subsequently modulate transcription.

The effects of retinoic acid on gene transcription can be mediated by retinoic acid receptors (RARs) and retinoid X receptors (RXRs). Leed, M. et al., *Cell* 53:377-395 (1992); Mangelsdorf, D. J. et al., *Genes Dev.* 6:329-344 (1992). RARs have been shown to bind retinoic acid (RA) with high affinity, while RXRs apparently have no affinity for this ligand. Mangelsdorf, D. J. et al., *Nature* 345:224-229 (1990). However, it is known that 9-cis RA can bind to RXR-α with high affinity. Levin, A. A. et al., *Nature* 355:359-361 (1992); Heyman, R. A. et al., *Cell* 68:397-406 (1992).

It has been found that RAR and RXR have a high degree of cooperativity in binding target DNA. For example, an RAR and RXR heterodimer binds to a DNA response element having two 6-nucleotide direct repeat sequences separated by a 5-nucleotide spacer sequence (DR-5), and strongly stimulates transcriptional activation (Kliewer et al., 1992, *Nature* 355:446-449).

An example of a retinoic acid response element (RARE) is the sequence AGGTCA [5 bp spacer] AGGTCA. (SEQ ID NO: 1) Another example of a retinoic acid response element is the DR-2 RARE with the sequence AGGTCA [2 bp spacer] AGGTCA. (SEQ ID NO: 2)

RXR-TR and RXR-RAR heterodimers have been recently shown to bind related response elements (with different spacers), i.e., DR-4 and DR-5 sites, respectively (see, Perlman et al., 1993, *Genes Develop.* 7:1400-1422; and Kurokawa et al., 1993, *Genes Develop.*, 7:1423-1435). It has also been found that RXR-RAR heterodimers bind to a related DNA response element having two 6-nucleotide direct repeat sequences separated by a 2-nucleotide spacer sequence (DR-2) (Rhodes et al., 1993, *Genes Develop.* 7:913-932).

A list of genes whose promoters comprise retinoic acid response elements is shown in Appendix 1. Expression of such genes is modulated by RAREs. Diseases characterised by, or associated with, over-, ectopic or otherwise abnormal expression of such genes include psoriasis, acne, photoageing, cancer, acute promyelocytic leukaemia, psoriasis, disorders of keratinisation e.g. the ichthyoses and keratodermos, acne vulgaris and acne rosacea, lichen planus, cutaneous lupus erythematosus, pre-malignant conditions, e.g. melanocytic naevus, mrelodysplastic syndrome, among others. Such diseases, and others are suitably treated by the methods described here.

Vitamin D Response Element

The consensus Vitamin D Response Element (VDRE) has the following sequence: GGGTGA NNG GGGGCA. (SEQ ID NO: 3) Another example of a vitamin D response element is the sequence AGGTCA [3 bp spacer] AGGTCA. (SEQ ID NO: 4)

A list of genes whose promoters comprise vitamin D response elements is shown in Appendix 1. Expression of such genes is modulated by VDREs. Diseases characterised by, or associated with, over-, ectopic or otherwise abnormal expression of such genes include psoriasis and other diseases and are suitably treated by the methods described here.

Peroxisome Proliferator-Activated Receptor (PPAR) Response Element

Peroxisomes in liver parenchymal cells proliferate in response to structurally diverse nonmutagenic compounds designated as peroxisome proliferators (PP). Three different PPAR subtypes have specific roles in different organs.

The induction of peroxisome proliferation is mediated by PP-activated receptor alpha (PPAR alpha), a member of a group of transcription factors that regulate the expression of genes associated with lipid metabolism and adipocyte differentiation. Three isotypes of this family of nuclear receptors, namely PPAR alpha, PPAR gamma, and PPAR delta (also referred to as hNUC1 or beta), have been identified as products of separate genes. PPAR alpha, mainly expressed in liver, plays an important role in fatty acid metabolism. PPAR gamma predominantly is expressed in adipose cells. PPAR delta displays a high level of expression in lipid-metabolizing organs such as small intestine, heart and adipose tissue. Naturally occurring and synthetic molecules (anti-hyperlipidemia and diabetic drugs) that are ligands for these nuclear receptors control transcriptional activity of PPARs. Although PPAR alpha is responsible for the PP-induced pleiotropic responses, PPAR gamma seems to be involved in adipogenesis and differentiation, but the events associated with PPAR gamma do not directly involve peroxisomes and peroxisome proliferation.

PPARs heterodimerize with 9-cis retinoic acid receptor (RXR), and bind to PP response element(s) (PPREs) on the target gene promoter to initiate inducible transcriptional activity. The complex binds to sequences termed direct repeat-1 response element in enhancer sites of regulated genes and activates transcription upon ligand and coactivator binding.

Tissue and species responses to PPs depend on pharmacokinetics, relative abundance of PPAR isotypes, nature of PPRE in the upstream regions of target genes, the extent of competition or cross-talk among nuclear transcription factors for PPAR heterodimerization partner retinoid X receptor and the modulating role of coactivators and corepressors on ligand-dependent transcription of PPARs.

Steroid receptor coactivator-1 (SRC-1) and PPAR-binding protein (PBP), have been identified as PPAR coactivators. Both SRC-1 and PBP contain LXXLL signature motifs, considered necessary and sufficient for the binding of coactivators to nuclear receptors.

The Peroxisome Proliferator-Activated Receptor (PPAR) Response Element has a sequence AGGTCA [1 bp spacer] AGGTCA (SEQ ID NO: 5), and is involved in regulation of expression of genes including cyclooxygenase (COX2), cytosolic phospholipase A2 (CPLA2), mitochondrial fatty acid beta—oxidising enzymes, ABCA1, ARE6, ARE7, GLUT2. Examples of disorders associated with abnormal, ectopic or over-expression of PPAR response element mediated genes include artherosclerosis, rheumatoid arthritis, inflammatory bowel disease, obesity, hypertension, diabetes, hyperlipidemia, colon cancer.

Thyroid Response Element

The thyroid response element has a consensus sequence 5'-AGGTCA [4 bp spacer] AGGTCA-3' (SEQ ID NO: 6), and is involved in regulation of expression of a variety of genes, including connexin43, hyperpolarization-activated cyclic nucleotide-gated channel gene (HCN2), C/EBPalpha, prohormone convertases (PC1) and (PC2), Purkinje cell protein (Pcp-2), Calbindin, Myo-inositoltriphosphate (IP-3) receptor, Neurotrophin-3 (NT-3), Nerve growth factor (NGF), Brain-derived nerotrophic factor (BDNF), Neurotrophin 4/5, Reelin, Neural cell adhesion molecule (NCAM), Tenascin-C, Srgl, Hairless, BCL-2, Myelin basic protein (MBP), pro-alpha1(I) collagen, uncoupling protein 3 (UCP3), medullary thyrotropin-releasing hormone (TRH), beta-amyloid precursor protein (APP), fatty acid synthase promoter, malic enzyme, steroid receptor coactivator-1 (SRC-1), sodium, potassium-adenosine triphosphatase alpha3, apolipoprotein CII and lipocalin-type prostaglandin D synthase (beta-trace), among others.

Diseases associated with ectopic, over-expression or abnormal expression of thyroid response element responsive genes, which diseases may be treated by the methods and compositions described here, include any disease associated with or any manifestation of hyperthyroidism (higher than normal thyroxine) or hypothyroidism (lower than normal thyroxine levels).

The manifestations of hyperthyroidism (and diseases associated with hypothyroidism) include aggitation, anxiety, loss of weight, diarrhoea, tachycardia and menstural disorders. The manifestations of hypothyroidism (and diseases associated with hypothyroidism) include dementia, depression, cold intolerance, obesity, alopecia, dry skin/eczema, lethargy, bradycardia/heart block, haematological eg anaemia, reduced metabolism, changes in lipid metabolism, constipation, glucose intolerance and menstrual disturbances. Each of these is suitable for treating or alleviating with the methods and compositions described here.

Other functions/diseases regulated by thyroid hormone signalling include cardiac pacemaking, hormonal homeostasis, brain development, myocardial fibrosis, thermogenesis, autonomic visceral function and Alzheimer's disease.

Diseases which may be treated by the methods and compositions described here include those involving over-expression, ectopic expression, or abnormal expression for other response elements including COUP-TR (chicken ovalbumin upstream promoter transcription factor II). Diseases associated with such expression from COUP-TR include Type I mature onset diabetes of the young (MODY1); genes which are under the control of this response element include hepatocyte nuclear factor 1. The chicken ovalbumin upstream promoter transcription factor II response element has a sequence AGGTCA [1 bp spacer] AGGTCA (SEQ ID NO: 7).

Another nuclear receptor which may be targeted is response element is ARP-1, which has a similar or identical sequence as the COUP-TR response element. Diseases associated with expression from ARP-1 include occulsive coronary artery disease (CAD), and genes whose expression is regulated from this response element include apolopoprotein A1 (apo A1).

Antagonists

The methods and compositions of our invention rely on blocking the activity of a retinol binding protein receptor to reduce proliferation of a hyperproliferative cell, for example by use of agent which interferes with the protein-receptor binding. Such an agent may be an antagonist of receptor function. Furthermore, the synthesis of retinoic acid (as described above) within the cell may be inhibited by a suitable inhibitor or antagonist of any enzyme involved in retinoic acid biosynthesis. In general, any antagonist which is capable of reducing the endogenous levels of retinoic acid within a cell is suitable for use in the methods described here.

The term "antagonist", as used in the art, is generally taken to refer to a compound which binds to a receptor and inhibits the effect of the native ligand. The term as used here, however, is intended to refer broadly to any agent which inhibits the activity of a receptor or enzyme, not necessarily by binding to it. Accordingly, it includes agents which affect the expression of the receptor or enzyme, or the expression of modulators of the activity of the receptor or enzyme. The specific activity which is inhibited may be any activity which is necessary for ligand binding and/or ligand uptake, or for enzyme activity, as the case may be. An antagonist of a retinol binding protein receptor has the ability to affect the binding of retinol binding protein and/or uptake ability of retinol (preferably in the form of a retinol-retinol binding protein receptor complex), as set out above. Similarly, an antagonist of a retinoic acid synthesis enzyme has the ability to affect the enzymatic activity of that enzyme, i.e., the conversion of retinol to retinal by retinol dehydrogenase, or the conversion of retinal to retinoic acid by retinal dehydrogenase. In general, however, an antagonist suitable for use in the methods described here should be one which is ultimately capable of reducing endogenous levels of retinoic acid.

The antagonist may bind to and compete for one or more binding sites on the receptor or enzyme. However, the antagonist need not necessarily bind directly to a binding site or active site, and may bind for example to an adjacent protein or other entity on or in the cell, so long as its binding blocks the interaction between the enzyme or receptor and a substrate or ligand.

An antagonist of a retinol binding protein receptor may include uncomplexed retinol binding protein, or a fragment of this which is capable of binding to the receptor. In addition, whole or fragments of retinol binding protein receptor generated natively or by peptide synthesis may be used to compete with retinol binding protein receptor for binding sites on the retinol binding protein-retinol complex. Similarly, an antagonist of a retinoic acid synthesis enzyme may include a fragment of its substrate capable of binding to the enzyme and inhibiting its activity. Alternatively, or in addition, an immunoglobulin capable of binding to the receptor protein, retinol binding protein or another protein, for example, on the cell surface, may be used so long as it interferes with the ability of retinol binding protein receptor to bind to retinol binding protein and/or uptake of retinol. The immunoglobulin may be a monoclonal or a polyclonal antibody. An immunoglobulin, monoclonal or polyclonal antibody against a retinoic acid synthesis enzyme may be used to inhibit its activity.

The antagonist may also include a peptide or other small molecule which is capable of interfering with a binding interaction. Other examples of antagonists are set forth in greater detail below, and will also be apparent to the skilled person.

For example, the antibodies described in Melhus et al., 1995, *Biochem Biophys Res Commun*, 210(1):105-12 may be used as retinol binding protein receptor antagonists. This document describes the generation of monoclonal antibodies (mAbs) to human retinol binding protein and characterisation of their ability to interfere with the receptor binding. MAbs to two conserved regions efficiently blocked the binding of retinol binding protein to retinol binding protein receptor. One blocking mAb showed reactivity to a synthetic peptide corresponding to one entrance loop of the retinol-binding pocket (amino acid residues 60-70).

Blocking the ability of retinol binding protein receptor to bind to and transport the retinol-retinol binding protein complex into the cell may also be achieved by reducing the level of expression of the retinol binding protein receptor in the hyperproliferative cell. For example, the cell may be treated with antisense compounds, for example oligonucleotides having sequences specific to the retinol binding protein receptor mRNA, as described in further detail below. Similarly, the activity of a retinoic acid synthesis enzyme may be blocked by reducing expression of the enzyme, by use of antisense compounds, etc.

As used herein, in general, the term "antagonist" includes but is not limited to agents such as an atom or molecule, wherein a molecule may be inorganic or organic, a biological effector molecule and/or a nucleic acid encoding an agent such as a biological effector molecule, a protein, a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid and a carbohydrate. An agent may be in solution or in suspension (e.g., in crystalline, colloidal or other particulate form). The agent may be in the form of a monomer, dimer, oligomer, etc, or otherwise in a complex.

The terms "antagonist" and "agent" are also intended to include, a protein, polypeptide or peptide including, but not limited to, a structural protein, an enzyme, a cytokine (such as an interferon and/or an interleukin) an antibiotic, a polyclonal or monoclonal antibody, or an effective part thereof, such as an Fv fragment, which antibody or part thereof may be natural, synthetic or humanised, a peptide hormone, a receptor, a signalling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g. a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. Small molecules, including inorganic and organic chemicals, which bind to and occupy the active site of the polypeptide thereby making the catalytic site inaccessible to substrate such that normal biological activity is prevented, are also included. Examples of small molecules include but are not limited to small peptides or peptide-like molecules.

The antagonist or agent may be a protease which cleaves the retinol binding protein receptor or retinoic acid synthesis enzyme. Examples of proteases include aminopeptidase M, carboxypeptidase P, carboxypeptidase Y, caspase 1,4,5, caspase 2,3,7, caspase 6,8,9, chymotrypsin, Factor Xa, pepsin, TEV, thrombin, trypsin etc.

Assays

The present invention also provides a method of screening compounds to identify antagonists of a retinol binding protein receptor. Candidate compounds may be identified from a variety of sources, for example, cells, cell-free preparations, chemical libraries, peptide and gene libraries, and natural product mixtures. Such antagonists or inhibitors so-identified may be natural or modified substrates, ligands, receptors, enzymes, etc., as the case may be, of the retinol binding protein receptor; or may be structural or functional mimetics thereof (see Coligan et al., *Current Protocols in Immunology* 1(2):Chapter 5 (1991)).

The screening method may simply measure the binding of a candidate compound to the retinol binding protein receptor, or to cells or membranes bearing the retinol binding protein receptor, or a fusion protein thereof by means of a label directly or indirectly associated with the candidate compound. Alternatively, the screening method may involve competition with a labeled competitor. Further, these screening methods may test whether the candidate compound results in a signal generated by activation or inhibition of the retinol binding protein receptor, using detection systems appropriate to the cells bearing the receptor.

For example, a cell or membrane preparation expressing a retinol binding protein receptor may be contacted with a compound of interest. The ability of the compound to generate a response, i.e., proliferation of the cell, following interaction with the retinol binding protein receptor is then measured. A compound which binds but does not elicit a response identifies that compound as an antagonist. An antagonist compound is also one which binds and produces an opposite response, in other words, reduction of proliferation and optionally induction of differentiation.

Inhibitors of activation are generally assayed in the presence of a known agonist (here, retinol-retinol binding protein complex) and the effect on activation by the agonist by the presence of the candidate compound is observed. Constitutively active polypeptides may be employed in screening methods for inverse agonists or inhibitors, in the absence of an agonist or inhibitor, by testing whether the candidate compound results in inhibition of activity of the retinol binding protein receptor. Further, the screening methods may simply comprise the steps of mixing a candidate compound with a solution containing retinol binding protein receptor, to form a mixture, and determining whether its ability to bind retinol binding protein is reduced. Fusion proteins, such as those made from Fc portion and retinol binding protein receptor, may also be used for high-throughput screening assays to identify antagonists for retinol binding protein receptor function (see D. Bennett et al., *J Mol Recognition*, 8:52-58 (1995); and K. Johanson et al., *J Biol Chem*, 270(16):9459-9471 (1995)).

The invention also provides a method for identifying a compound capable of inhibiting the interaction between a retinol binding protein and a retinol binding protein receptor. The method comprises contacting a retinol binding protein receptor with a candidate compound in the presence of retinol binding protein and determining whether the levels of retinol binding protein binding to the receptor are reduced. A fragment of retinol binding protein receptor capable of binding to retinol binding protein may also be used.

Assays for compounds capable of lowering the endogenous level of retinoic acid in a cell are also provided. Such an assay may involve contacting a cell which expresses a retinol binding protein receptor with a candidate compound in the presence of retinol-retinol binding protein complex and determining whether the level of retinoic acid in said cell is lowered as a result of the contacting.

The invention further provides a method for identifying a compound capable of reducing endogenous retinoic acid levels. The method comprises contacting a cell with a candidate compound, and determining whether the levels of retinoic acid within the cell are reduced. Furthermore, a method which involves exposing a cell expressing a retinol dehydrogenase to a compound and determining whether the levels of retinal within the cell are reduced may be used to identify an inhibitor of retinol dehydrogenase. A method which involves exposing a cell expressing a retinal dehydrogenase to a compound and determining whether the levels of retinoic acid within the cell are reduced may be used to identify an inhibitor of retinal dehydrogenase.

The assays and screening methods may employ a number of candidate compounds, for example, in the form of a library. Combinatorial libraries may also be employed. The libraries, target enzymes, etc, may be set on a solid support, for example, in the form of arrays as known in the art.

A "combinatorial library", as the term is used in this document, is a collection of multiple species of chemical compounds that consist of randomly selected subunits. Combinatorial libraries may be screened for ligands or molecules which bind to the retinol binding protein receptor, which antagonise the retinol binding protein receptor, or which are capable of reducing the endogenous retinoic acid concentration in the cell.

Various combinatorial libraries of chemical compounds are currently available, including libraries active against proteolytic and nonproteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and antiinfective targets, among others. A comprehensive review of combinatorial libraries, in particular their construction and uses is provided in Dolle and Nelson (1999), Journal of Combinatorial Chemistry, Vol 1 No 4, 235-282.

Further references describing chemical combinatorial libraries, their production and use include those available from the Network Science Corporation's on-line journal, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies for Introducing Carbohydrate Molecular Diversity Into The Drug Discovery Process. Mochael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate ligands, molecules, inhibitors or antagonists may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of candidate ligands, candidate ligands, molecules, inhibitors or antagonists may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Immunoglobulins

Immunoglobulin molecules are in the broadest sense members of the immunoglobulin superfamily, a family of polypeptides which comprise the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor).

The methods of the present invention may therefore make use of any immunoglobulin superfamily molecule which is capable of binding to a target to interfere with the interaction of retinol binding protein receptor with its ligand, the retinol-retinol binding protein complex, as well as those capable of binding to a target to interfere with the interaction of a retinoic acid synthesis enzyme and its substrate. Peptides or fragments derived from immunoglobulins may also be used.

Antibodies, as used herein, refers to complete antibodies or antibody fragments capable of binding to a selected target, and including Fv, ScFv, Fab' and F(ab')$_2$, monoclonal and polyclonal antibodies, engineered antibodies including chimeric, CDR-grafted and humanised antibodies, and artificially selected antibodies produced using phage display or alternative techniques. Small fragments, such as Fv and ScFv, possess advantageous properties for diagnostic and therapeutic applications on account of their small size and consequent superior tissue distribution. Preferably, the antibody is a single chain antibody or scFv.

The antibodies may be altered antibodies comprising an effector protein such as a toxin or a label. Use of labelled antibodies allows the imaging of the distribution of the antibody in vivo. Such labels may be radioactive labels or radioopaque labels, such as metal particles, which are readily visualisable within the body of a patient. Moreover, they may be fluorescent labels (such as the ones described here) or other labels which are visualisable on tissue samples removed from patients. Antibodies with effector groups may be linked to any association means as known in the art.

Antibodies may be obtained from animal serum, or, in the case of monoclonal antibodies or fragments thereof, produced in cell culture. Recombinant DNA technology may be used to produce the antibodies according to established procedure, in bacterial, yeast, insect or preferably mammalian cell culture. The selected cell culture system preferably secretes the antibody product.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2× YT, or M9 Minimal Medium, and for yeast in medium YPD, YEPD, Minimal Medium, or Complete Minimal Dropout Medium.

Use of insect cells as hosts for the expression of proteins has advantages in that the cloning and expression process is relatively easy and quick. In addition, there is a high probability of obtaining a correctly folded and biologically active protein when compared to bacterial or yeast expression. Insect cells may be cultured in serum free medium, which is cheaper and safer compared to serum containing medium. Recombinant baculovirus may be used as an expression vector, and the construct used to transfect a host cell line, which may be any of a number of lepidopteran cell lines, in particular *Spodoptera frugiperda Sf*9, as known in the art. Reviews of expression of recombinant proteins in insect host cells are provided by Altmann et al. (1999), *Glycoconj J* 1999, 16, 109-23 and Kost and Condreay (1999), *Curr Opin Biotechnol*, 10, 428-33.

In vitro production provides relatively pure antibody preparations and allows scale-up to give large amounts of the desired antibodies. Techniques for bacterial cell, yeast, insect and mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules is described in the above references and also in, for example, EP 0623679; EP 0368684 and EP 0436597, which are incorporated herein by reference.

The cell culture supernatants are screened for the desired antibodies, preferentially by immunofluorescent staining of cells expressing the desired target by immunoblotting, by an enzyme immunoassay, e.g. a sandwich assay or a dot-assay, or a radioimmunoassay. In particular, the assay used in Bavik et al., 1995, *Experimental Cell Research* 216: 358-362 may be used. This document discloses the isolation of a monoclonal antibody p142 against retinol binding protein receptor, by screening for interference in a retinol binding protein receptor-retinol binding protein receptor binding assay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or immunoaffinity chromatography, e.g. affinity chromatography with the a protein containing a target or with Protein-A.

Antibodies generated according to the foregoing procedures may be cloned by isolation of nucleic acid from cells, according to standard procedures. Usefully, nucleic acids variable domains of the antibodies may be isolated and used to construct antibody fragments, such as scFv.

The invention therefore preferably employs recombinant nucleic acids comprising an insert coding for a heavy chain variable domain and/or for a light chain variable domain of antibodies. By definition such nucleic acids comprise coding single stranded nucleic acids, double stranded nucleic acids consisting of said coding nucleic acids and of complementary nucleic acids thereto, or these complementary (single stranded) nucleic acids themselves.

Furthermore, nucleic acids encoding a heavy chain variable domain and/or for a light chain variable domain of antibodies can be enzymatically or chemically synthesised nucleic acids having the authentic sequence coding for a naturally-occurring heavy chain variable domain and/or for the light chain variable domain, or a mutant thereof. A mutant of the authentic sequence is a nucleic acid encoding a heavy chain variable domain and/or a light chain variable domain of the above-mentioned antibodies in which one or more amino acids are deleted or exchanged with one or more other amino acids. Preferably said modification(s) are outside the CDRs of the heavy chain variable domain and/or of the light chain variable domain of the antibody. Such a mutant nucleic acid is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly yeast, bacterial or mammalian cells, to obtain an optimal expression of the heavy chain variable domain and/or a light chain variable domain.

The term mutant is intended to include a DNA mutant obtained by in vitro or in vivo mutagenesis of DNA according to methods known in the art.

Recombinant DNA technology may be used to improve the antibodies of the invention. Thus, chimeric antibodies may be constructed in order to decrease the immunogenicity thereof in diagnostic or therapeutic applications. Moreover, immunogenicity may be minimised by humanising the antibodies by CDR grafting (European Patent Application 0 239 400 (Winter)) and, optionally, framework modification (EP0239400, as reviewed in international patent application WO 90/07861 (Protein Design Labs)).

The invention therefore also employs recombinant nucleic acids comprising an insert coding for a heavy chain variable domain of an antibody fused to a human constant domain γ, for example γ1, γ2, γ3 or γ4, preferably γ1 or γ4. Likewise the invention concerns recombinant DNAs comprising an insert coding for a light chain variable domain of an antibody fused to a human constant domain κ or λ, preferably κ.

More preferably, the invention employs CDR-grafted antibodies, which are preferably CDR-grafted light chain and heavy chain variable domains only. Advantageously, the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule. Such antibodies are known as scFvs.

Antibodies may moreover be generated by mutagenesis of antibody genes to produce artificial repertoires of antibodies. This technique allows the preparation of antibody libraries, as discussed further below; antibody libraries are also available commercially. Hence, the present invention advantageously employs artificial repertoires of immunoglobulins, preferably artificial ScFv repertoires, as an immunoglobulin source.

Isolated or cloned antibodies may be linked to other molecules, for example nucleic acid or protein association means by chemical coupling, using protocols known in the art (for example, Harlow and Lane, Antibodies: a Laboratory Manual, (1988) Cold Spring Harbor, and Maniatis, T., Fritsch, E. F. and Sambrook, J. (1991), Molecular Cloning: A Laboratory Manual. Cold Spring Harbor, N.Y., Cold Spring Harbor Laboratory Press).

Immunoglobulins may be selected for ability to bind antigens within the intracellular environment. Such "intrabodies" may be designed by for example the intracellular expression of antibodies or antibody fragments (Cochet, et al. (1998), *Cancer Res* 58, 1170-6). Furthermore, selection methods may be employed which directly identify antibodies capable of binding intracellularly to antigens, such as an in vivo two-hybrid system for selecting antibodies with binding capability inside mammalian cells. Such a method is described in United Kingdom application number 9905510.5 and International Patent Application number PCT/GB00/00876.

Antisense Compounds

As described above, the antagonist may comprise one or more antisense compounds, including antisense RNA and antisense DNA, which are capable of reducing the endogenous level of retinoic acid within a relevant cell. Thus, an antagonist capable of lowering the level of expression of the retinol binding protein receptor, or of any retinoic acid synthesis enzyme, in the hyperproliferative cell, such that endogenous retinoic acid levels are reduced, is included. Preferably, the antisense compounds comprise sequences complementary to the retinol binding protein receptor or a retinoic acid synthesis enzyme, for example, a retinol dehydrogenase or a retinal dehydrogenase mRNA.

Preferably, the antisense compounds are oligomeric antisense compounds, particularly oligonucleotides. The antisense compounds preferably specifically hybridize with one or more nucleic acids encoding retinol binding protein receptor or a retinoic acid synthesis enzyme (including retinol dehydrogenase and retinal dehydrogenase). As used herein, the term "nucleic acid encoding retinol binding protein receptor" encompasses DNA encoding retinol binding protein receptor, RNA (including pre-mRNA and mRNA) transcribed from such DNA, and also cDNA derived from such RNA. Similarly, the term "nucleic acid encoding a retinoic acid synthesis enzyme" encompasses DNA encoding a retinoic acid synthesis enzyme (including retinol dehydrogenase and retinal dehydrogenase), RNA (including pre-mRNA and mRNA) transcribed from such DNA, and also cDNA derived from such RNA.

The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of retinol binding protein receptor or a retinoic acid synthesis enzyme (including retinol dehydrogenase and retinal dehydrogenase). In the context of the present invention, "modulation" means either an increase (stimulation) or a decrease (inhibition) in the expression of a gene. For example, the expression of a gene encoding an inhibitor of retinol binding protein receptor or retinoic acid synthesis enzyme activity, or an inhibitor of expression of retinol binding protein receptor or the enzyme, may be increased. However, preferably, inhibition of expression, in particular, inhibition of retinol binding protein receptor or retinoic acid synthesis enzyme expression, is the preferred form of modulation of gene expression and mRNA is a preferred target.

Antisense constructs are described in detail in U.S. Pat. No. 6,100,090 (Monia et al), and Neckers et al., 1992, *Crit Rev Oncog* 3(1-2):175-231, the teachings of which document are specifically incorporated by reference.

Skin Hyperproliferative Diseases

Skin hyperproliferation diseases which may be treated by using the methods and compositions of our invention include psoriasis, acne vulgaris, acne rosacea, actinic keratosis (solar keratoses—squamous carcinoma in situ), the ichthyoses, hyperkeratoses, disorders of keratinization such as Darriers disease, palmoplanter keratodermas, pityriasis rubra pilaris, epidermal naevoid syndromes, erythrokeratoderma variabilis, epidermolytic hyperkeratoses, non-bullous ichthyosiform erythroderma, cutaneous lupus erythematosus and lichen planus.

According to our invention, a patient exhibiting any of the symptoms associated with a skin hyperproliferative disease, for example, a disease as listed above, is treated with a blocking agent or antagonist to reduce the activity of retinol binding protein receptor or a retinoic acid synthesis enzyme (including retinol dehydrogenase and retinal dehydrogenase). Alternatively or in addition, the endogenous retinoic acid levels within hyperproliferative cells in the diseased patient are reduced. Such treatment leads to reduction on proliferation of the diseased cells. The blocking agent, etc, may be applied to a patient on its own, on in the form of a pharmaceutical composition as described in more detail below. The effect of treatment of a host with skin proliferation disease may be evaluated by objective criteria such as an improvement of desquamation and erythema, reduction of the size of lesions as well as subjective criteria such as cessation of itching.

In particular, the compositions and methods of our invention are suitable for the treatment or alleviation of symptoms of psoriasis. Psoriasis manifests itself as inflamed swollen skin lesions covered with silvery white scale. Characteristics of psoriasis include pus-like blisters (pustular psoriasis), severe sloughing of the skin (erythrodermic psoriasis), drop-like dots (guttate psoriasis) and smooth inflamed lesions (inverse psoriasis).

The causes of psoriasis are currently unknown, although it has been established as an autoimmune skin disorder with a genetic component. One in three people report a family history of psoriasis, but there is no pattern of inheritance. However, there are many cases in which children with no apparent family history of the disease will develop psoriasis. Whether a person actually develops psoriasis may depend on "trigger factors" which include systemic infections such as strep throat, injury to the skin (the Koebner phenomenon), vaccinations, certain medications, and intramuscular injections or oral steroid medications. Once something triggers a person's genetic tendency to develop psoriasis, it is thought that in turn, the immune system triggers the excessive skin cell reproduction.

Skin cells are programmed to follow two possible programs: normal growth or wound healing. In a normal growth pattern, skin cells are created in the basal cell layer, and then move up through the epidermis to the stratum corneum, the outermost layer of the skin. This normal process takes about 28 days from cell birth to death. When skin is wounded, a wound healing program (regenerative maturation) is triggered, in which cells are produced at a much faster rate, the blood supply increases and localized inflammation occurs. Lesional psoriasis is characterized by cell growth in the alternate growth program. Skin cells (keratinocytes) switch from the normal growth program to regenerative maturation, cells are created and pushed to the surface in as little as 2-4 days, and the skin cannot shed the cells fast enough. The excessive skin cells build up and form elevated, scaly lesions. The white scale ("plaque") that usually covers the lesion is composed of dead skin cells, and the redness of the lesion is caused by increased blood supply to the area of rapidly dividing skin cells.

Psoriasis is a genetically determined disease of the skin characterized by two biological hallmarks. First, there is a profound epidermal hyperproliferation related to accelerated and incomplete differentiation. Second, there is a marked inflammation of both epidermis and dermis with an increased recruitment of T lymphocytes, and in some cases, formation of neutrophil microabcesses. Many pathologic features of psoriasis can be attributed to alterations in the growth and maturation of epidermal keratinocytes, with increased proliferation of epidermal cells, occurring within 0.2 mm of the skin's surface. Traditional investigations into the pathogenesis of psoriasis have focused on the increased proliferation and hyperplasia of the epidermis. In normal skin, the time for a cell to move from the basal layer through the granular layer is 4 to 5 weeks. In psoriatic lesions, the time is decreased sevenfold to tenfold because of a shortened cell cycle time, an increase in the absolute number of cells capable of proliferating, and an increased proportion of cells that are actually dividing. The hyperproliferative phenomenon is also expressed, although to a substantially smaller degree, in the clinically uninvolved skin of psoriatic patients.

A common form of psoriasis, psoriasis vulgaris, is characterized by well-demarcated erythematous plaques covered by thick, silvery scales. A characteristic finding is the isomorphic response (Koebner phenomenon), in which new psoriatic lesions arise at sites of cutaneous trauma.

Lesions are often localized to the extensor surfaces of the extremities, and the nails and scalp are also commonly involved. Much less common forms include guttate psoriasis, a form of the disease that often erupts following streptococcal pharyngitis, and pustular psoriasis, which is characterized by numerous sterile pustules, often 2 to 5 mm in diameter, on the palms and soles or distributed over the body.

Our methods and compositions are also suitable for the treatment of acne. Acne affects large patient populations and is a common inflammatory skin disorder which usually localizes on the face. Fortunately, the disease usually disappears and in the interval of months or years between onset and resolution, therapy, although not curative, can satisfactorily suppress the disease in the majority of patients.

A small number of acne patients with severe disease show little or no response to intensive therapeutic efforts including the use of high doses of oral tetracycline, dapsone, prednisone, and, in women, estrogen. In many cases, these drugs afford only a modest degree of control while the side effects of these agents severely restrict their usefulness. Patients with nodulocystic acne suffer from large, inflammatory, suppurative nodules appearing on the face, and frequently the back and chest. In addition to their appearance, the lesions are tender and often purulently exudative and hemorrhagic. Disfiguring scars are frequently inevitable.

Therapies for acne involve local and systemic administration of retinoids. Topical application of all-trans-retinoic acid (tretinoin) has been tried with some success, particularly against comedones or blackheads, but this condition frequently returns when the treatment is withdrawn.

Objective methods which are employed for establishing the effect of treatment of psoriasis patients include the resolution of plaques by visual monitoring and with photography. The visual scoring is done using PASI (Psoriasis Area and Severity Index) score (see Fredericksson, A J, Peterssonn B C Dermatologies 157:238-244 (1978)).

Neoplasms and Cancer

The methods and compositions of our invention may be used for inhibiting the proliferation and optionally reversing the transformed phenotype of hyperproliferative cancer cells.

Retinoids have been shown experimentally to effect tumour development and growth by several mechanisms including, influencing carcinogen activation, growth factors, angiogenesis, collagenase production and modifying the host immune response (Gollnick 1997, *Retinoids* 13, 6-12). In vitro retinoic acid has been shown to induce differentiation and/or inhibit clonal expansion of several tumour cell lines including human acute myeloid leukaemia, neuroblastoma, teratocarcinoma, melanoma and rat rhabdomyosarcoma cells (Smith et al., 1992, *Journal of Clinical Oncology* Vol 10, 839-864). The most responsive cells to retinoic acid induced differentiation are promyelocytic leukaemic cells (Smith et al., 1992 *Journal of Clinical Oncology* Vol 10, 839-864.). The synthetic oral retinoids isotretinoin, etretinate and acetretin and topical isotretinoin and retinoic acid have been shown in controlled clinical trials to induce resolution of pre-malignant and some malignant non-melanocytic skin cancers (Gollnick 1997, *Retinoids* 13, 6-12; Kraemer et al., 1988, *N Engl J Med* 318, 1633-7). Etretinate and acitretin have been shown to reduce the growth of small basal cell carcinomas (BCC) and prevent new BCC lesions developing in individuals with the Gorlin-Goltz syndrome (Goldberg et al., 1989, *J Am Acad Dermatol* 21, 144-5.). Oral and topical retinoids have been shown to reduce the number/prevent progression of pre-cancerous actinic keratoses and bowenoid keratoses (Meyskens et al., 1986, *J Am Acad Dermatol* 15, 822-5; Moriarty et al., 1982, *Lancet* 1, 364-5.) and to treat established squamous cell carcinomas (Levine et al., 1989, *Arch Dermatol* 125, 1225-30). The topical application of TRA (all-trans retinoic acid) has also produced resolution of dysplastic naevi in a half-sided study (Meyskens et al., 1986, *J Am Acad Dermatol* 15, 822-5).

The most responsive haematological malignancy to retinoid therapy is acute promyelocytic leukaemia (APL) in which retinoids can induce complete remission without a period of bone marrow aplasia (Stone et al., 1988, *Blood* 71, 690-696.; Wallace, 1989, *Am J Hematol* 31, 266-268). In patients with an excised head and neck squamous cell carcinomas oral retinoids have been shown to reduce the development of second epithelial tumours, 4% compared to 24% in placebo treated group (Smith et al., 1992, *Journal of Clinical Oncology* Vol 10, 839-864). Regression of advanced cervical squamous cell carcinoma has been induced by a combination of retinoic acid and IFN-alpha (Lippman et al., 1992, *J Natl Cancer Inst* 81, 241-245). Retinoids have also been shown to be effective in animal models of other solid tumours including breast, prostate and bladder (Smith et al., 1992, *Journal of Clinical Oncolog.* Vol 10, 839-864; Whelan, 1999, *Eur Urol* 35, 424-428). However existing retinoid therapy is limited by the substantial toxicities that result from activation of multiple signalling pathways (Singh and Lippman, 1998, *Oncology* 12, 1643-1659).

Although the most effective use of retinoids has been in the prevention of tumours rather than treatment of established lesions (Bollag and Holdener, 1992, *Annals of Oncology* 3, 513-526.; Kemmett and Hunter, 1988, *Hospital Update*. March 1988, pp 1301-1313; Shi-Yong and Lotan, 1988, *Drugs of the Future* 23, 621-634.), our methods and compositions may be used both for prevention and for treatment.

Thus, any of the above conditions may be treated or alleviated by the methods and compositions described here. In particular, the methods and compositions described are useful for treating any tumour, carcinoma, etc, which has been treated successfully or unsuccessfully with retinoid therapy. The methods and compositions are also useful to treat pre-malignant conditions i.e. to prevent their progression to actual malignancy. Reduction in endogenenous retinoic acid levels inhibits angiogenesis, and therefore such reduction may be used to prevent the spread of tumours. In particular, such reduction in endogenous retinoic acid levels may be achieved by antagonising the retinol binding protein receptor, preferably in such a way as to prevent retinol binding protein and/or retinol uptake. Reduction in endogenous retinoic acid levels may also be achieved by inhibiting or preventing synthesis of retinoic acid, by for example, inhibiting a retinoic acid synthesis enzyme as described elsewhere in this document. Specific examples of tumours include melanocytic naevus and mrelodysplastic syndrome.

The methods of our invention include the administration of an antineoplastic agent to a patient suffering from a hyperproliferative disease such as cancer. This may involve a step of contacting pathological or non-pathological hyperproliferative cells with an effective amount of an agent capable of reducing endogenous retinoic acid levels, including a retinol binding protein receptor antagonist, or a retinoic acid synthesis enzyme antagonist, to reduce proliferation of the hyperproliferative cells. An example is use of an antibody against retinol binding protein receptor.

The present method can be performed on cells in culture, e.g., in vitro or ex vivo, or can be performed on cells present in an animal subject, e.g., as part of an in vivo therapeutic protocol. The therapeutic regimen can be carried out on a human or other animal subject. The terms "antineoplastic agent" and "antiproliferative agent" are used interchangeably herein and includes agents that have the functional property of inhibiting the proliferation of a hyperproliferative cell, e.g., inhibit the development or progression of a neoplasm.

Any agent which is capable of reducing endogenous retinoic acid levels, for example, by blocking the activity of retinol binding protein receptor or by inhibiting a retinoic acid synthesis enzyme (including retinol dehydrogenase and retinal dehydrogenase) may be used in the methods and compositions according to our invention. Preferably, therapeutically effective anti-neoplastic amount of such an agent is used, i.e., an amount of an agent which is effective, upon single or multiple dose administration to the patient, in inhibiting the growth of a neoplastic cells, or in prolonging the survivability of the patient with such neoplastic cells beyond that expected in the absence of such treatment. As used herein, "inhibiting the growth" of the neoplasm includes the slowing, interrupting, arresting or stopping its growth and metastases and does not necessarily indicate a total elimination of the neoplastic growth. The agent may also be used as a prophylactic, in a prophylactically effective anti-neoplastic amount, i.e., an amount which is effective, upon single or multiple dose administration to the patient, in preventing or delaying the occurrence of the onset of a neoplastic disease state. Particular cancers which are treatable with the methods and compositions of our invention include basal cell carcinoma, squamous cell carcinoma, and dysplastic naevi, malignant melanoma. It will be appreciated that photoaged cells, as well as many skin proliferative diseases, may exhibit many of the properties of pre-malignant cancer cells, and our invention may also usefully be employed in treatment of such cells.

The common medical meaning of the term "neoplasia" refers to "new cell growth" that results as a loss of responsiveness to normal growth controls, e.g. to neoplastic cell growth. A "hyperplasia" refers to cells undergoing an abnormally high rate of growth. However, as used herein, the terms neoplasia and hyperplasia can be used interchangably, as their context will reveal, referring generally to cells experiencing abnormal cell growth rates. Neoplasias and hyperplasias include "tumors," which may be either benign, premalignant or malignant.

The agents, including retinol binding protein receptor antagonists, of the invention may be tested initially in vitro for their inhibitory effects in the proliferation of neoplastic cells. Examples of cell lines that can be used are transformed cells, e.g., the human promyeloid leukemia cell line HL-60, and the human myeloid leukemia U-937 cell line (Abe E. et al. (1981) *Proc. Natl. Acad. Sci.* USA 78:4990-4994; Song L. N. and Cheng T. (1992) *Biochem Pharmacol* 43:2292-2295; Zhou J. Y. et al. (1989) *Blood* 74:82-93; U.S. Pat. Nos. 5,401,733, 5,087,619). Alternatively, the antitumoral effects of such an agent can be tested in vivo using various animal models known in the art and summarized in Bouillon, R. et al. (1995) *Endocrine Reviews* 16(2):233 (Table E), which is incorporated by reference herein. For example, SL mice are routinely used in the art as models for MI myeloid leukemia (Honma et al. (1983) *Cell Biol.* 80:201-204; Kasukabe T. et al. (1987) *Cancer Res.* 47:567-572); breast cancer studies can be performed in, for example, nude mice models for human MX1 (ER) (Abe J. et al. (1991) Endocrinology 129:832-837; other cancers, e.g., colon cancer, melanoma osteosarcoma, can be characterized in, for example, nude mice models as describe in (Eisman J. A. et al. (1987) *Cancer Res.* 47:21-25; Kawaura A. et al. (1990) *Cancer Lett* 55:149-152; Belleli A. (1992) *Carcinogenesis* 13:2293-2298; Tsuchiya H. et al. (1993) J *Orthopaed Res.* 11:122-130).

In certain embodiments, the agents or antagonists can be used in combinatorial therapy with conventional cancer chemotherapeutics. Conventional treatment regimens for tumors include radiation, drugs, or a combination of both. In addition to radiation, the following drugs, usually in combinations with each other, are often used to treat acute tumours: vincristine, prednisone, methotrexate, mercaptopurine, cyclophosphamide, and cytarabine. In chronic leukemia, for example, busulfan, melphalan, and chlorambucil can be used in combination. All of the conventional anti-cancer drugs are highly toxic and tend to make patients quite ill while undergoing treatment. Vigorous therapy is based on the premise that unless every cancerous cell is destroyed, the residual cells will multiply and cause a relapse.

The subject method can also be useful in treating malignancies of the various organ systems, such as affecting lung, breast, lymphoid, gastrointestinal, and genitourinary tract as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

According to the general paradigm that reducing endogenous retinoic acid levels by blocking retinol binding protein receptor activity or by inhibiting a retinoic acid synthesis enzyme (including retinol dehydrogenase and retinal dehydrogenase) leads to reduction of proliferation of transformed cells, exemplary solid tumors that can be treated according to the method of the present invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Determination of a therapeutically effective anti-neoplastic amount or a prophylactically effective anti-neoplastic amount of the antagonist can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective anti-neoplastic amount or dose, and the prophylactically effective antineoplastic amount or dose, a number of factors are considered by the attending clinician, including, but not limited to: the specific hyperplastic/neoplastic cell involved; pharmacodynamic characteristics of the particular agent and its mode and route of administration; the desirder time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the agents used with other co-administered therapeutics); and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired. Compounds which are determined to be effective for the prevention or treatment of tumors in animals, e.g., dogs, rodents, may also be useful in treatment of tumors in humans. Those skilled in the art of treating tumor in humans will know, based upon the data obtained in animal studies, the dosage and route of administration of the compound to humans. In general, the dosage and route of administration in humans is expected to be similar to that in animals. Further considerations relating to dosage are discussed below.

The identification of those patients who are in need of prophylactic treatment for hyperplastic/neoplastic disease states is well within the ability and knowledge of one skilled in the art. Certain of the methods for identification of patients which are at risk of developing neoplastic disease states which can be treated by the subject method are appreciated in the medical arts, such as family history of the development of a particular disease state and the presence of risk factors associated with the development of that disease state in the subject patient. The present invention also includes other prognostic tests which can be used to make, or to augment a clinical predication about the use of the method of the present invention. A clinician skilled in the art can readily identify such candidate patients, by the use of, for example, clinical tests, physical examination and medical/family history.

Photoageing

The alterations in the structural and functional components of the skin as a result of prolonged exposure to ultraviolet radiation are collectively referred to as photodamage, dermatoheliosis or photoageing.

The smooth elastic properties of normal skin are maintained by the water retaining barrier provided by the epidermis (Cork, 1997, *J. Dermatol. Treat* 8, S7-S13.) and the support by structural fibrillar proteins, collagen and elastin in the dermis. Chronic exposure to ultraviolet radiation results in macroscopic and microscopic changes in the skin, which are termed photoageing (Gilchrest, 1992, *Br J Dermatol* 127 Suppl 41, 14-20). The clinical features of photoaged or photodamaged skin include fine and course wrinkles, pigmentary changes, age spots (actinic lentigines), laxity, roughness, sallowness, mottled hyperpigmentation, telangiectasia (prominent fine blood vessels) and several benign, premalignant and malignant neoplasms. These can have a significant impact on certain aspects of quality of life (Gupta & Gupta, 1996, *Journal of Dermatological Treatment*; Griffiths et al., 1993; Griffiths, 1992, 7, 261-264). Histologically the epidermis is thickened initially, becoming atrophic in the later stages, with keratinocyte atypia and dysplasia. Dermal elastosis and increased melanocyte activity are also observed. Dysplastic and neoplastic changes such as actinic keratoses and basal and squamous cell carcinomas are also extreme features of photodamaged skin. The dermis contains an increased number of elastic fibres that are thickened and degraded in a disorganised mass and decreased collagen. The dermal blood vessels are dilated and tortuous (Fisher et al., 1996, *Nature* 379, 335-339).

Several double blind clinical trials have demonstrated that 0.05% tretinoin can reduce the clinical and histological features of photoageing (Olsen et al., 1992, *J. Am. Acad. Dermatol.* 26, 215-224; Weinstein et al., 1991, *Arch Dermatol* 127, 659-65). After application of tretinoin the epidermis thickens and irregularly sized, shaped and stained cells with oddly shaped nuclei give way to healthier looking keratinocytes (Kligman and Graham, 1993, *J. Dermatol. Treat.* 4, 113-117; Kligman and Leyden, 1993, *Skin Pharmacol* 6, 78-82). These changes are a result of the 'pushing' of the keratinocytes into a more normal pattern of differentiation (Marks, 1996). Supporting this hypothesis retinoids have been shown to produce rapid clearance of premalignant actinic keratoses (Gilchrest, 1992, *Br J Dermatol* 127 Suppl 41, 14-20; Moriarty et al., 1982, *Lancet* 1, 364-5).

Although ageing has been thought to be irreversible, studies made during the last decade have shown that some topical compounds and surgical procedures can improve age-related skin damage (Griffiths et al., 1995, *Archives of Dermatology* 131, 1037-1044; Roger & Fuleihan, 1995, *Face lift and adjunctive procedures in the treatment of photodamaged skin*. In *Photodamage*. Gilchrest B A ed. 1995; Blackwell Science, 259-285.; Pierard et al., 1996, *Maturitas* 23, 273-277; Pierard et al 1997, *Dermatology* 194, 398-401). Drug treatment consists of sunscreens, retinoids, antioxidants including vitamin C and E and beta-carotene, alpha-hydroxyacids and oestrogen (Humphreys et al., 1996, *Journal of American Academy of Dermatology* 34, 638-644.; Thibault et al., 1998, *Dermatology Surgery* 24, 573-577; Weiss et al 1988, *JAMA* 259, 527-532.). A variety of topical prescription and nonprescription agents are widely available for improving photodamaged skin, the efficacy of which is unclear. Topical retinoic acid treatment results in the increased synthesis of collagens in the dermis and effacement of wrinkles (Griffiths et al., 1993, *New England Journal of Medicine* 329, 530-535; Kligman, 1987, *J Invest Dermatol* 88, 12s-17s; Kligman et al., 1984, *Connect Tissue Res* 12, 139-50). Application of retinoic acid also produces a deposition of linear elastic fibres replacing the tortuous elastic fibres produced by UV irradiation (Tsukahara et al., 1999, *Br J Dermatol* 140, 1048-1053).

The effects of topical and oral retinoids on photoaged skin therefore appear to involve a modification of the differentiation program of keratinocytes and fibroblasts. Currently the use of retinoids in the treatment and prevention of photoageing is limited by their adverse effects, principally teratogenicity and cutaneous irritation. Cultures of fibroblasts have been used to demonstrate that retinoic acid causes an increased production of collagen and elastin in vitro (Tajima et al., 1997, *J Dermatol Sci* 15, 166-7). The effects of retinoic acid on keratinocyte differentiation/proliferation in vitro have been studied by quantifying the production of keratins (Fuchs and Green, 1981, *Cell* 25, 617-25; Kim et al., 1984, *Proc. Natl. Acad. Sci.* 81, 4280-4284).

The methods and compositions of our invention may be used to treat photoageing in a patient, or to alleviate its symptoms. We have found that reducing the endogenous level of retinoic acid within cells of a patient suffering from photoageing produces histological and clinical improvement in phtodamaged or photoaged skin. Furthermore, these improvements may also be achieved by administration of agents which block the activity of retinol binding protein receptor ("blocking agents") and/or of retinol binding protein receptor antagonists or of inhibitors of retinoic acid synthesis enzymes (including retinol dehydrogenase and retinal dehydrogenase).

Thus, the blocking agents and/or antagonists when applied topically to the skin, reverse the condition associated with photodamage so as to moderate and retard the damage to the skin caused by sun exposure. The damage caused sun exposure may include premature aging, elastosis and wrinkling or other symptoms as described earlier. This damage is more pronounced in older patients. By applying the blocking agents and/or antagonists topically to the skin in an amount effective to reverse the conditions associated with photodamage, the acceleration of skin repair is accomplished to enhance the skin with a smoother and younger appearance. The blocking agents and/or antagonists should be applied to that portion or area of the skin which is affected by photodamage or in which treatment is desired. The use of the blocking agents and/or antagonists in accordance with this invention can provide the effects of anti-aging and anti-wrinkling, as well as enhance the repair of sun damaged skin.

The blocking agents and/or antagonists can be applied in accordance with this invention to human skin in conventional topical compositions, as described elsewhere. These compositions can be utilized to apply blocking agents and/or antagonists to the skin of the body, particularly the face, legs, arms and hands. The preferred method of application of blocking agents and/or antagonists topically to produce the best effects should start where a patient is between 30 and 55 years of age, when elastosis begins to appear and becomes more pronounced.

Thereafter, this composition can be continuously applied to patients to reduce the effects and injury associated with sun exposure. Generally, it is preferred to begin the treatment when the patient reaches approximately 30 years of age and to continue the treatment throughout his life, in order that the effects of elastosis be reduced and to prevent any further progression of photodamage.

The blocking agents and/or antagonists can be administered in accordance with this invention in any conventional suitable topical preparation, that is, in combination with any suitable conventional carrier useful for topical administration, as described in further detail elsewhere in this document. Therefore, blocking agents and/or antagonists can be administered in accordance with this invention in any suitable topical composition such as a cream, ointment, soap, solution, lotion, emulsion, shampoo, and the like. Generally, for most efficacious results, these topical compositions contain from about 0.01% to about 0.1% by weight of the total composition of a blocking agent and/or antagonist, with amounts of from about 0.1% to about 0.01% by weight of the composition being especially preferred. If desired, higher concentrations may be utilized depending upon the nature and extent of elastosis.

In formulating these compositions, any conventional non-toxic, dermatologically acceptable base or carrier in which the blocking agent(s) and/or antagonist(s) is stable can be utilized. The preferred compositions for use in this invention are the conventionally cosmetic compositions which can contain a cosmetically active ingredient which is topically administered to human skin to provide a cosmetic effect. Among the conventional cosmetically active materials which can be utilized in this composition are included: sunscreens, penetration enhancers, moisturizers, surfactants, emollient, colorants, conditioners, bacteriocides, astringents, detergents, and the like. The topical compositions of this invention can, if desired, contain suitable sunscreen agents. Any conventional sunscreen agent can be utilized in formulating the formulations containing blocking agents and/or antagonists which can be utilized in accordance with this invention.

These topical compositions which contain blocking agents and/or antagonists can contain any of the conventional excipients and additives commonly used in preparing topical compositions. Among the conventional additives or excipients, which can be utilized in preparing these cosmetic compositions in accordance with this invention are preservatives, thickeners, perfumes and the like. In addition, the conventional antioxidants, such as butylated hydroxyanisoles (BHA), ascorbyl palmitate, propyl gallate, citric acid, butylated hydroxy toluene (BHT), ethoxyquin, tocopherol, and the like can be incorporated into these compositions. These topical compositions can contain conventional acceptable carriers for topical applications which are generally utilized in these compositions. These compositions may contain thickening agents, humectants, emulsifying agents and viscosity stabilizers, such as those generally utilized. In addition, these compositions can contain flavoring agents, colorants, and perfume which are conventional in preparing cosmetic compositions. Other components which may be included in the composition are described elsewhere in this document.

The topical compositions containing blocking agents and/or antagonists can be applied to the skin and should be preferably applied once daily to the skin. For obtaining the reversal of the elastosis so as to impart to the skin a smooth and younger appearance, the topical compositions should be preferably applied for a period of 6 months. After that, compositions which contain blocking agents and/or antagonists should be applied continually to maintain the effect of younger and smoother skin. These preparations can be applied according to the need of the patient as determined by the prescribing physician. In any event, the particular regimen for application of this composition to a patient will typically depend on the age, weight and skin condition of the individual.

The UVB irradiated hairless mouse has been found to be a convenient model for actinic elastosis in the skin. (Kligman et al. J. Invest. Dermatol. 78:181 (1982). It has been shown by Johnston et al. in J. Invest. Dermatol. 82:587 (1984) that irradiation with low levels of UVB which simulate realistic solar exposure leads to a significant increase in skin elastin as measured by desmosine content. The amount of this amino acid, which is isolated from acid hydrolysis of elastin, is proportional to the elastin present in the skin. (Uitto et al., Lab. Invest. 49:1216 (1973). Treatment of irradiated mice with topical retinoic acid has been shown to normalize the histological features of the skin in which the previously elastoic dermis has the appearance of unirradiated tissue (Kligman et al., Conn. Tissue Res. 12:139 (1984), Kligman U.S. Pat. No. 4,603,146 July 1986). Therefore, this model can be used to determine the efficacy of compounds in the repair of sun damaged skin.

Assessment of the efficacy of treatment on humans may be made by any method conventionally known and accepted by the medical profession. This may include subjective assessment by a clinician of the symptoms of photoageing, for example. Wrinkling or roughness of the skin may be measured using optical profilometry of silicone casts of areas of interest, for example the crow's foot region of the facial skin. Clinical measurements of skin, such as the face and wrinkling of the hands, may also be made. In addition, objective measurements of skin thickness may be made by using a pulsed A-scan ultrasound device. These and other methods of assessing photoageing are reviewd in Craven et al., 1996, *J. Derm. Treatment* 7, Supplement 2, S23-S27.

Other Indications

The methods and compositions of our invention are useful for treating other ailments, conditions and diseases besides skin hyperproliferative diseases, cancer and photoageing.

Other indications which may be treated or alleviated by the methods and compositions disclosed here include any viral disease. Retinoids are known to have an antiviral effect of retinoids, and some cutaneous viral diseases such as human papilloma virus (HPV) induced warts are retinoid response. The HPV genome is known to contain retinoid responsive elements; accordingly, the methods and compositions disclosed here may be used to treat any viral disease, including HPV, lentiviral infection, cytomegalo virus, Epstein-Barr virus (BZLF1), adenovirus, human immunodeficiency virus (HIV), herpes simplex virus (HSV), or hepatitis virus (for example, hepatitis B virus or hepatitis C virus) infection.

For example, the methods and compositions described can be used for treatment of post-operative scarring, including treatment of hypertrophic and keloid scarring. Furthermore, the methods and compositions may be used for the stimulaton of melanogenesis, and for the regulation of pigmentation. Furthermore, reduction of endogenous retinoic acid levels may be used to modulate epidermal barrier function.

Furthermore, particular conditions, diseases, etc which may be treated by the methods and compositions described here are those which are characterised by being or corresponding to side effects of therapeutic administration of retinoids. Thus, current retinoid therapy involves administration of pharmacological concentrations of retinoids, orally or topically, to a patient, leading to a number of unwanted side effects. These side effects can be manifested as conditions in their own right, independent of retinoid therapy.

We have discovered that lowering endogenous retinoic acid levels as set out in this document, for example, by antagonising RBPr to reduce retinol uptake, may be used to treat or alleviate such conditions.

Thus, it is known that oral retinoids inhibit bone growth. Reducing the endogenous retinoic acid level in the patient may be used to affect bone growth positively. The methods and compositions disclosed here may therefore be used as a therapy to enhance bone growth in any condition where bone growth is inhibited. Examples of such conditions include fracture repair and treatment of osteoporosis.

Furthermore, administration of retinoids (for example, orally) can cause hyperlipidaemia. Lowering the endogenous retinoic acid level may be used to lower lipid levels in any condition where high levels of lipid exist. Administration of retinoids can also cause hepatotoxicity, and the methods and compositions disclosed may be employed as a means to effect hepatic repair, for example as a result of cirrhosis or hepatitis infection. Reduction in endogenous retinoic acid levels may be employed to treat, prevent or reverse cutaneous irritation; it is known that retinoids are capable of causing cutaneous irritation when administered, for example, topically. The methods and compositions disclosed in this document may be used to treat or reverse alopecia, which may arise from a variety of causes; oral retinoids are known to cause alopecia. The reduction of endogenous retinoic acid levels may be used to enhance fertility, or as a fertility treatment, as oral retinoids are known to interfere with spermatogenesis and egg implantation, and therefore reduce fertility.

Furthermore, it has been reported that the administration of oral retinoids (for example, isoretinan) as a treatment for acne causes depression and suicide. The methods and compositions disclosed here may therefore be used as a treatment for depression, optionally in combination with other known antidepressives. For example, seasonal affective disorder may be treated this way. Other conditions such as atherosclerosis may be treated, as well as any condition involving inhibition of angiogenesis is also an effect of retinoids.

Pharmaceutical Compositions

The invention also relates to pharmaceutical compositions comprising one or more agents which reduce intracellular retinoic acid levels. These may act by for example blocking the activity of the retinol binding protein receptor ("blocking agents"), and include retinol binding protein receptor antagonists. Furthermore, the activity of a retinoic acid synthesis enzyme (including retinol dehydrogenase and retinal dehydrogenase) may be inhibited to achieve the same effect.

While it is possible for the composition comprising the blocking agent or agents to be administered alone, it is preferable to formulate the active ingredient as a pharmaceutical formulation. The composition may include the blocking agent(s) or retinol binding protein receptor antagonist(s), antagonists of any retinoic acid synthesis enzyme (including retinol dehydrogenase and retinal dehydrogenase antagonists or inhibitors), a structurally related compound, or an acidic salt thereof. The pharmaceutical formulations of the present invention comprise an effective amount of blocking agent or retinol binding protein receptor antagonist, etc together with one or more pharmaceutically-acceptable carriers. An "effective amount" is the amount sufficient to reduce an intracellular retinoic acid level, preferably to enable a cell to cease proliferation and optionally start differentiating, most preferably to alleviate at least one symptom of a skin proliferation disease, a cancer, or photoageing. The effective amount will vary depending upon the particular disease or syndrome to be treated or alleviated, as well as other factors including the age and weight of the patient, how advanced the disease etc state is, the general health of the patient, the severity of the symptoms, and whether the retinol binding protein receptor antagonist or other antagonist or blocking agent is being administered alone or in combination with other therapies.

A pharmaceutical composition may include more than a single inhibitor or antagonist. For example, a combination of two or more inhibitors may be used. Thus, for example, a combination of blocking retinol binding protein receptor and inhibiting a retinoic acid synthesis enzyme, may be formulated in a pharmaceutical composition. Thus, an inhibitor of retinol uptake may be formulated together with an inhibitor of retinol dehydrogenase, or an inhibitor of retinal dehydrogenase, or both. Furthermore, an inhibitor of retinol dehydrogenase may be included in combination with an inhibitor of retinal dehydrogenase. Pharmaceutical compositions may be administered simultaneously or sequentially, for example, in rotation.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The pharmaceutical compositions according to our invention include those suitable for topical and oral administration, with topical formulations being preferred where the tissue affected is primarily the skin or epidermis (for example, psoriasis and other epidermal hyperproliferative diseases, photoageing, skin cancer, etc). The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the retinol binding protein receptor antagonist or blocking agent or retinoic acid synthesis enzyme (including retinol dehydrogenase and retinal dehydrogenase) inhibitor composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p. 1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the retinol binding protein receptor antagonist or blocking agent or retinoic acid synthesis enzyme (including retinol dehydrogenase and retinal dehydrogenase) inhibitor composition in the topical formulation is in an amount of about 0.5 to 50% by weight of the composition, preferably about 1 to 30%, more preferably about 2-20%, and most preferably about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of blocking agent or retinol binding protein receptor antagonist or blocking agent or retinoic acid synthesis enzyme (including retinol dehydrogenase and retinal dehydrogenase) inhibitor must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (*J. Pharm. Sci.*, 60:1175-1179 (1971) demonstrated that in vivo efficacy of topically applied steroids is proportional to the steroid penetration rate into dermatomed human skin in vitro.

A skin penetration enhancer which is dermatologically acceptable and compatible with the blocking agent or retinol binding protein receptor antagonist or inhibitor of a retinoic acid synthesis enzyme (including retinol dehydrogenase and retinal dehydrogenase) can be incorporated into the formulation to increase the penetration of the active compound(s) from the skin surface into epidermal keratinocytes. A skin enhancer which increases the absorption of the active compound(s) into the skin reduces the amount of blocking agent or retinol binding protein receptor antagonist, etc needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, *J. Pharm. Sci.*, 73:1153-1156 (1984)); a combination of ethanol and oleic acid or oleyl alcohol (EP 267,617), 2-ethyl-1,3-hexanediol (WO 87/03490); decyl methyl sulphoxide and Azone (Hadgraft, *Eur. J. Drug. Metab. Pharmacokinet*, 21:165-173 (1996)); alcohols, sulphoxides, fatty acids, esters, Azone, pyrrolidones, urea and polyoles (Kalbitz et al, *Pharmazie*, 51:619-637 (1996)).

Terpenes such as 1,8-cineole, menthone, limonene and nerolidol (Yamane, J. *Pharmacy & Pharmocology*, 47:978-989 (1995)); Azone and Transcutol (Harrison et al, *Pharmaceutical Res.* 13:542-546 (1996)); and oleic acid, polyethylene glycol and propylene glycol (Singh et al, *Pharmazie*, 51:741-744 (1996)) are known to improve skin penetration of an active ingredient.

Levels of penetration of a blocking agent or retinol binding protein receptor antagonist or retinoic acid synthesis enzyme (including retinol dehydrogenase and retinal dehydrogenase) inhibitor composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weanling Yorkshire Pig as an Animal Model for Measuring Percutaneous Penetration. In:Swine in Biomedical Research (M. E. Tumbleson, Ed.) Plenum, N.Y., 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, it is preferable to administer a long acting form of blocking agent or retinol binding protein receptor antagonist or inhibitor of a retinoic acid synthesis enzyme (including retinol dehydrogenase and retinal dehydrogenase) composition using formulations known in the arts, such as polymers. Retinol binding protein receptor antagonist or blocking agent or an inhibitor of a retinoic acid synthesis enzyme (including retinol dehydrogenase and retinal dehydrogenase) can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations of this invention can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

The pharmaceutical composition can be administered in an oral formulation in the form of tablets, capsules or solutions. An effective amount of the oral formulation is administered to patients 1 to 3 times daily until the symptoms of the proliferative disease, cancer or photoageing etc are alleviated. The effective amount of retinol binding protein receptor antagonist or blocking agent or inhibitor of a retinoic acid synthesis enzyme (including retinol dehydrogenase and retinal dehydrogenase) depends on the age, weight and condition of a patient. In general, the daily oral dose of blocking agent or retinol binding protein receptor antagonist inhibitor of a retinoic acid synthesis enzyme (including retinol dehydrogenase and retinal dehydrogenase) is less than 1200 mg, and more than 100 mg. The preferred daily oral dose is about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the blocking agent or retinol binding protein receptor antagonist or inhibitor of a retinoic acid synthesis enzyme (including retinol dehydrogenase and retinal dehydrogenase) composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat skin proliferation disease.

Other therapeutic agents suitable for use herein are any compatible drugs that are effective for the intended purpose, or drugs that are complementary to the formulation. As an example, the treatment with an formulation of this invention can be combined with other treatments such as a topical treatment with corticosteroids, calcipotrine, coal tar preparations, a systemic treatment with methotrexate, retinoids, cyclosporin A and photochemotherapy. The combined treatment is especially important for treatment of an acute or a severe skin proliferation disease. The formulation utilized in a combination therapy may be administered simultaneously, or sequentially with other treatment, such that a combined effect is achieved.

Further Aspects of the Invention

Further aspects of the invention are now set out in the following numbered paragraphs; it is to be understood that the invention encompasses these aspects:

Paragraph 1. A method of treating a patient suffering from a hyperproliferative disorder or photoageing, which method comprises administering to the patient an antagonist of a retinol binding protein receptor (RBPr).

Paragraph 2. A method of treating a patient suffering from a hyperproliferative disorder or photoageing, which method comprises blocking the activity of a retinol binding protein receptor (RBPr) in cells of the patient.

Paragraph 3. A method of treating a patient suffering from a hyperproliferative disorder or photoageing, which method comprises lowering the endogenous level of retinoic acid (RA) in cells of the patient.

Paragraph 4. A method according to Paragraph 2 or 3, in which the method comprises administering to the patient an antagonist of a retinol binding protein receptor (RBPr).

Paragraph 5. A method according to Paragraph 2, 3 or 4, in which the endogenous level of retinoic acid is lowered in a hyperproliferating cell or a cell suffering from photoageing of said patient.

Paragraph 6. A method according to any of Paragraphs 2 to 5, in which the endogenous level of retinoic acid in the cell is lowered to the extent that cell proliferation is reduced or abolished.

Paragraph 7. A retinol binding protein receptor antagonist for use in a method of treatment of a patient suffering from a hyperproliferative disorder or photoageing.

Paragraph 8. An agent capable of lowering the endogenous level of retinoic acid in a cell for use in a method of treating a hyperproliferative disorder or photoageing in a patient.

Paragraph 9. An agent according to Paragraph 8, which is an antagonist of a retinol binding protein receptor (RBPr).

Paragraph 10. A method according to Paragraph 1 or 4, or an agent or antagonist according to Paragraph 7, 8 or 9, which is an immunoglobulin.

Paragraph 11. A method according to Paragraph 1 or 4, or an agent or antagonist according to any of Paragraphs 7 to 10, in which the agent is an antibody capable of binding to retinol binding protein receptor.

Paragraph 12. A method according to Paragraph 1 or 4, or an agent or antagonist according to Paragraph 7, 8 or 9, in which the agent is a peptide comprising a sequence from a receptor binding region of retinol binding protein.

Paragraph 13. A method, agent or antagonist according to Paragraph 12, in which the peptide has a sequence selected from: K29-Q38, G59-A71 and M88-D102 of retinol binding protein and a heterodimer consisting of peptides G59-A71 and M88-D102.

Paragraph 14. A method according to Paragraph 1 or 4, or an agent or antagonist according to Paragraph 7, 8 or 9, which is an antisense compound capable of inhibiting the expression of retinol binding protein receptor.

Paragraph 15. A method, agent or antagonist according to Paragraph 14, which is an antisense RNA or an antisense DNA.

Paragraph 16. A method, agent or antagonist according to Paragraph 14 or 15, which an antisense molecule is a oligonucleotide.

Paragraph 17. A method, agent or antagonist according to any preceding Paragraph, in which the hyperproliferative disorder is psoriasis, acne vulgaris, or cancer.

Paragraph 18. A method for identifying an antagonist of retinol binding protein receptor, the method comprising contacting a cell with expresses retinol binding protein receptor with a candidate compound and determining whether the level of retinoic acid in said cell is lowered as a result of said contacting.

Paragraph 19. A method for identifying a compound capable of lowering the endogenous level of retinoic acid in a cell which method comprises contacting a cell which expresses a retinol binding protein receptor with a candidate compound and determining whether the level of retinoic acid in said cell is lowered as a result of said contacting.

Paragraph 20. A method for identifying a compound capable of inhibiting the interaction between a retinol binding protein and a retinol binding protein receptor, which method comprises contacting a retinol binding protein receptor, or a fragment thereof capable of binding retinol binding protein, with a candidate compound in the presence of retinol binding protein and determining whether the levels of retinol binding protein binding to the receptor are reduced.

Paragraph 21. A method of reducing proliferation of a hyperproliferative cell which method comprises blocking the activity of a retinol binding protein receptor of the cell.

Paragraph 22. A method according to any preceding Paragraph, which method further comprises the step of contacting the cell with an antagonist of a retinol binding protein receptor.

Paragraph 23. A method according to any preceding Paragraph, in which the endogenous levels of retinoic acid in said cell are lowered.

Paragraph 24. A method of causing a hyperproliferative cell to differentiate which method comprises blocking the activity of a retinol binding protein receptor of the cell.

Paragraph 25. A method of treating or alleviating the symptoms of a patient suffering from a retinoid sensitive disorder, which retinoid sensitive disorder is a disorder which is treatable by administration of retinoids, which method comprises blocking the activity of a retinol binding protein receptor in cells of the patient.

Paragraph 26. A method according to Paragraph 25, in which the retinoid sensitive disorder is a disorder which is treated or whose symptoms are alleviated by administration of higher than physiological levels of retinoid to the patient.

Paragraph 27. A pharmaceutical composition suitable for treating a patient suffering from a hyperproliferative disorder or photoageing, comprising a therapeutically effective amount of a retinol binding protein receptor antagonist together with a pharmaceutically acceptable carrier or diluent.

Paragraph 28. A compound or antagonist identified by a method according to Paragraph 18, 19 or 20.

EXAMPLES

Example 1

Synthesis of Retinol Binding Protein Receptor Protein in Human Keratinocytes and Psoriatic Plaques Anti-human retinol binding protein receptor peptide antibody is generated as follows. A cDNA corresponding to the retinol binding protein receptor expressed in humans (GenBank Accession Number NM_000329) is used as basis for the design of a 9 amino acid peptide. The peptide has the following sequence: VNGATAHNH. (SEQ ID NO: 8)

The peptide is synthesised by the a core facility at the University of Sheffield, coupled to keyhold limpet haemocyanin (KLH) and used to raise antisera in two rabbits using approved procedures. Antibodies are purified from the rabbit anti-sera using retinol binding protein receptor peptide immobilised on activated Sepharose 4B as recommended by the manufacturer (Amersham-Pharmacia) essentially as described in Båvik et al., *Mechanisms of Development* 1997: 69, p. 155-167. Antibodies against retinoic acid synthesis enzymes are selected and assayed for intracellular binding ability using two-hybrid assays as disclosed above.

The peptide is specific to retinol binding protein receptor. The ability of the purified antibody to recognize retinol binding protein receptor is verified by analysis of the protein content of the keratinocytes using SDS-PAGE and protein blot with the antibody essentially as in Båvik et al., *Mechanisms of Development* 1997:69, p. 155-167.

The cell-specific distribution of retinol binding protein receptor is analyzed using standard immunohistochemical techniques described in Wardlaw et al., *Biology of Reproduction* 1997:56, p. 125-132. Antibodies against retinol dehydrogenase (RoDH) are used to localise these proteins. The expression pattern is shown in FIGS. 2 and 3.

Figure 2:
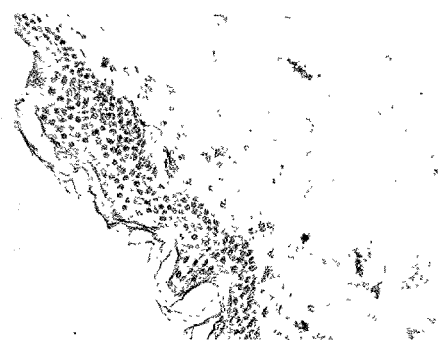
FIG. 2 shows the immunohistochemical colocalisation of retinol binding protein receptor (RBPr) and retinol dehydrogenase (RoDH) in normal skin. Proteins involved in the generation of the retinoic acid signal are found together in the superficial margin of the stratum spinosum and the border of the stratum granulosum of normal skin.
Figure 2:
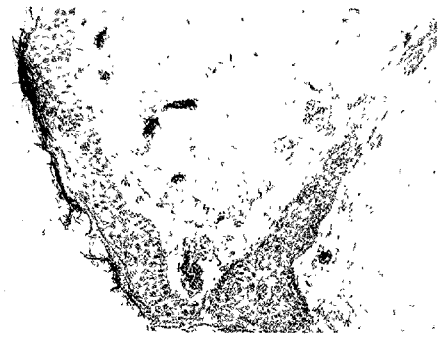

FIG. 2 shows the colocalisation of retinol binding protein receptor (RBPr) and retinol dehydrogenase (RoDH) in normal skin. Thus, FIG. 2 shows using immunohistochemical localisation that proteins involved in the generation of the retinoic acid signal are found together in the superficial margin of the stratum spinosum and the border of the stratum granulosum of normal skin.

Figure 3:
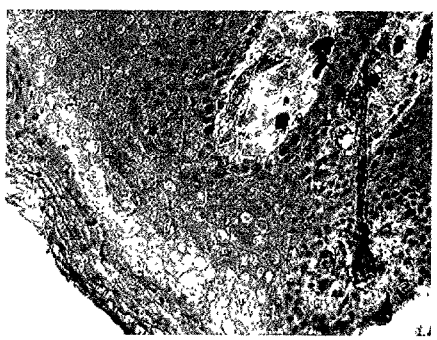
FIG. 3 shows the immunohistochemical colocalisation of retinol binding protein receptor (RBPr) and retinol dehydrogenase (RoDH) in psoriatic plaques. Proteins involved in the generation of the retinoic acid signal are found together in psoriatic plaques.
Figure 3:
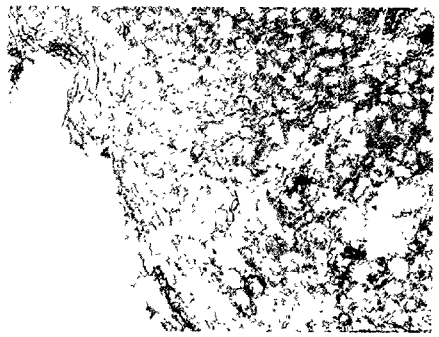

FIG. 3 shows the coloclisation of retinol binding protein receptor (RBPr) and retinol dehydrogenase (RoDH) in psoriatic plaques. Thus, FIG. 3 shows using immunohistochemical localisation that proteins involved in the generation of the retinoic acid signal are found together in psoriatic plaques.

Example 2

Monoclonal Antibodies Against Retinol Binding Protein Receptor

Monoclonal antibodies are generated against retinol binding protein receptor, using protocols essentially as described in Båvik et al., *Experimental Cell Research* 1995:216, p. 358-362. Antibodies are generated against a human retinol binding protein receptor identified from the eye (Nicoletti, et al., 1995, *Hum. Mol. Genet.* 4 (4), 641-649), as well as against against keratinocyte-specific retinol binding protein receptors cloned as described below.

A mouse monoclonal anti-bovine retinol binding protein receptor antibody (P 142) is obtained as described in Båvik et al., supra. This antibody shows reactivity against retinol binding protein receptor in bovine RPE microsomes. A detailed protocol is provided in Bavik et al., supra, and a summary of the protocol is as follows.

RPE microsomes are isolated from frozen human eyes and used for footpad immunisation of BALB/C mice essentially as described in Båvik et al., *Experimental Cell Research* 1995:216, p. 358-36. Lymph nodes are isolated, homogenised and fused with P3X63-Ag.653 myeloma cells. Hybridomas are spread and cultured in 96 well plates. The cells in wells containing Ig of the correct specificity, as described below, are subcloned, the specificity verified and stored frozen.

The monoclonal antibodies produced by this procedure are able to specifically block binding of labelled retinol binding protein to bovine RPE microsomes as assayed using the protocol described in Båvik et al., *Experimental Cell Research* 1995:216, p. 358-362. They are also able to specifically immunoprecipitate labelled retinol binding protein receptor protein synthesised by in vitro transcription of the cloned human keratinocyte retinol binding protein receptor cDNA. Unrelated control Ig is negative in both assays. (Båvik et al., 1995).

In order to produce monoclonals against a keratinocyte specific retinol binding protein receptor, purified receptor is injected into BALB/C mice, and antibodies isolated as described above.

Example 3

Protocols, including Culture of Hyperproliferative Psoriatic Keratinocytes

The methods used for culturing hyperproliferative psoriatic keratinocytes are essentially the same as those for culturing normal human epidermal keratinocytes described in detail in Båvik et al., *Experimental Cell Research* 1995:216, p. 358-362. A summary of the adapted protocol follows.

Materials

Keratinocyte Growth Medium (KGM): serum-free medium (Clonetics, Promocell, Gibco) supplemented with bovine pituitary extract with low $Ca^{2+}$ (0.03-0.5 mM); PBSA (PBS $Ca^{2+}$ & $Mg^{2+}$-free); EDTA (0.5%); Trypsin (1:250, 0.2 & 0.6%); cryopreservation ampoules; Centrifuge tube, 50 ml; Petri dishes, bacteriological grade, 100 mm; Scalpels, curved forceps; Iodine 10% (Betadine).

All-trans Retinol (ROL), Retinoic Acid (RA), $CaCl_2$ Disulfiram, Carbenoxolone and Citral are purchased from Sigma Chemical Co. RBP is purified from donated serum (Peterson, P. A. (1971) *J. Biol. Chem.* 246, 34-43).

Antibodies

The monoclonal antibody P142 is prepared from injection of RPE microsomes as previously published (Båvik, C. O., Peterson, P. A., Eriksson, U. (1995). *Exp. Cell. Res.* 216, 358-362). Control IgM is produced by University of Sheffield Antibody Resource Centre.

Generation of Keratin 1 DNA Probe

A sequence of the human K1 cDNA (1046-1630 was amplified by PCR (Pfu Polymerase 35 cycles) using primers 5'-GCATCATTGCTGAGGTCAAGGC-3' (SEQ ID NO: 9) and 3'-CACCTCCAGAACCATAGC-5'. (SEQ ID NO: 10) This sequence was cloned into JM109 cells (Promega) using PCR-Script Amp Cloning Kit (Stratagene) and cells scaled up in LB Broth. The plasmid DNA was extracted from the JM109 cells using HiSpeed Plasmid Midi Kit (QIAGEN). The probe sequence was cut out using BamH1 and SacII restriction Enzymes (Promega). The DNA was run on a 1.5% Agarose gel, cut out and purified using QIAexII Gel Extraction Kit (QIAGEN).

Protocol for Culture of Hyperproliferative Psoriatic Keratinocytes

Biopsy samples are obtained from psoriatic patients. Skin from patients with chronic plaque psoriasis are obtained with informed consent. Ethical approval has been obtained previously from The South Sheffield Regional Ethics Committee. Biopsies are all be taken from the lower back in psoriasis patients aged 40 to 60.

Epidermal Separation

Remove subcutaneous tissue and some of the dermis with scissors, dissect skin into 1×2 cm pieces with a scalpel. Rinse the tissue 2-5 times in PBSA. Float skin samples on 0.6% Trypsin in PBSA (pH 7.4) ON at 4° C. (or alternatively for 20-30 min at 37° C.)

The separation of the epidermis is carefully monitored. When the first detachment of the epidermis is visible at the cut edges of the skin sample place the pieces (dermis-side down) in 100 mm Petri dishes. Irrigate with 5 ml of complete culture medium (incl. serum). Peel off the epidermis with forceps and collect it in a 50 ml centrifuge tube containing 20 ml of complete culture medium (KGM). Separate the keratinocytes from the epidermal cells by gently pipetting and sieving through a nylon gauze of 100 μm mesh. Wash the isolated epidermal cells twice in KGM by centrifugation at 100 g for 10 min, and count the total number of cells.

An alternative procedure follows, which may be used for normal human keratinocytes:

Pieces of skin are washed thoroughly for 30 minutes in Betadine solution (10% iodine) followed by 2×10 minute washes in PBS. After removal of the subcutaneous tissue and dermis with a scalpel the skin is dissected into 5×10 mm pieces. The skin pieces are rinsed 5× in PBS followed by incubating in Dispase (grade 11, 2.4 U/ml, Boehringer Mannheim) for 18 hours at 4° C.

The skin pieces are then placed dermis side down in 100 mm Petri dishes and are irrigated with 5 ml KSFM. The epidermis is peeled off with forceps and incubated in 10 ml 1× Trypsin/EDTA solution for 10 minutes at 37° C. followed by addition of 10 ml KSFM. The sample is mechanically agitated by aspiration and ejection from a transfer pipette. The resulting cell suspension is sieved using a cell strainer (Becton Dickinson) rinsing through with KSFM. The isolated epidermal cells are then washed twice in KSFM by centrifugation at 100 g for 10 min. Cells are seeded as below.

Primary Culture

Cells are seeded at 37° C. in KGM medium at a density of 2500 cells/cm$^2$ in a 25 cm$^2$ cell culture flask. The medium is replaced every 48 hours and cells are passaged when confluent.

For normal human keratinocytes, the following procedure may be used:

Primary cultures were seeded at 3500 cells/cm$^2$ in K-SFM 25 cm$^2$ tissue culture flasks. The medium was changed (5 ml per flask) the day after seeding and every other day thereafter. At 70-80% confluence the cells were subcultured by seeding 3500 cells/cm$^2$ in new 25 cm$^2$ flasks. On the day that the subcultures reached confluence the medium was switched to medium containing the experimental treatments.

The cells were cultured for 4 days, replacing the experimental medium every other day, before harvesting the cells.

RNA Extraction and Analysis

RNA extraction is carried out according to the manufacturers instructions using the RNeasy kit (QIAGEN). 20 μg of RNA for each treatment was separated on a 1.2% agarose (1.8% formaldehyde) gel and transferred onto a nylon membrane (Zeta probe GT membranes, BioRad) by capillary transfer. The RNA is fixed to the membrane by UV crosslinking. DNA probes for the differentiation markers K1 and K10 (50 ng) are labelled with [α-$^{32}$P] dCTP using the Prime-It RmT Primer labeling kit (Stratagene) following the manufacturer's instructions. Unincorporated nucleotides are removed by elution through a Microspin G25 column (Pharmacia Biotech). The blots are wetted in 0.25M sodium phosphate (pH 7.2)/7% SDS for 30 minutes at 65° C. Fresh hybridisation solution is added along with the radiolabelled probe and the blot is hybridised overnight at 65° C.

The blot is washed for 2×5 minutes in 0.25M sodium phosphate (pH 7.2), 7% SDS and then for 2×5 minutes in 20 mM sodium phosphate (pH 7.2), 5% SDS at 65° C. The wash steps are repeated until a clear distinction can be made between the signal and non-specific background. The blot is exposed to x-ray film for 24 hours before developing.

Proliferation Assay (Coulter Cell Counter)

Cell Seeding and Analysis: Purchased secondary cultures or primary cultures (from donor skin) are seeded at 3500 cells/cm$^2$ in K-SFM 25 cm$^2$ tissue culture flasks. The medium is changed (5 ml per flask) the day after seeding and every other day thereafter. At 70-80% confluence the cells are subcultured by seeding 3500 cells per well in 24 well cell culture plates, each well containing 500 μl of K-SFM. One well plate is seeded for each treatment. After allowing one day for settling the cells are switched to experimental medium (500 μl per well). Stock solutions of additions are as before. Experimental treatments are as follows:

The medium is replaced every other day. Cells are harvested by trypsinisation. 500 μl Trypsin/EDTA is added to each well to be harvested and then aspirated off. The well plates are incubated for 5-6 min at 37° C. 500 μl PBS is added to the wells and the cells are resuspended. The cell suspension is added to 20 ml Isoton solution in a Coulter counter "Accuvette" and the cells are counted. On each harvest, 3 wells of cells are counted for each treatment and 3 counts were made for each well.

Cell number is calculated as follows: Coulter Counter removes 500 μl of 20 ml sample (1/40). Multiply cell count by 40 to obtain cell number in cup, this equals the total number of cells in one well (approximately, as ~10% taken out for viability test).

The methods used for culturing normal human epidermal keratinocytes are essentially the same as for psoriatic keratinocytes. Normal skin is obtained from skin discarded from operative procedures such as abdominal operations or plastic surgery. Normal adult human epidermal keratinocytes (NHEK) are donated by patients undergoing surgery (ethical approval obtained from Trent Multicentre Research Ethics Committee MREC/98/4/018). Biopsy samples may also be obtained from, for example, foreskin, adult tissue. Informed consent is also obtained for this use of discarded tissue from the patients.

Example 4

Blocking of Retinol Binding Protein Receptor Activity in Hyperproliferative Psoriatic Keratinocytes Using Antibody Hyperproliferative psoriatic keratinocytes are cultured as described above in serum-free medium with or without the addition of 2 μM human retinol binding protein. At confluence the cells are treated (see Table 1 below) with 1 mg/ml monoclonal Ig or 1 mg/ml unrelated control IgM 1 mg/ml for 96 hours (medium replaced after 48 hours). Treatments shown in Table 1 are for duplicate T-25 flasks (2×7 ml for each treatment).

TABLE 1

Treatments of hyperproliferative psoriatic
keratinocytes with anti-retinol
binding protein receptor antibody P142

| FLASK | KGM (μl) | CaCl$_2$, 120 MM (μl) | RBP 0.2 μM (μl) | P142 (μl) |
|---|---|---|---|---|
| 1 | 6930 | 70 | 0 | 0 |
| 2 | 6631 | 70 | 38 | 261 |
| 3 | 6890 | 70 | 38 | 0 |

The final concentrations are: Ca$^{2+}$ 1.2 mM, RBP 0.6 μM, immunoglobulins 1 mg/ml.

Proliferation Assay

Figure 4:
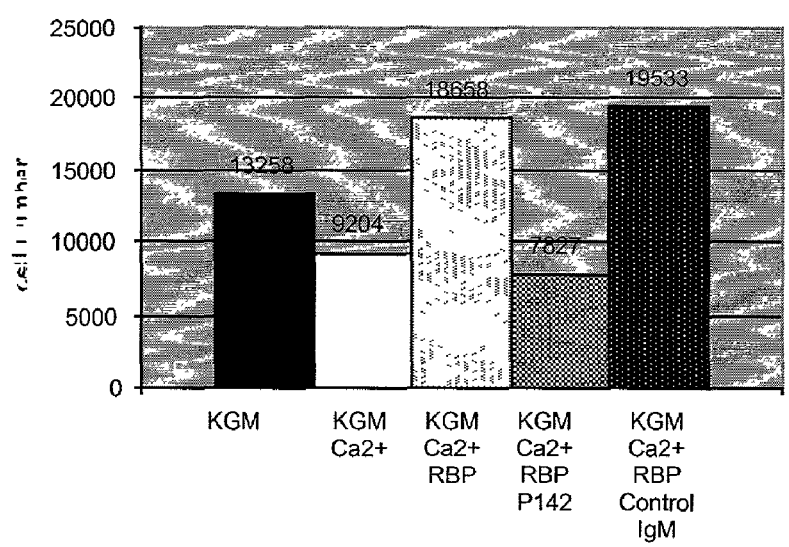
FIG. 4 shows the results of a proliferation assay of hyperproliferative psoriaticnormal human epidermal keratinocytes treated with anti-RBPr antibody P142. The X-axis shows cell counts. The figure shows cell numbers of hyperproliferative psoriatic keratinocytes after 3 days of treatment with antibody. RBP increases proliferation of cultured hyperproliferative psoriatic keratinocytes overcoming the differentiation effects of calcium addition (1.2 mM). This effect is reversed after addition of the monoclonal antibody P142 to the culture medium. Addition of control IgM has an effect on proliferation similar to that of calcium addition alone.

FIG. 4 shows results of a proliferation assay on hyperproliferative psoriatic keratinocytes treated with anti-retinol binding protein receptor antibody P142. Thus, RBP increases proliferation of cultured hyperproliferative psoriatic keratinocytes overcoming the differentiation effects of calcium addition (1.2 mM). This effect is reversed after addition of the monoclonal antibody P142 to the culture medium. Addition of control IgM has an effect on proliferation similar to that of calcium addition alone (with RBP).

Thus, treatment with anti human retinol binding protein receptor antibody but not control antibody enhances the proliferation of psoriatic keratinocytes when these are cultured in media containing retinol binding protein. Anti-human retinol binding protein receptor antibody reduces proliferation of hyperproliferative psoriatic keratinocytes.

Differentiation Assay

Synthesis of mRNA for the K1 and K10 keratin (markers for commitment to terminal differentiation) is examined by quantitative reverse transcription PCR (RT-PCR). Synthesis of mRNA for Cyclin D (a marker for cell proliferation) is also assayed by RT-PCR. Standard protocol for RT-PCR is followed as recommended by the manufacturer of the PCR machine (PE 2400) using 1 μg RNA from each keratinocyte culture. Suitable primers for RT-PCR are designed based on the human sequences of K1 and K10 deposited in GenBank. Northern blots are also performed: cells are harvested, RNA extracted and 20 μg RNA loaded into each well of a formaldehyde/agarose gel. The RNA is blotted onto a nylon membrane by capillary transfer and expression of K1 mRNA is determined by Northern hybridisation with a radiolabelled DNA probe.

Results of a differentiation assay on hyperproliferative psoriatic keratinocytes treated with anti-retinol binding protein receptor antibody P142 show that inhibition of differentiation in keratinocytes (under differentiation pressure from 1.2 mM calcium) produced by RBP is reversed by the addition of the P142 antibody. Control antibody has no effect; thus the expression is similar to that of calcium and retinol binding protein.

Thus, treatment with anti human retinol binding protein receptor antibody but not control antibody enhances the expression of K1 when psoriatic keratinocytes are cultured in media containing retinol binding protein. Anti-human retinol binding protein receptor antibody encourages differentiation of hyperproliferative psoriatic keratinocytes.

Blocking of Retinol Binding Protein Receptor Activity in Normal Human Epidermal Keratinocytes Using Antibody The above experiment is repeated, except that normal human epidermal keratinocytes are used instead of hyperproliferative psoriatic keratinocytes. The experimental medium consists of defined keratinocyte growth medium (devoid of pituitary extract) with or without the addition of CaCl$_2$, RBP, P142 (anti-RBP receptor antibody) or a control IgM. CaCl$_2$ is added as a 120 mM (100×) solution in dH2O to a final concentration of 1.2 mM. RBP is added to a final concentration of 0.2 μM or 0.6 μM. P142 and control IgM are added to a final concentration of 1 mg/ml.

Figure 5:
FIG. 5 shows results of a differentiation assay of normal human epidermal keratinocytes treated with anti-RBPr antibody P142. A Northern blot is probed for differentiation using keratin 1 probe. 20 μg of RNA is loaded in each lane.

Identical results to those from the hyperproliferative psoriatic keratinocyte experiment are found (see FIG. 5). Treatment with anti human retinol binding protein receptor antibody but not control antibody enhances the proliferation of normal human epidermal keratinocytes when these are cultured in media containing retinol binding protein. Treatment with anti human retinol binding protein receptor antibody but not control antibody enhances the expression of K1 when normal human epidermal keratinocytes are cultured in media containing retinol binding protein. Anti-human retinol binding protein receptor antibody reduces proliferation and encourages differentiation of normal human epidermal keratinocytes.

Example 5

Blocking of Retinol Binding Protein Receptor Activity in Hyperproliferative Psoriatic Keratinocytes Using Peptide Competition Engineered Peptides Synthetic peptides are designed based upon the opening loops of the known retinol binding protein structure as well as against its C-terminus, and tested for inhibition of retinol binding protein receptor activity.

Three loops surround the opening of retinol binding protein where retinol is assumed to enter/exit the protein. This is the transthyretin binding region and is also assumed to be the retinol binding protein receptor binding region of the protein (Naylor and Newcomer, *Biochemistry* 1999:38, p. 2647-2653; Sivaprasadarao and Findlay, *Biochemical Journal* 1994:300, p. 437-442; Sundaram et al., *Methods in Molecular Biology* 1998:89, p. 141-153). Synthetic peptides may be synthesised corresponding to the amino acids of the opening loop peptides in human retinol binding protein for use as putative antagonists of retinol binding protein receptor activity. Two specific peptides shown in Table 2 are tested.

TABLE 2

| RBP loop peptides | | |
|---|---|---|
| Peptide | Location | Sequence |
| Peptide 589 | G59 - A71 | Gly-Arg-Val-Arg-Leu-Leu-Asn-Asn-Trp-Asp-Val-Cys-Ala |
| Peptide 592 | M88 - D102 | Met-Lys-Tyr-Trp-Gly-Val-Ala-Ser-Phe-Leu-Gln-Lys-Gly-Asn-Asp |

Amino acids are numbered as in Cowan et al., *Proteins: Structure, Function and Genetics* 1990:8, p. 44-61. Peptides 589 (Gly-Arg-Val-Arg-Leu-Leu-Asn-Asn-Trp-Asp-Val- Cys-Ala) (SEQ ID NO: 11) and 592 (Met-Lys-Tyr-Trp-Gly-Val-Ala-Ser-Phe-Leu-Gln-Lys-Gly-Asn-Asp) (SEQ ID NO: 12) are synthesised to mimic the proposed binding regions of RBP to its receptor, by Arthur Moir, University of Sheffield.

Next, hyperproliferative epidermal keratinocytes are obtained, isolated and cultured as described above in Example 3. Hyperproliferative psoriatic keratinocytes are cultured as described above in serum-free medium with or without the addition of 2 μM human retinol binding protein. At confluence the cells are treated (see Table 3 below) for 96 hours with peptides to 6 μM (medium replaced after 48 hours). Treatments shown in the Table 3 are for duplicate T-25 flasks (2×7 ml for each treatment).

Table 3 below summarises the treatments of these experiments.

TABLE 3

Treatments for differentiation assay on hyperproliferative psoriatic keratinocytes using peptide inhibition of the RBP receptor.

|   | KGM | 120 mM Ca2+ | RBP 0.25 mg/ml | PEPTIDE 300 μM |
|---|-----|-------------|-----------------|-----------------|
| 1 | 6930 | 70 | — | — |
| 2 | 6573 | 70 | 357 | — |
| 3 | 6503 | 70 | 357 | 70 (589) |
| 4 | 6503 | 70 | 357 | 70 (592) |

The final concentrations are: $Ca^{2+}$ 1.2 mM, RBP 0.6 μM, peptides 6 μM.

Proliferation Assay

A proliferation assay on hyperproliferative psoriatic keratinocytes treated with RBP loop peptides shows that the effect of RBP to increase proliferation of cultured hyperproliferative psoriatic keratinocytes overcoming the differentiation effects of calcium addition (1.2 mM) is reversed after addition of the either peptide 589 or peptide 592 to the culture medium. Addition of control peptide has an effect on proliferation similar to that of calcium addition alone.

Differentiation Assay

Expression of K1 and K10 markers is determined as described above in Example 4.

Results of a differentiation assay conducted on hyperproliferative psoriatic keratinocytes treated with RBP loop peptides 589 and 592 show that the inhibition of differentiation in psoriatic keratinocytes by RBP is reversed by the addition of peptide 592 or peptide 389, derived from RBP.

Thus, it is found that 6 μM peptide 589 reduces proliferation and enhances the expression of K1 and K10 markers in hyperproliferative psoriatic keratinocytes. Furthermore, 6 μM peptide 592 has the same effect. The peptides containing the same amino acids but synthesised in reverse order are all negative in the assays.

Other peptides, including K29-Q38 and C174-L183 are tested; they are found to have similar effects.

Peptides Isolated by Epitope Display Screen

Peptides capable of reducing proliferation of hyperproliferative psoriatic keratinocytes and normal human epidermal keratinocytes are also isolated by screening a epitope display phage library.

Bovine RPE microsomes are isolated as in Båvik et al., Journal of Biological Chemistry 266:14978-14985, 1991. 20 mg RPE microsomes are mixed with 10 μl phage display library (Scott J K and Smith G P, Science 249:386-390, 1990). The mixtures are incubated at +4 degrees C. for 30 minutes and the microsomes pelleted by centrifugation through a bovine serum albumin solution essentially as in Båvik et al., Journal of Biological Chemistry 266:14978-14985, 1991.

The pellet is resuspended and the phages propagated as in Scott J K and Smith G P, Science 249:386-390, 1990. The above process of selection and propagation of the phages is repeated twice. Finally the selected phages are mixed with fresh RPE microsomes together with 20 mM human RBP, incubated and centrifuged as above. The phages remaining in the supernatant are collected and propagated.

Individual phages are isolated by infecting log phase Esherichia coli K91Kan cultures and plating onto LB plates containing 25 mg/ml of tetracycline. DNA from individual phages is purified and sequenced using standard procedures (Sambrook et al., 1989). 20 cloned phages are sequence and found to encode 5 groups of unique display peptide sequences: Peptide A, Peptide B, Peptide C, Peptide D, Peptide E. Five peptides (A-E) corresponding to those encoded by the isolated phages are synthesised as described above.

An initial binding assay is constructed to determine the binding specificity of the peptides. Binding of 0.2 mM labelled human RBP to bovine RPE microsomes (assayed as in Båvik et al., Journal of Biological Chemistry 266:14978-14985, 1991) is inhibited by 10 μM of peptides (A-E). Peptides containing the same amino acids but synthesised in reverse order are all negative in the assay.

Peptides A-E are tested in a proliferation assay and a differentiation assay on hyperproliferative psoriatic keratinocytes, as described above, and are found to be active in preventing proliferation and enhancing differentiation of hyperproliferative psoriatic keratinocytes.

Blocking of Retinol Binding Protein Receptor Activity in Normal Human Epidermal Keratinocytes Using Peptide Competition The above experiment is repeated, except that normal human epidermal keratinocytes are used instead of hyperproliferative psoriatic keratinocytes.

The experimental medium consists of defined keratinocyte growth medium (devoid of pituitary extract) with or without the addition of $CaCl_2$, all-RBP or the respective peptides. $CaCl_2$ is added as a 120 mM (100×) solution in dH2O to a final concentration of 1.2 mM, RBP is added as a stock solution of 0.25 mg/ml to a final concentration of 0.6 μM. The peptides are dissolved in EtOH and were added as a 100× stock solution to a final concentration of 3 μM.

Figure 6:
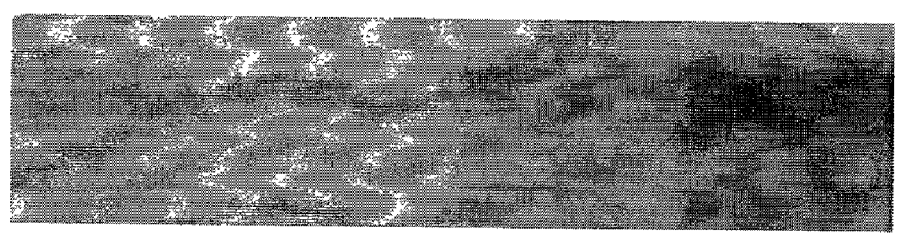
FIG. 6 shows results of a differentiation assay of normal human epidermalkeratinocytes treated with peptide 589 and peptide 592. A Northern blot is probed for differentiation using Keratin 1 probe. 20 μg of RNA is loaded in each lane.

Similar results are found when normal human epidermal keratinocytes are treated with RBP loop peptides as with hyperproliferative psoriatic keratinocytes (see FIG. 6). Thus, it is found that 6 μM peptide 589 or 6 μM reduces proliferation and enhances the expression of K1 and K10 markers in normal human epidermal keratinocytes. The peptides containing the same amino acids but synthesised in reverse order are all negative in the assays.

Example 6

Blocking of Retinol Binding Protein Receptor Activity in Renal Carcinoma Cells Using Antibody and Peptide Competition Renal Carcinoma cell lines (COS1 and COS7) are purchased from the European Cell Culture Collection, thawed and propagated according to the instructions from the supplier; cells are cultured essentially in the same manner as for normal human keratinocytes (Example 3 above), except that cells are seeded at 20 000 cells/cm$^2$, with only one treatment with antibody P142, control immunoglobulin, peptide 589, peptide 592 or control peptide 24 hrs after seeding.

Proliferation is assayed by counting cells in a Coulter counter, as described above.

COS-1 and COS-7 Results
Treatments for COS-1 and COS-7 are shown in Table 4 below.

TABLE 4

Treatments for the Cos-1 and Cos-7 cell lines are made up as follows: 500 μl was used to treat each well. DMEM medium contain 10% fetal bovine serum and 2 mM L-glutamine.

| Amount added/μl | 1 DMEM | 2 DMEM + P142 (final conc 1 mg/ml) | 3 DMEM + Control Ig (final conc 1 mg/ml) | 4 DMEM + Peptide 592 (final conc 6 μM) | 5 DMEM + Peptide 589 (final conc 6 μM) | 6 DMEM + Control peptide (final conc 6 μM) |
|---|---|---|---|---|---|---|
| DMEM | 2000 | 1952 | 1938 | 1980 | 1960 | 1980 |
| P142 (41 mg/ml) | | 48 | | | | |
| Control Ig (32 mg/ml) | | | 62 | | | |
| Peptide 592 (600 μM) | | | | 20 | | |
| Peptide 589 (300 μM) | | | | | 40 | |
| Control peptide (600 μM) | | | | | | 20 |
| Total | 2000 | 2000 | 2000 | 2000 | 2000 | 2000 |

Figure 7:
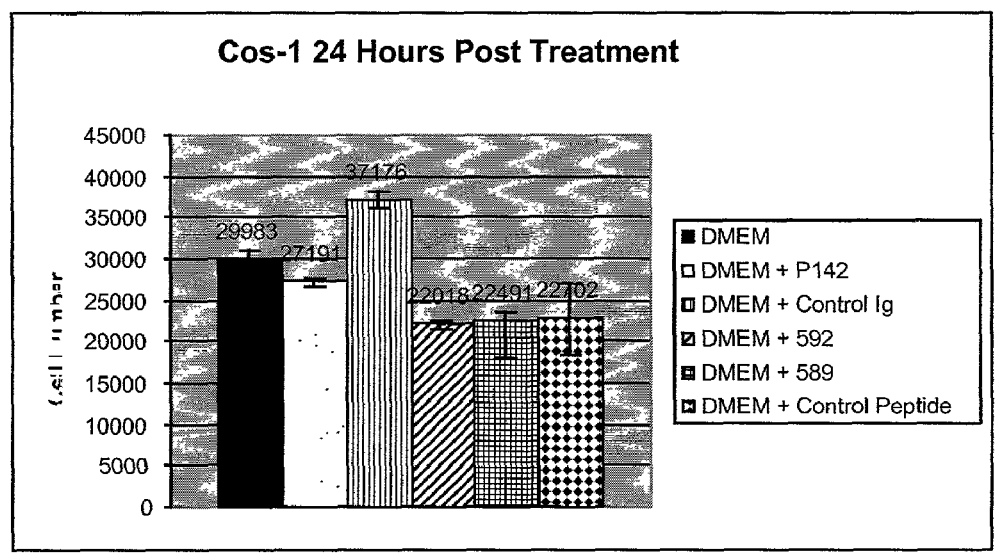
FIG. 7 shows results of a proliferation assay of COS-1 cells treated with anti-retinol binding protein receptor antibody P142, control antibody, peptide 592, peptide 589 and control peptide. X-axis shows cell counts. Upper panel: cell counts 24 hours post treatment, lower panel: cell counts 48 hours post treatment.
Figure 7:
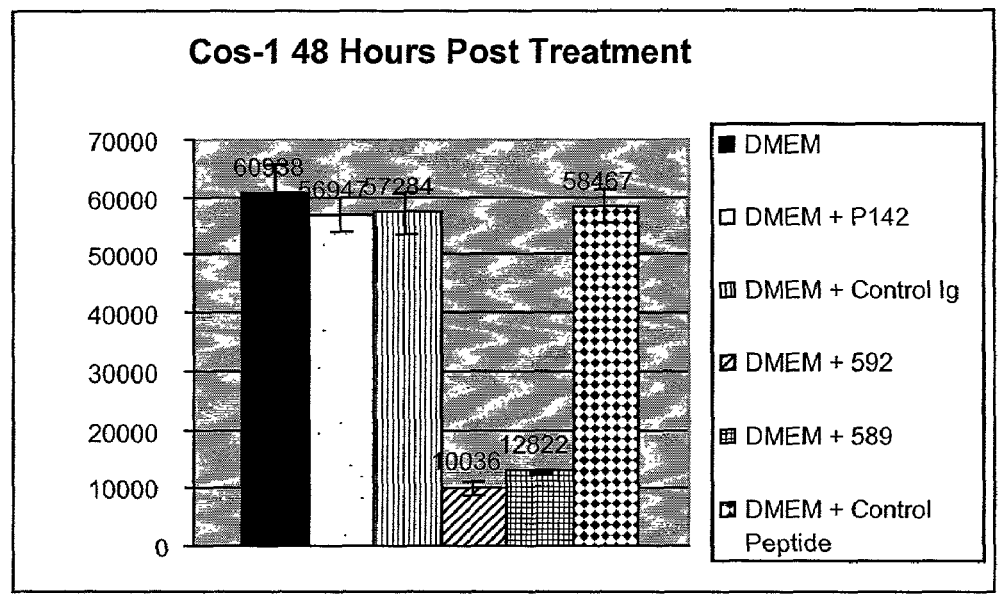

FIG. 7 shows results of a proliferation assay of COS-1 treated with anti-retinol binding protein receptor antibody P142, control antibody, peptide 589, peptide 592 and control antibody. This figure consists of graphs depicting cell numbers harvested at 24 hours (upper panel) and at 48 hours after treatment (lower panel). This figure shows a marked reduction in proliferation of Cos-1 cells following the addition of peptides 592 and 589 and a more subtle reduction in proliferation following the addition of immunoglobulin P142.

Figure 8:
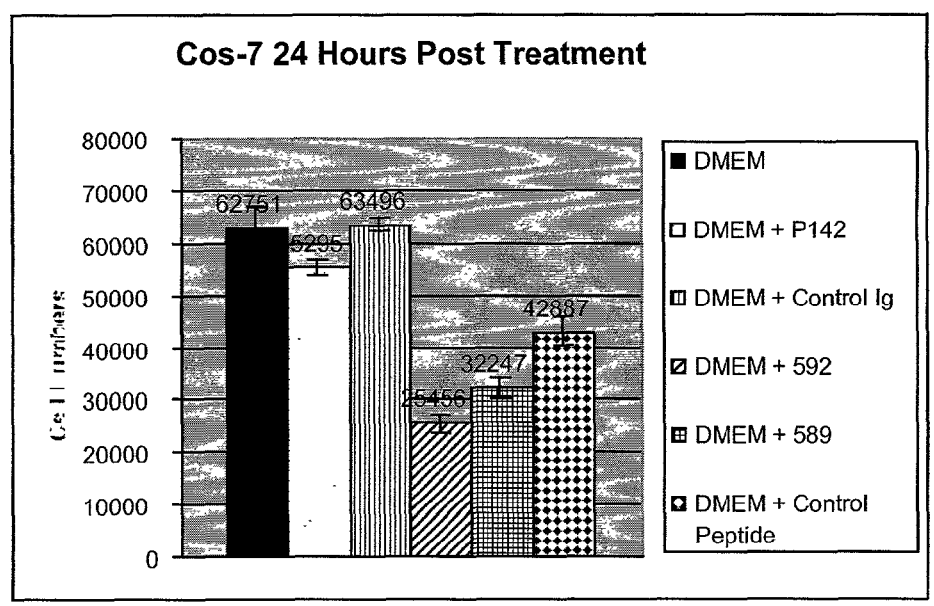
FIG. 8 shows results of a proliferation assay of COS-7 cells treated with anti-retinol binding protein receptor antibody P142, control antibody, peptide 592, peptide 589 and control peptide. X-axis shows cell counts. Upper panel: cell counts 24 hours post treatment, lower panel: cell counts 48 hours post treatment.
Figure 8:
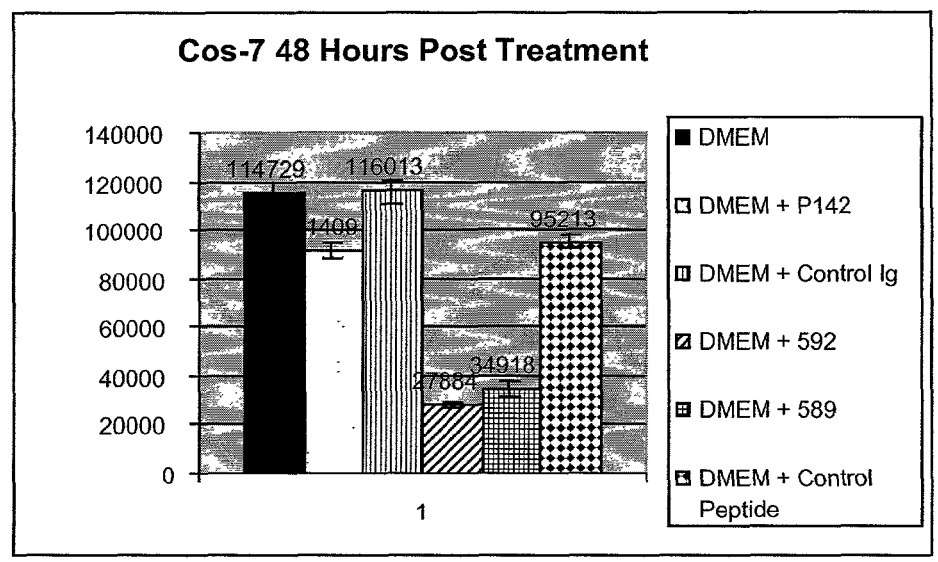

FIG. 8 shows results of a proliferation assay of COS-7 treated with anti-retinol binding protein receptor antibody P142, control antibody, peptide 589, peptide 592 and control antibody. This figure consists of graphs depicting cell numbers harvested at 24 hours (upper panel) and at 48 hours after treatment (lower panel). This figure shows a marked reduction in proliferation of Cos-7 cells following the addition of peptides 592 and 589 and a more subtle reduction in proliferation following the addition of immunoglobulin P142.

Example 7

Blocking of Retinol Binding Protein Receptor Activity in Human Dermal Fibroblast Cell Lines Using Antibody and Peptide Competition Fibroblast cell culture is performed essentially as described for culture of hyperproliferative psoriatic keratinocytes (Example 3), except that following irrigation with complete culture medium, the dermal portion is incubated with 1 mg/ml of collagenase (Sigma) in 20 ml DMEM in a 50 ml centrifuge tube for 16 hours at 37° C. Then 20 ml DMEM containing 5% foetal calf serum and 1% antibiotic/antimycotic solution (Gibco) is added and the cells seeded at 37° C. in DMEM medium+additions at a density of 2500 cells/cm$^2$ in a 25 cm$^2$ cell culture flask. Medium is replaced every 48 hours and cells passaged when confluent.

Treatments for human dermal fibroblasts are shown in Table 5 below:

TABLE 5

Treatments for the human dermal fibroblast cell line were made up as follows: 500 μl was used to treat each well. FGM contained 10% fetal bovine serum.

| Amount added/μl | 1 FGM | 2 FGM + P142 (final conc 1 mg/ml) | 3 FGM + Control Ig (final conc 1 mg/ml) | 4 FGM + Peptide 592 (final conc 6 μM) | 5 FGM + Peptide 589 (final conc 6 μM) | 6 FGM + Control peptide (final conc 6 μM) |
|---|---|---|---|---|---|---|
| DMEM | 2000 | 1952 | 1938 | 1980 | 1960 | 1980 |
| P142 (41 mg/ml) | | 48 | | | | |
| Control Ig (32 mg/ml) | | | 62 | | | |
| Peptide 592 (600 μM) | | | | 20 | | |
| Peptide 589 (300 μM) | | | | | 40 | |

TABLE 5-continued

Treatments for the human dermal fibroblast cell line were made up as follows: 500 µl was used to treat each well. FGM contained 10% fetal bovine serum.

| Amount added/µl | 1 FGM | 2 FGM + P142 (final conc 1 mg/ml) | 3 FGM + Control Ig (final conc 1 mg/ml) | 4 FGM + Peptide 592 (final conc 6 µM) | 5 FGM + Peptide 589 (final conc 6 µM) | 6 FGM + Control peptide (final conc 6 µM) |
|---|---|---|---|---|---|---|
| Control peptide (600 µM) | | | | | | 20 |
| Total | 2000 | 2000 | 2000 | 2000 | 2000 | 2000 |

Figure 9:
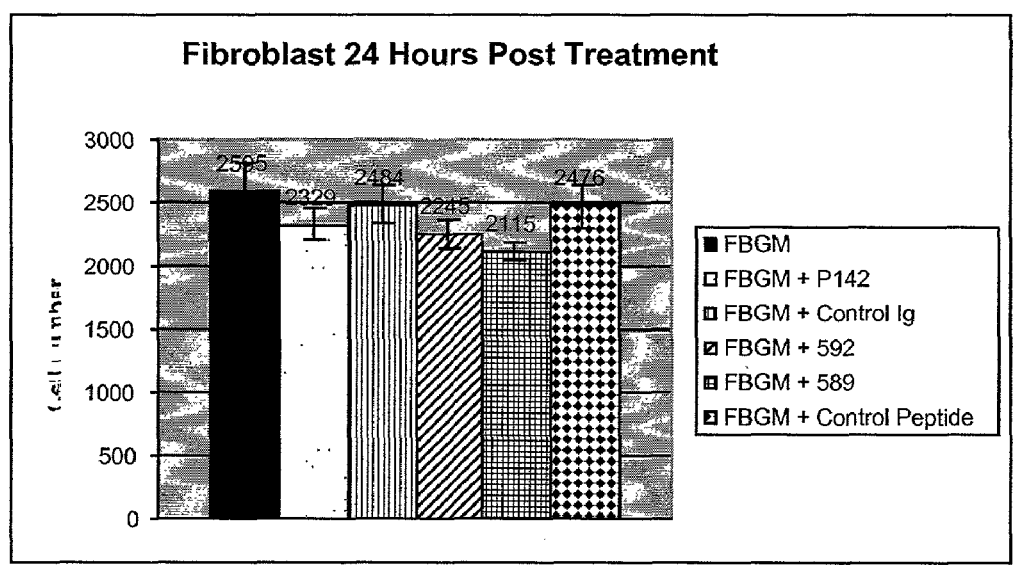
FIG. 9 shows results of a proliferation assay of human dermal fibroblast cells treated with anti-retinol binding protein receptor antibody P142, control antibody, peptide 592, peptide 589 and control peptide. X-axis shows cell counts. Upper panel: cell counts 24 hours post treatment, lower panel: cell counts 4 days post treatment.
Figure 9:
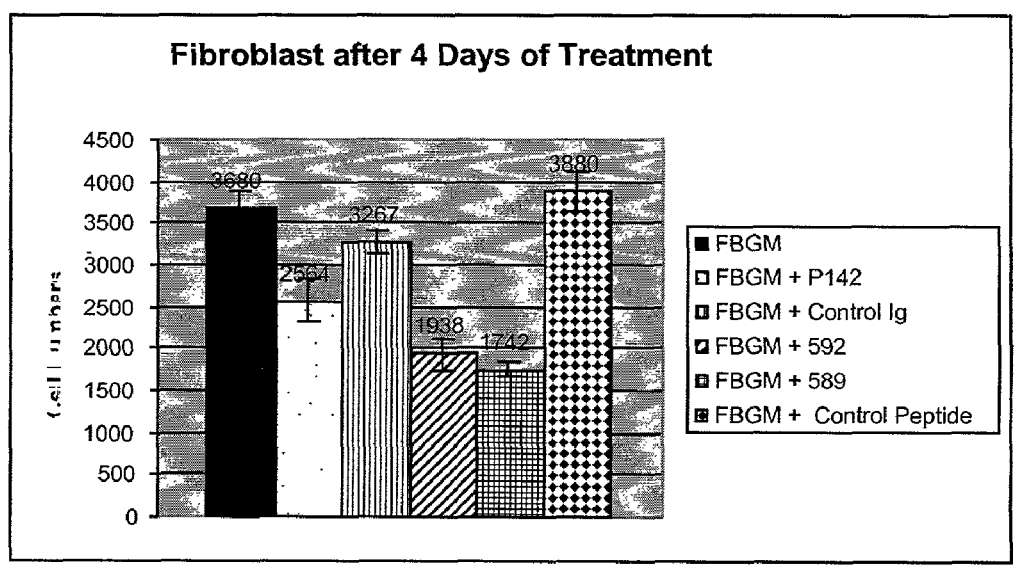

FIG. 9 shows results of a proliferation assay of COS-1 treated with anti-retinol binding protein receptor antibody P142, control antibody, peptide 589, peptide 592 and control antibody. This figure consists of graphs depicting cell numbers harvested at 24 hours (upper panel) and at 4 days after treatment (lower panel). This figure shows a reduction in fibroblast proliferation following the addition of immunoglobulin P142, and a greater reduction in proliferation following the addition of peptides 592 and 589.

Example 8

Blocking of Retinol Binding Protein Receptor Activity in Cells Using Antisense Oligonucleotides The effect of kRBPr specific anti-sense oligodeoxynucleotides (oligos) on retinol binding protein receptor expression and proliferation and differentiation of human keratinocytes is determined. The design of anti-sense oligos may be based on an oligo complementary to the region containing the initial methionine of a keratinocyte RBP receptor sequence. This strategy has been successfully employed for the inhibition of yolk-sac retinol binding protein synthesis (Båvik et al, 1996, Proc. Natl. Acad. Sci. 93, 3110-3114).

An oligo corresponding to the antisense configuration of the initiation codon for Met 1 and 17 bases further downstream is synthesised by the core facility for the Division of Genomic Medicine, University of Sheffield.

Hyperproliferative psoriatic keratinocytes and normal human epidermal keratinocytes are obtained and cultured as described above. The anti sense oligo is included in the culture media at concentrations of 25, 50 and 100 µM for 24, 48 and 72 hours. The expression of kRBPr is examined after oligo treatment by analysis of the protein content of the cells using SDS-PAGE and protein blot with anti-retinol binding protein receptor antibodies essentially as in Båvik et al., Mechanisms of Development 1997:69, p. 155-167.

Treatment of hyperproliferative psoriatic keratinocytes and normal human epidermal keratinocytes with 75 µM antisense oligonucleotide for 48 hours is found to reduce expression of kRBPr. Furthermore, the treatment results in differentiation of the hyperproliferative psoriatic keratinocytes and normal human epidermal keratinocytes and promotion of the expression of K1 and K10 markers. Similar results are obtained with renal carcinoma cell lines COS-1 and COS-7 as well as dermal fibroblast cell lines.

Antisense oligonucleotides with other sequences may be designed and tested. For example, if an anti-sense oligo is found not to be able to block kRBPr expression effectively, it may be redesigned by using sequence positioned 5-10 bp more 3' until an effective oligo is found. Once an effective antisense oligo is found, two different control oligos are designed using the same strategy as previously for retinol binding protein oligos (Båvik et al., 1996, Proc. Natl. Acad. Sci. 93, 3110-3114). These control oligos must leave the expression of kRBPr unchanged. If the control oligos affect kRBPr expression the design of the oligos may be shifted until a suitable region is found. Furthermore, the oligos will preferably be designed so that hairpin formation is avoided. If a keratinocyte contains more than one retinol binding protein receptor gene, then antisense oligos against each of them may be used in combination for effective blocking of retinol binding protein receptor expression.

Example 9

Effects of RDH, ADH and RalDH Inhibitors on Psoriatic Human Epidermal Keratinocytes as Assayed by RA Synthesis, Proliferation and Differentiation Citral and Disulfiram are inhibitors of aldehyde dehydrogenases. Carbenoxolone is an inhibitor of retinol dehydrogenase. $CaCl_2$ is added as a 120 mM solution in $dH_2O$ to a final concentration of 1.2 mM. Retinol is added as a stock solution of 2M in ethanol to a final concentration of 2 µM. The experimental medium consists of defined keratinocyte growth medium (devoid of pituitary extract) with or without the addition of $CaCl_2$, all-trans-retinol or the respective inhibitors.

Protocols used are as described in as in Båvik et al., Experimental Cell research 1995:216, p. 358-362. Briefly, subcultures are grown to confluence in KGM. On day of confluence change to keratinocyte differentiation media (1.2 mM $Ca^{2+}$, KDM) with 2 µM holo-RBP+/−inhibitors (0.6 µM Carbenoxolone; 50 µM Phenylarsine; 10 µM Citral; 0.2 mM 4-Methylpyrazole; 15 µM Disulfiram; 10 µM Citral; 2 mM 3-Mercaptopropionic acid; or drug vehicle alone). Cells are grown for 4 days, and cells are media are harvested.

The concentration of RA in cells and media is analysed directly by HPLC. Essentially as in "Characterisation of retinol metabolism in cultured human epidermal keratinocytes", Randolph R. K. and Simon M., J. Biol. Chem. 268:9198-9205, 1993. The concentration of RA in cells is also analysed indirectly by Northern blot analysis of CRABPII mRNA expression in the keratinocytes, essentially as described in Elder et al. Retinoid Induction of CRABPII nRNA in Human Dermal Fibroblasts: Use as a Retinoid Bioassay, J. Investigative Dermatology 106:517-521, 1996.

Proliferation Assay

Hyperproliferative psoriatic keratinocytes are cultured as described above in serum-free medium with or without the addition of 2 µM human retinol binding protein. At confluence the cells are treated (see Table 6 below) for 96 hours with inhibitors of retinoic acid synthesis (Carbenox, Disulfiram and Citral) to 6 µM, 15 µM and 10 µM respectively (medium replaced after 48 hours). Treatments shown in the Table 6 are for duplicate T-25 flasks (2×7 ml for each treatment).

Table 6 below shows treatments of normal human epidermal keratinocytes for a proliferation assay conducted as part of this experiment. Cells are counted in a Coulter counter.

TABLE 6

Treatments of hyperproliferative psoriatic keratinocytes with retinoic acid synthesis inhibitors for a proliferation assay

| | KGM (ml) | 1.2 mM CA$^{2+}$ (µl) | 2 µM ROL (1000X) (µl) | ETOH (µl) | RETINOIC ACID (1000X) (µl) | INHIBITOR (µl) |
|---|---|---|---|---|---|---|
| 1 | 10 | — | — | — | — | — |
| 2 | 9.9 | 100 | — | — | — | — |
| 3 | 10 | 100 | 10 | — | — | — |
| 4 | 9.9 | 100 | 10 | — | — | 100(Disulfiram 15 µM) |
| 5 | 9.9 | 100 | 10 | — | — | 100(Citral 10 µM) |
| 6 | 9.9 | 100 | 10 | — | — | 100(Carbenoxolone 12 µM) |
| 7 | 9.9 | 100 | — | 100 | — | — |
| 8 | 9.9 | 100 | — | — | 10 | — |

Figure 10:
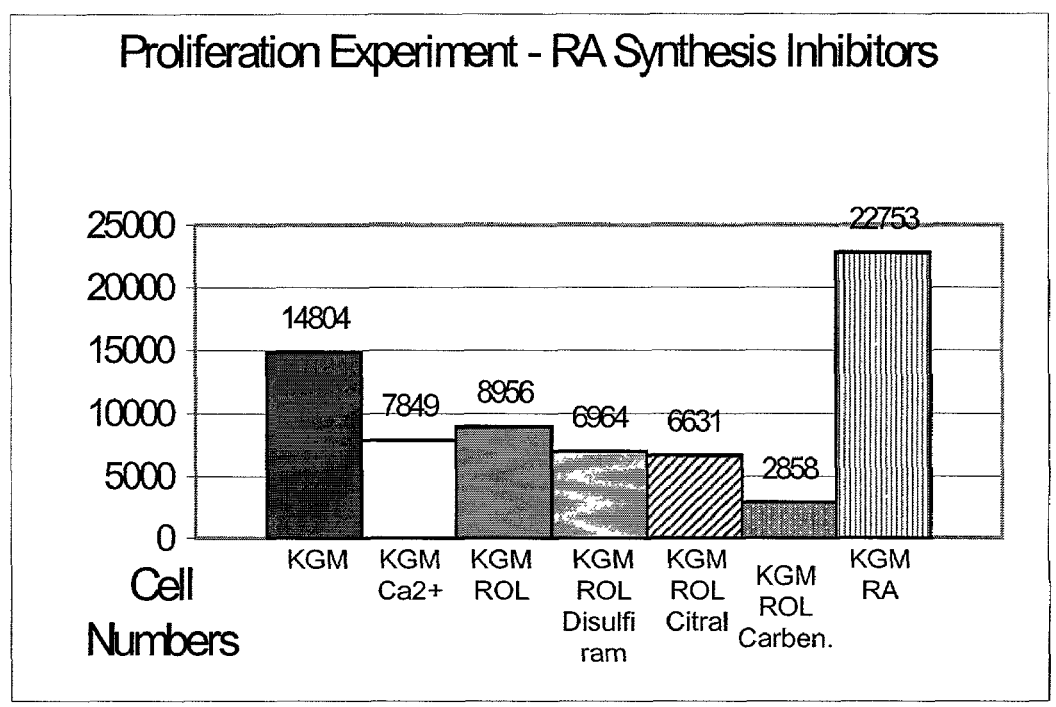
FIG. 10 shows results of a proliferation assay of hyperproliferative psoriatic keratinocytes treated with inhibitors of retinoic acid synthesis. The X-axis shows cell numbers.

Results of a proliferation assay on hyperproliferative psoriatic keratinocytes treated with retinoic acid synthesis inhibitors are shown in FIG. 10. This figure shows that keratinocyte proliferation induced by the addition of retinol and more so by the addition of pure retinoic acid is decreased by RA synthesis inhibitors. A particularly marked effect is seen on addition of Carbenoxolone.

Differentiation Assay

Table 7 below shows treatments of normal human epidermal keratinocytes for a differentiation assay conducted as part of this experiment.

TABLE 7

Treatments of hyperproliferative psoriatic keratinocytes with retinoic acid synthesis inhibitors for a differentiation assay

| | KGM (µL) | CA$^{2+}$ (µL) | ROL (µL) | INHIBITOR (µL) |
|---|---|---|---|---|
| 1 | 6930 | 70 | — | — |
| 2 | 6860 | 70 | 7 | — |
| 3 | 6790 | 70 | 7 | 70 (Disulfiram, final conc. 15 µM) |
| 4 | 6790 | 70 | 7 | 70 (Citral, final conc. 10 µM) |

Synthesis of mRNA for markers of proliferation and differentiation is examined by Northern blot using labeled probes for human Cyclin-A, K5, K6, K14, MDM2 K1, K10, beta 1 integrin, transglutaminase and involucrine. The probes are generated by RT-PCR of human keratinocyte RNA using sequences deposited in GenBank as basis for the design of the primers (accession numbers below). The Northern blots are performed essentially as in Bavik et al. The retinal pigment epithelial membrane receptor for plasma retinol-binding protein; Isolation and cDNA cloning of the 63 kDa protein, J. B. C. 268:20540-20546, 1993 using the above RNA and probes.

Synthesis of mRNA for markers of proliferation and differentiation is also examined by semi-quantitative reverse transcription PCR (RT-PCR). Standard protocols for RT-PCR are followed as recommended by the manufacturer of the PCR machine (PE 2400) using 1 µg RNA from each keratinocyte culture. Suitable primers for RT-PCR are designed based on the human sequences of Cyclin-A, K5, K6, K14, MDM2 K1, K10, beta 1 integrin, transglutaminase and involucrine.

The GenBank accession numbers for the above sequences are as follow: Cyclin A (NM001237), Keratin 1 (M98776), Keratin 5 (AF274874), Keratin 6 (NM005554), Keratin 10 (NM000421), Keratin 14 (NM00526), Keratin 16 (AF061809), Keratin 17, MDM2 (M92424), Beta-1 Integrin (X07979), Transglutaminase (NM000359), Involucrin (XM001677).

A differentiation assay of hyperproliferative psoriatic keratinocytes treated with retinoic acid synthesis inhibitors shows that inhibition of differentiation in keratinocytes (under differentiation pressure from 1.2 mM calcium) produced by ROL is reversed by the addition of RA synthesis inhibitors. Control (ethanol alone) has no effect.

In each of the above cases in which inhibitors are used, the retinoic acid level is found to be reduced in the medium. Treatment of hyperproliferative psoriatic human epidermal keratinocytes cultured in media containing RBP with inhibitors of human RDH, ADH or RalDH is found to inhibit the synthesis of retinoic acid. Thus, 10 µM RA is found in control cells+media while 1 µM RA is found in the presence of RDH inhibitor. The expression level of CRABPII in the presence of RDH inhibitor is reduced compared to that of control.

Example 10

Effects of RDH, ADH and RalDH Inhibitors on Normal Human Epidermal Keratinocytes as Assayed by RA Synthesis, Proliferation and Differentiation The above two experiments are repeated, but with the use of normal human epithelial keratinocytes instead of psoriatic human epidermal keratinocytes.

Figure 11:
FIG. 11 shows results of a differentiation assay of normal human epidermal keratinocytes treated with inhibitors of retinoic acid synthesis. A Northern blot is probed for differentiation using Keratin 1 probe. 20 μg of RNA is loaded in each lane. The inhibition of differentiation in normal human epidermal keratinocytes (under differentiation pressure from 1.2 mM calcium) produced by RBP is reversed by the addition of RA synthesis inhibitors.

Similar results to those obtained on treatment of hyperproliferative psoriatic keratinocytes are obtained (see FIG. 11). Thus, retinoic acid synthesis is inhibited on addition of Carbenoxolone to 6 µM, Disulfiram to 15 µM or Citral to 10 µM. Furthermore, addition of each of these inhibitors is found to inhibit proliferation and to increase differentiation.

Example 11

Effects of RDH, ADH and RalDH Inhibitors on Cultured Renal Carcinoma Cell Lines as Assayed by RA Synthesis and Proliferation 3 out of 4 examined human renal carcinomas over express RBPr (Ma J, Zhang D, Laser M et al: Identification of RPE65 in transformed kidney cells. FEBS Letters 452 (1999) 199-204). Renal Carcinoma cell lines (HEK293, COS1 and COS7) are purchased from ATCC, thawed and propagated according to the instructions from the supplier.

The expression level of RBPr in the renal carcinoma cell lines is examined by Western blot essentially as in Bavik et al., *Characterization of a plasma retinol-binding protein membrane receptor expressed in the retinal pigment epithelium*, J. Biological Chemistry 267: 23035-23042, 1992.

Renal Carcinoma cell lines (HEK293, COS1 and COS7) are cultured in media as above including 2 µM holo-RBP, with or without retinol dehydrogenase or retinal dehydrogenase inhibitors (0.5 mM Carbenoxolone; 50 µM Phenylarsine; 20 µM Citral; 0.2 mM 4-Methylpyrazole; 10 µM Disulfiram; 10 µM Citral; 2 mM 3-Mercaptopropionic acid; or drug vehicle alone).

The concentration of RA in cells and media is analysed directly by HPLC as described above. Synthesis of retinoic acid is found to be inhibited. Thus, 10 µM RA is found in control cell+media and 1 µM RA is found in the presence of RDH inhibitor. The expression level of CRABPII in the presence of RDH inhibitor is reduced compared to that of control.

Synthesis of mRNA for markers of proliferation and differentiation is examined by Northern blot using labelled probes for Cyclin D, as described above. Expression of the differentiation markers vimentin, villin, CALLA/CD 10 is enhanced and expression of the proliferation marker Cyclin D diminished as measured by Northern blot.

Synthesis of mRNA for markers of NHEK proliferation and differentiation is also examined by semi-quantitative reverse transcription PCR (RT-PCR). Standard protocol for RT-PCR were followed as recommended by the manufacturer of the PCR machine (PE 2400) using 1 µg RNA from each cell culture. Suitable primers for RT-PCR was designed based on the human sequences of Cyclin D, vimentin, villin, CALLA/CD10 deposited in GenBank. For details on the PCR protocol see above. Expression of the differentiation markers vimentin, villin, CALLA/CD10 is enhanced and expression of the proliferation markers Cyclin D diminished as measured by semi-quantitative RT-PCR.

Proliferation of cells is assayed by direct cell counting essentially as for determination of proliferation in keratinocyte cell cultures.

Example 12

Effects of RDH, ADH and RalDH Inhibitors on Cultured Fibroblast Cell Lines as Assayed by RA Synthesis, Differentiation and Proliferation The above experiments in Example 11 are repeated on cultured fibroblast cell lines.

Fibroblast cell culture and experiments are performed essentially as described for culture of hyperproliferative psoriatic keratinocytes (above), except that following irrigation with complete culture medium, the dermal portion is processed further. Reference is made to fibroblast culture protocols set out above.

Treatment of human dermal fibroblasts cultured in media containing RBP with inhibitors of human RDH, ADH or RalDH is found to inhibit the synthesis of retinoic acid. 10 µM RA is found in control cell+media and 1 µM RA was found in the presence of RDH inhibitor. The expression level of CRABPII in the presence of RDH inhibitor is reduced compared to that of control.

Synthesis of mRNA for markers of dermal fibroblast proliferation and differentiation is examined by Northern blot using labelled probes for peroxidase, CD44 and CD40 deposited in GenBank. Northern blot protocol as described above. The expression of the differentiation markers peroxidase, CD44 and CD40 is enhanced and the expression of the proliferation markers Cyclin D as measured by semi-quantitative RT-PCR is diminished.

Synthesis of mRNA for markers of dermal fibroblast proliferation and differentiation is also assessed by semi-quantitative reverse transcription PCR (RT-PCR) as described above Suitable primers for RT-PCR are designed based on the human sequences of peroxidase, CD44 and CD40 deposited in GenBank (CD44: XM030319). It is found that the expression of the differentiation markers peroxidase, CD44 and CD40 is enhanced and the expression of the proliferation markers Cyclin D as measured by Northern blot is diminished.

Proliferation of cells is assayed by direct cell counting essentially as for determination of proliferation in keratinocyte cell cultures. RDH, ADH, RalDH inhibitors are found to reduce proliferation.

Example 13

Blocking of Retinol Binding Protein Receptor Activity in Whole Mammalian Embryo Culture Antagonists to retinol binding protein receptor function according to the invention are introduced into the culture medium of mammalian embryo cultures and the resulting effects on cell proliferation/differentiation observed. Any resulting malformations of the embryo are noted and their pathogenesis examined to determine whether a disorder of cell proliferation is evident. The mammalian embryo cultures are established from a transgenic mouse (Mendelsohn et al., 1991, *Development* 113:723-734) which carriers a reporter construct for the retinoic acid-responsive gene, RAR-β2. This provides further information of retinoic acid signalling following the retinol binding protein receptor-block.

Protocol for Embryo culture: Explanation of Embryos

On day 8.5 pc the uteri are dissected free from the pregnant mice and placed onto a dish containing pre-warmed Tyrode's saline. By carefully tearing open the antimesometrial side of the uterus, decidual swellings are exposed under a dissection microscope. Using two pairs of matchmakers forceps a groove is cut in the decidua and one half is gently pulled away. Using one pair of forceps the remaining strip of decidua containing the embryo is impaled, and the other pair is used to tease the embryo away. Finally, Reichert's membrane and its adherent parietal endoderm cell layer are torn open, leaving the underlying yolk sac and the ectoplacental cone intact. Any damaged, retarded or malformed embryos are discarded, and the remaining are grouped together according to their precise somite stage.

Culture Media and Conditions

Embryos are cultured for 24 h in a mixture of 2.5 ml of Tyrode's saline, 2.5 ml of heat-inactivated rat serum, 1 mg/ml of antibiotics in 50 ml glass culture bottles sealed with rubber stopper greased with silicone. Each bottle, containing no more than six embryos, is gassed for 4 min with a mixture of 25% oxygen, 5% carbon dioxide balanced with nitrogen. This is repeated half way through the 24 h culture period. The bottles are placed on horizontal rollers rotating at 30 rpm and housed in a 37 degrees C. incubator.

The serum is prepared from male Witstar rats. The animals are anaesthetised with Fluothane in a special chamber under a fume hood. Each animal is bled by puncturing the abdominal aorta with a needle and syringe kept on ice. The blood is transferred in 8 ml serum separating vacuettes and centrifuged at 5000 rpm for 30 min at 4 degrees C. The upper serum phase is then heat-inactivated at 56 degrees C. for 30 min, aliquoted and stores at −20 degrees C.

Preparation of Culture Bottles

Glass bottles are machine-washed and autoclaved. They are then filed with chromic acid and left overnight under a fume hood. The next day the bottles are rinsed with tap water followed by two washes with distilled water. The inside is coated with dimethyldichlorosilane and washed again twice with distilled water. They are then covered with aluminium foil and heat-sterilised at 120(C for 3 h. The rubber stoppers are kept in 70% Et OH until being autoclaved in paper bags.

Dosing Regimen for Antagonists

Dosing concentrations are established in a pilot dose-ranging study using logarithmic concentration steps to identify optimal dosage resulting in a reduction of Lac Z-expression in RAR-β2-transgenic mice.

Detection of β-galactosidase

Transgenic heterozygous mouse embryos at day 9.5 pc are fixed in 2% formaldehyde, 0.2% glutaraldehyde, 0.2% NP-40, 0.01% sodium deoxycholate in PBS for 1 h on ice. After washing with PBS, β-galactosidase activity is revealed by staining overnight at 37 degrees C. in the dark with 1 mg/ml Xgal, 5 mM $K_3Fe(CN)_6$, 5 mM $K^4Fe(CN)_6$, 2 mM $MgCl_2$ in PBS. After washing with PBS, the embryos are postfixed in 4% paraformaldehyde (PFA) in PBS for 1 h on ice.

Results

Transgenic mouse embryos (RARB2-RARE-LacZ) of 3-5 somite pairs are isolated from Dams and prepared for embryo cultures using standard protocols identical to those described in [Båvik, C., Ward, S. J., and Chambon, P. (1996). *Developmental abnormalities in cultured mouse embryos deprived of retinoic acid by inhibition of yolk-sac retinol binding protein synthesis. Proc. Natl. Acad. Sci.* 93, 3110-3114]. Embryos are exposed to P142 and control Ig (non-specific) dissolved in PBS to a final concentration of 1 mg/ml. This is added to the culture medium immediately prior to culture. After 24 hours the cultures are stopped and the embryos are pre-fixed for the beta-galactosidase staining. The beta-gal staining is performed according to standard protocols described in [Mendelsohn, C., Lohnes, D., De'cimo, D., Lufkin, T., LeMeur, M., Chambon, P. & Mark, M. (1994) Development 120, 2749-2771.] After the staining, the Lac Z staining intensity and expression domain is compared between P142-treated embryos and control Ig-treated embryos under a dissecting microscope.

Figure 12:
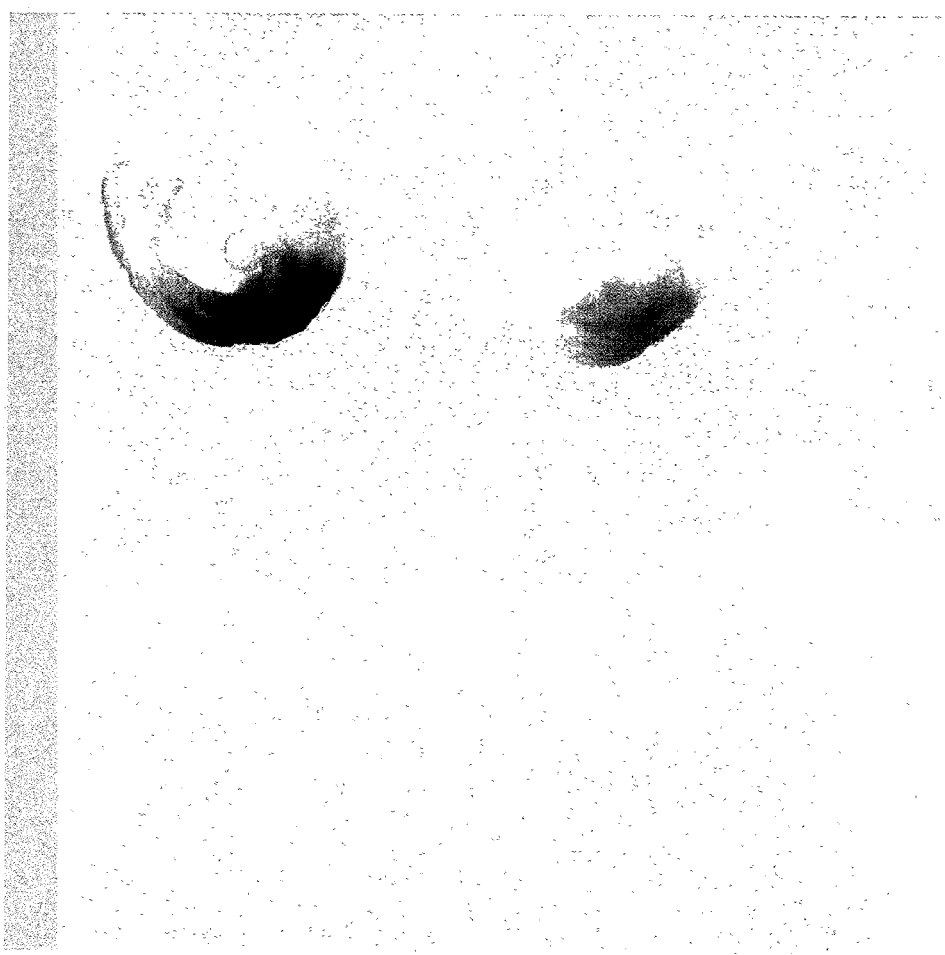
FIG. 12 shows the results of mouse embryos treated with anti-retinol binding protein receptor antibody P142 (light stain, right hand embryo) and control antibody (dark stain, left hand embryo).

The results of these experiments are shown in FIG. 12. The embryo on the right (light stain) is treated with P142 Ig, while the embryo on the left (dark stain) is treated with control Ig.

Embryos exposed to antibody show a reduction in lacZ staining overall and a change in the domain of staining (reduced posterior boundary), indicating a reduced retinoic acid level available for driving nuclear transcription, i.e. a functional Vitamin A deficiency. These results are similar to those found previously, following inhibition of RBP protein synthesis in the yolk sac [Båvik, C., Ward, S. J., and Chambon, P. (1996). *Developmental abnormalities in cultured mouse embryos deprived of retinoic acid by inhibition of yolk-sac retinol binding protein synthesis. Proc. Natl. Acad. Sci.* 93, 3110-3114].

Embryos show malformations previously described in retinoic acid- and vitamin A deficient animals, and reproduced the results reported in [Båvik, C., Ward, S. J., and Chambon, P. (1996). *Developmental abnormalities in cultured mouse embryos deprived of retinoic acid by inhibition of yolk-sac retinol binding protein synthesis. Proc. Natl. Acad. Sci.* 93, 3110-3114]. For instance, gross morphological and histological examination reveal a failure of lens induction. Similarly, myocardium walls appear thinner, indicting the possibility of precocious differentiation as previously reported [Kastner, P., Messaddeq, N., Mark, M., Wendling, O., Grondona, J. M., Ward, S., Ghyselinck, N. and Chambon, P. (1997). *Vitamin A deficiency and mutations of RXRα, RXRβ and RARα lead to early differentiation of embryonic ventricular cardiomyocytes. Development* 124, 4749-4758].

End-Point Assessment; Genetic and Morphologic

Genes known to be responsive to retinoic acid levels and those known to respond to conditions of retinoic acid-deficiency, for example TGFμ-1, Hoxa-1, RARβ-2 and CRAB-PII, are investigated for alteration in their protein and/or mRNA distribution. This is achieved by either quantitative RT-PCR or in situ hybridization (eg ISH; TGFβ1 expression by ISH; Hoxa1 expression by ISH; RARβ2). Probes for these genes are widely available (for example, commercially as plasmid constructs), or they may be cloned as described above.

Standard protocols for PCR are used to generate probes to analyze differentiation status. Probes are made against K1, K10 and CRABP II, using the following primer pairs:

```
K10
Primer sense 726-743         TGGAGGCTGACATCAACG
                             (SEQ ID NO: 13)
Primer antisense 1257-1278   TATTCAGTATTCTGGCACTCGG
                             (SEQ ID NO: 14)
Probe 726-1278 = 552 bp
Primer sense 195-217         CAGGTGGCTATGGAGGATTAGG
                             (SEQ ID NO: 15)
Primer antisense 687-708     ACCTCATTCTCATACTTCAGCC
                             (SEQ ID NO: 16)
Probe 195-708 = 513 bp K1
Primer sense 1046-1067       GCATCATTGCTGAGGTCAAGGC
                             (SEQ ID NO: 17)
Primer antisense 1613-1630   CACCTCCAGAACCATAGC
                             (SEQ ID NO: 18)
Probe 1046-1630 = 584 bp
Primer sense 422-441         GTGGTTATGGTCCTGTCTGC
                             (SEQ ID NO: 19)
Primer antisense 1046-1067   GCCTTGACCTCAGCAATGATGC
                             (SEQ ID NO: 20)
Probe 422-1067 = 645 bp CRABP II
Primer sense 214-235         ATGTGATGCTGAGGAAGATTGC
                             (SEQ ID NO: 21)
Primer antisense 466-487     TCGTTGGTCAGTTCTCTGGTCC
                             (SEQ ID NO: 22)
Probe 214-487 = 273 bp
```

Example 14

In situ Hybridisation

Production of DIG-Labelled RNA ISH Probes

Plasmids containing probe inserts are cut using an appropriate enzyme and DIG-labelled anti-sense (AS) ISH probes synthesised, using DIG-RNA labelling mix (Boehringer Mannheim 1277073). DIG-labelled sense probes are also transcribed for use as controls for non-specific hybridisation.

Collection of Tissue for ISH

Embryos are dissected in ice cold PBS and immediately fixed in 4% PFA for 2-4 hours at 4° C. with gentle shaking. They are then dehydrated in an ascending series of ethanol concentrations and cleared overnight in chloroform. The following day the tissue is embedded in paraffin wax. The tissue is cut into 7 µm sections and serially (6) mounted onto glass slides. The mounted sections are dried overnight at 42° C. For use as a positive control, adult mouse retina is also taken and treated in the same manner.

ISH Method

This is based on Komminoth (1996) method for detection of mRNA in tissue sections using DIG-labelled RNA probes. The sections are dewaxed in Xylene for 20 minutes and then rehydrated in a descending series of ethanol concentrations and washed with DEPC-treated $H_2O$.

Pre-Hybridisation

The sections re incubated twice with PBS for 5 minutes, followed by two 5 minute incubations with PBS containing 100 mM glycine (Sigma G4392). The sections are then treated with PBS containing 0.3% Triton X-100 (Boehringer Mannheim 789704) for 15 minutes. The sections are washed twice with PBS for 5 minutes. Sections are permeabilised for 15 minutes at 37° C. with TE buffer (BDH 103704U) containing 1 mg/ml Proteinase K (Boehringer Mannheim 1413783). The sections are post-fixed with 4% PFA at 4° C. for 5 minutes and then washed twice with PBS for 5 minutes. The sections are acetylated with 0.1 M TEA buffer containing 0.25% (v/v) acetic anhydride (BDH 100022M) for two 5 minute incubations. Sections re incubated, for a minimum of 10 minutes, with pre-hybridisation buffer (4×SSC containing 50% (v/v) deionised formamide (Fluka 47671)) at 37° C.

Hybridisation

The pre-hybridisation buffer is drained from the slides and each section is covered with 30 µl of hybridisation buffer (40% formamide, 10% dextran sulphate, 1×Denhardt's solution, 4×SSC, 10 mM DTT, 1 mg/ml yeast t-RNA, 1 mg/ml denatured and sheared salmon sperm DNA) containing 5-10 ng DIG-labelled RNA probe. As a further control, some slides are not exposed to a primary probe and are included in the ISH experiments to assess the level of non-specific (background) hybridisation by the anti-DIG. These sections are covered with hybridisation buffer. All slides are covered with a parafilm coverslip to prevent evaporation of the buffer, and the sections incubated overnight in a humid chamber at 42° C.

Post-Hybridisation

The coverslips are removed by immersing the slides in 2×SSC. The sections are washed in a shaking waterbath at 37° C., twice for 15 minutes with 2×SSC and twice with 1× SSC for 15 minutes. Any unbound RNA probe is removed by incubating the sections for 30 minutes in NTE buffer containing 20 mg/ml RNase A (Boehringer Mannheim 109142) at 37° C. The sections are then washed twice with 0.1×SSC at 37° C. for 30 minutes.

Immunological Detection

The sections are washed twice with Buffer 1 (100 mM Tris-HCl (pH 7.5), 150 mM NaCl) for 10 minutes on a shaking platform. The sections are covered with blocking solution (Buffer 1 containing 0.1% Triton X-100 and 2% normal sheep serum (Sigma S-2382)) for 30 minutes. The blocking solution is decanted and the sections are incubated for 2 hours in a humid chamber with Buffer 1 containing 0.1% Triton X-100, 1% normal sheep serum and sheep anti-DIG-alkaline phosphatase (Fab fragments) (Boehringer Mannheim 1093274) diluted 1:1000. Sections are then washed twice for 10 minutes with Buffer 1 before being incubated for 10 minutes with Buffer 2 (100 mM Tris-HCl (pH 9.5), 100 mM NaCl, 50 mM $MgCl_2$). During this last incubation a colour solution is prepared containing: 10 ml buffer 2, 80 ml NBT/BCIP stock solution (Boehringer Mannheim 1175041) and 1 mM levamisole (Sigma L9756). Each section is covered with 200 µl colour solution and the slides incubated in a humid chamber for 20 hours in the dark. The colour reaction is stopped by incubating the slides in Buffer 3 (10 mM Tris-HCl (pH 8.1), 1 mM EDTA) for 5-10 minutes. The slides are briefly dipped in distilled water before counterstaining the sections with 0.02% Fast Green FCF (Sigma F7258) for 2 min. Finally the sections are washed twice with tap water for 10 min before mounting with glycergel (Dako C563).

Fluorescein Detection

The sections are washed twice with Buffer 1 on a shaking platform for 10 minutes. The sections are covered with blocking solution (Buffer 1 containing 0.1% Triton X-100 and 2% normal sheep serum (Sigma S-2382)) for 30 min. The blocking solution is decanted and the sections are incubated for 3 hours in a humid chamber with Buffer 1 containing 0.1% Triton X-100, 1% normal sheep serum and sheep anti-DIG-fluorescein (Fab fragments) (Boehringer Mannheim 1207741) diluted 1:4-1:10. Sections are then washed four times with PBS, for 5 minutes. The sections are coverslipped using an anti-quenching agent (0.1% p-phenylenediamine (Sigma P), 10% PBS, 90% glycerol (Sigma G6279)), and slides stored in the dark at 4° C.

When in situ hybridisiation is carried out on embryos exposed to retinol binding protein receptor antagonists, down regulation of retinoid responsive gene expression is detected. Thus, we observe down-regulation of RARβ2, Hoxa1, and TGF-β1.

Example 15

Therapeutic Effect of Retinol Binding Protein Receptor Antagonism In Vivo—Placebo Controlled Trial of Anti-Retinol Binding Protein Receptor Antibodies Administered to Human Renal Cell Carcinoma Xenografted SCID Mice The severe combined immunodeficiency (SCID) mouse (scid,scid) is a strain of double mutant mouse with impaired lymphoid development and reduced natural killer cell activity. SCID mice have therefore been used as xenograft recipients to investigate the growth of implanted human tumours in vivo. The model has also been used to investigate the activity of anti-cancer therapies on the transplanted tumours. We have tested the effects of various retinol binding protein receptor antagonists on tumours transplanted into SCID mice.

Animals

The scid/scid mice used for these experiments are between the ages of 4 and 8 weeks. They are housed in microfilter cages. All cages, water and food are supplied after autoclaving. The cages are maintained in an air-conditioned and light-controlled (12 h/day) room and all handling and operations are done in a laminar flow hood.

Tumour Implantation

Fresh specimens of human renal cell carcinoma are obtained shortly after surgical resection. Informed consent for the use of discarded tumour tissue is obtained from the patients prior to the operation. The tumour samples for experimental use are removed from the main tumour mass by a consultant pathologist in order not to compromise histopathological assessment of the resection margins of the tumour. All of the tumour procurement protocols are approved by the South Sheffield local research ethics committee.

The fresh tumours are minced under sterile conditions in culture medium to 1.5 to 2.0 mm pieces and from these a single cell suspension is produced. The SCID mice are injected with $5 \times 10^5$ renal cell carcinoma cells subcutaneously into the right rear flank. Samples of the tumour cells are examined for quantification of retinol binding protein receptor expression level.

Anti-Retinol Binding Protein Receptor Antagonism

After the implanted tumours have grown to a palpable size below the skin surface (circa 5 mm$^3$) or to a larger size above the skin surface (circa 50 mm$^3$) the mice are injected via the tail vein with anti-retinol binding protein receptor monoclonal antibody produced as described above. A total of three injections are administered at weekly intervals and the experiment terminated six days after the last injection. A control group is injected at the same time points with the same volume of normal saline or purified antibodies from non-immunized animals. The size of the tumour appearing on the skin of a SCID mouse is measured in two dimensions with a caliper and the tumour volume is by the formula (width)$^2$ (length)/2. At the end of the experiment the mice are sacrificed, weighed and dissected. The tumours are removed and weighed. The dissected mice are examined for evidence of metastases. Immunohistochemistry of the resected tumours and other organs is performed.

Results

The average tumour volume in the mice injected with the anti-retinol binding protein receptor antibody is the same or reduced at the end of the experiment. In contrast in the control group injected with saline or purified antibodies from non-immunized animals the average tumour volume at the end of the experiment is thirty times that at the beginning. The efficacy of the treatment correlates positively with the expression level of retinol binding protein receptor in the tumor cells at time of implantation. Thus, injection of anti-retinol binding protein receptor antibody is capable of reducing tumour growth in vivo. The above experiment is repeated with retinol binding protein loop peptides with similar results.

Example 16

Therapeutic Effect of Retinol Binding Protein Receptor Antagonism In Vivo—Placebo Controlled Trial of Anti Retinol Binding Protein Receptor Monoclonal Antibody in SCID Mice Grafted with Human Psoriatic Lesional Skin SCID mice have also been used as recipients of xenografts of human psoriatic skin. This provides a good in vivo model of psoriasis in which the effect of new therapies can be evaluated. The effect of the anti retinol binding protein receptor antibody on SCID mice with transplanted psoriatic tissue is assessed after intravenous injection. This is because antibodies have too large a molecular weight to penetrate through the epidermal barrier. Animals used are as described above in the above Example.

Grafting of Psoriatic Tissue

Lesional psoriatic skin is excised with informed consent from the lower back of patients with chronic plaque psoriasis aged 40 to 60. The subcutaneous fat is separated from the dermis by sterile dissection. Grafts of psoriatic lesional skin are grafted onto SCID mice following the administration of a local anaesthetic.

Anti-Retinol Binding Protein Receptor Antagonism

After the psoriatic grafts have become established the mice are injected via the tail vein with the anti-retinol binding protein receptor monoclonal antibody. A total of three injections are administered at weekly intervals and the experiment terminated six days after the last injection. A control group is injected at the same time points with the same volume of w normal saline or purified antibodies from non-immunized animals.

Clinicopathological Assessments

The mice are examined and photographed at the end of the experiment in order to determine the clinical appearance of the grafted psoriatic tissue. It is found that the degree of psoriasis is reduced in animals which are injected with antibody, but not in animals injected with saline or purified antibodies from non-immunized animals. The above experiment is repeated with retinol binding protein loop peptides with similar results.

Example 17

In Vivo Demonstration of the Therapeutic Effect of Inhibitors of Human Retinol Dehydrogenase or Retinal Dehydrogenase Obtained in Two SCID Mouse Xenograft Models This Example describes a placebo controlled trial of inhibitors of human retinol dehydrogenase or retinal dehydrogenase administered to human renal cell carcinoma xenografted SCID mice. The SCID mouse, along with protocols for tumour implantation, has previously been described above. The SCID mice are injected with fresh specimens of human renal cell carcinoma or cultured HEK293, COS1 or COS7 cells.

The expression level of RBPr in samples of the renal carcinomas is examined by Western blot essentially as in Bavik et al., Characterization of a plasma retinol-binding protein membrane receptor expressed in the retinal pigment epithelium, J. Biological Chemistry 267: 23035-23042, 1992. The SCID mice are injected with $5 \times 10^5$ renal cell carcinoma cells subcutaneously into the right rear flank. The SCID mice are injected with $5 \times 10^5$ HEK293, COS1 or COS7 cells subcutaneously into the right rear flank After the implanted tumour cells have grown to a palpable size below the skin surface (circa 5 mm$^3$) or to a larger size above the skin surface (circa 50 mm$^3$) the mice are injected via the tail vein with the retinol dehydrogenase or retinal dehydrogenase inhibitors (final concentration 0.6 mM Carbenoxolone; 50 µM Phenylarsine; 10 µM Citral; 0.2 mM 4-Methylpyrazole; 15 µM Disulfiram; 10 µM Citral; 2 mM 3-Mercaptopropionic acid; or drug vehicle alone). A total of three injections are administered at weekly intervals and the experiment is terminated six days after the last injection. A control group is injected at the same time points with the same volume of normal saline. The size of the tumour appearing on the skin of a SCID mouse is measured in two dimensions with a caliper and the tumour volume was estimated by the formula (width)$^2$(length)/2. At the end of the experiment the mice are sacrificed, weighed and dissected. The tumours are removed and weighed. The dissected mice re examined for evidence of metastases. Immunohistochemistry of the resected tumours and other organs is performed.

The average tumour volume in the mice injected with the retinol dehydrogenase or retinal dehydrogenase inhibitors is the same or reduced at the end of the experiment. In contrast in the control group injected with saline the average tumour volume at the end of the experiment is thirty times that at the beginning. The efficacy of the treatment correlates positively with the expression level of RBPr in the tumor cells at time of implantation.

Example 18

Placebo Controlled Trial of Retinol Dehydrogenase or Retinal Dehydrogenase Inhibitors in SCID Mice Grafted with Human Psoriatic Lesional Skin SCID mice have also been used as recipients of xenografts of human psoriatic skin. This provides a good in vivo model of psoriasis in which the effect of new therapies can be evaluated. The effect of the retinol dehydrogenase or retinal dehydrogenase inhibitors is assessed after topical application. Mice and protocols are as described elsewhere.

Lesional psoriatic skin is excised with informed consent from the lower back of patients with chronic plaque psoriasis aged 40 to 60. The subcutaneous fat is separated from the dermis by sterile dissection. Grafts of psoriatic lesional skin are grafted onto SCID mice following the administration of a local anaesthetic.

After the psoriatic grafts have become established the retinol dehydrogenase or retinal dehydrogenase inhibitors are applied topically to the graft (0.6 mM Carbenoxolone; 50 µM Phenylarsine; 10 µM Citral; 0.2 mM 4-Methylpyrazole; 15 µM Disulfiram; 10 µM Citral; 2 mM 3-Mercaptopropionic acid; or drug vehicle alone). Retinol dehydrogenase or retinal dehydrogenase inhibitors are administered at daily intervals and the experiment terminated after 14 days of treatment. A control group is treated at the same time points with the vehicle alone. The mice are examined and photographed at the end of the experiment in order to determine the clinical appearance of the grafted psoriatic tissue. Samples of the graft are taken for histology.

Histological examination reveals normal human skin histology after treatment with the retinol dehydrogenase or retinal dehydrogenase inhibitors whereas control treated animals retain the psoriatic phenotype. Keratins 16 and 7/17 are detected immunohistochemically in control treated grafts but are absent in inhibitor treated graft.

Example 19

In Vivo Demonstration of the Therapeutic Effect of Inhibitors of Human Retinol Dehydrogenase or Retinal Dehydrogenase Obtained in a Mouse Tail Model The mouse tail model is a morphometry-based, sensitive and reproducible method for the quantitative evaluation of the effects of drugs on epithelial differentiation and induction of orthokeratosis. Orthokeratosis is determined by measuring the horizontal length of the fully developed granular layer within an individual scale in relation to its total length. (Jarret and Spearman, Histochemistry of the skin. London University Press, 1964; Sebök B, et al., Tazarotene induces epidermal cell differentiation in the mouse tail test used as an animal model for psoriasis, Skin Pharmacol. Appl. Skin Physiol. 13:285-91, 2000).

Animals: The Balb/C mice used for these experiments are between the ages of 4 and 8 weeks. Mice are topically exposed to retinol dehydrogenase or retinal dehydrogenase inhibitors (0.6 mM Carbenoxolone; 50 µM Phenylarsine; 10 µM Citral; 0.2 mM 4-Methylpyrazole; 15 µM Disulfiram; 10 µM Citral; 2 mM 3-Mercaptopropionic acid; or drug vehicle alone). The inhibitors are applied topically to the proximal tail at daily intervals and the experiment terminated after 14 days of treatment. A control group is treated at the same time points with the vehicle alone.

The degree of orthokeratosis of an individual scale is defined as the percentage ratio of: the horizontal length of the fully developed granular layer within an individual scale divided by the horizontal length of that scale. Statistical analysis of the degree of orthokeratosis reveals that treatment with retinol dehydrogenase or retinal dehydrogenase inhibitors are significantly ($p<0.05$) more effective than control treatment.

Each of the applications and patents mentioned above, and each document cited or referenced in each of the foregoing applications and patents, including during the prosecution of each of the foregoing applications and patents ("application cited documents") and any manufacturer's instructions or catalogues for any products cited or mentioned in each of the foregoing applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention will now be further described by the following additional numbered paragraphs.

1. A method of treating a patient suffering from a hyperproliferative disorder or photoageing, which method comprises lowering the endogenous level or activity of retinoic acid (RA) in a cell of the patient.
2. A method according to paragraph 1, in which the endogenous level of retinoic acid is lowered in a hyperproliferating cell or a cell suffering from photoageing of said patient.
3 A method according to paragraph 1, in which the endogenous level of retinoic acid in the cell is lowered to an extent that cell proliferation is reduced or abolished, and/or to an extent that cell differentiation is activated or enhanced.
4. A method according to any preceding paragraph, in which the method comprises inhibiting the uptake of retinol by a retinol binding protein receptor (RBPr).
5. A method according to any preceding paragraph, in which the method comprises antagonising one or more elements of a pathway which leads to biosynthesis of retinoic acid.
6. A method according to paragraph 5, in which the method comprises antagonising a retinol dehydrogenase (RDH), an alcohol dehydrogenase (ADH), or a retinal dehydrogenase (RalDH).

7. A method according to paragraph 6, in which the method comprises antagonising a retinol dehydrogenase enzyme selected from the group consisting of: RoDH1, RoDH2, RoDH3, RoDH4, CRAD1, CRAD2, RDH5 and retSDR1, or an alcohol dehydrogenase selected from the group consisting of: ADH1, ADH2 and ADH4, or a retinal dehydrogenase enzyme selected from the group consisting of: ALDH1, ALDH6, RALDH2 and ALDH-t.

8. A method according to any preceding paragraph, in which the antagonist of the retinol binding protein receptor is selected from the group consisting of:
   (a) an immunoglobulin capable of binding to retinol binding protein receptor;
   (b) a peptide comprising a sequence from a receptor binding region of retinol binding protein;
   (c) a peptide comprising a sequence K29-Q38, G59-A71 or M88-D102 of retinol binding protein;
   (d) a peptide comprising a heterodimer consisting of peptides G59-A71 and M88-D102 of retinol binding protein;
   (e) an antisense molecule capable of inhibiting the expression of retinol binding protein receptor;
   (f) an antisense RNA, an antisense DNA, an antisense oligonucleotide;
   (g) carbenoxolone, phenylarsine oxide, citral, 3,7-dimethyl-2,6-octadienal, 4-methylpyrazole and disulphiram.

9. A method of treating a patient suffering from a hyperproliferative disorder or photoageing, which method comprises administering to the patient a compound capable of interfering with the biosynthesis of retinoic acid.

10. A method according to paragraph 9, in which the compound is capable of inhibiting the uptake of retinol into the cell, or in which the compound is an inhibitor of an enzyme involved in the biosynthesis of retinoic acid.

11. An agent capable of lowering the endogenous level of retinoic acid in a cell for use in a method of treating a hyperproliferative disorder or photoageing in a patient.

12. A retinol binding protein receptor antagonist for use in a method of treatment of a patient suffering from a hyperproliferative disorder or photoageing.

13. An inhibitor of retinoic acid synthesis for use in a method of treatment of a patient suffering from a hyperproliferative disorder or photoageing.

14. An agent or antagonist according to paragraph 11, 12 or 13, in which the antagonist is capable of inhibiting uptake of a retinoic acid precursor or inhibiting biosynthesis of a retinoic acid precursor.

15. An antagonist according to any of paragraphs 11 to 14, which is selected from the group consisting of: (a) to (g) of paragraph 8.

16. A method, agent or antagonist according to any preceding paragraph, in which the hyperproliferative disorder comprises psoriasis, acne vulgaris, acne rosacea, actinic keratosis, solar keratoses, squamous carcinoma in situ, the ichthyoses, hyperkeratoses, disorders of keratinization such as Darriers disease, palmoplanter keratodermas, pityriasis rubra pilaris, epidermal naevoid syndromes, erythrokeratoderma variabilis, epidermolytic hyperkeratoses, nonbullous ichthyosiform erythroderma, cutaneous lupus erythematosus and lichen planus.psoriasis, acne vulgaris, or cancer.

17. A method for identifying an antagonist of retinol binding protein receptor, the method comprising contacting a cell with expresses retinol binding protein receptor with a candidate compound and determining whether the level of retinoic acid in said cell is lowered as a result of said contacting.

18. A method for identifying a compound capable of lowering the endogenous level of retinoic acid in a cell, which method comprises contacting a cell which expresses a retinol binding protein receptor with a candidate compound, and determining whether the level of retinoic acid in said cell is lowered as a result of said contacting.

19. A method for identifying a compound capable of inhibiting the interaction between a retinol binding protein and a retinol binding protein receptor, which method comprises contacting a retinol binding protein receptor, or a fragment thereof capable of binding retinol binding protein, with a candidate compound in the presence of retinol binding protein and determining whether the levels of retinol binding protein binding to the receptor are reduced.

20. A compound or antagonist identified by a method according to any of paragraphs 16 to 19.

21. A method of preventing proliferation of a cell, the method comprising lowering the endogenous level or activity of retinoic acid (RA) in the cell.

22. A method according to paragraph 21, in which the cell is a hyperproliferative cell.

23. A method according to paragraph 21 or 22, in which the cell is contacted with a compound capable of interfering with the biosynthesis of retinoic acid.

24. A method according to paragraph 21, 22 or 23, in which the method comprises inhibiting the activity of a retinol binding protein receptor of the cell.

25. A method according to any of paragraphs 21 to 24, in which the cell is contacted with an antagonist of a retinol binding protein receptor.

26. A method according to any of paragraphs 21 to 25, in which the cell is contacted with an antagonist of one or more elements of a pathway which leads to biosynthesis of retinoic acid.

27. A method according to any of paragraphs 21 to 26, which results in cell differentiation.

28. A method of activating a differentiation program in a cell, the method comprising contacting the cell with a compound capable of interfering with the biosynthesis of retinoic acid.

29. A method of treating or alleviating the symptoms of a patient suffering from a disorder, in which the disorder is a retinoid sensitive disorder treatable by administration of retinoids, or in which the disorder corresponds to a side effect of administration of pharmacological levels of retinoid, which method comprises reducing the endogenous level or activity of retinoic acid (RA) in a cell of the patient.

30. A method according to paragraph 29, in which the retinoid sensitive disorder is a disorder which is treated or whose symptoms are alleviated by administration of higher than physiological levels of retinoid to the patient.

31. A method of treating or alleviating the symptoms of a patient suffering from a disease characterised by ectopic, over- or otherwise abnormal expression of a retinoic acid receptor response element (RARE) responsive gene, a vitamin D response element (VDRE) responsive gene, a thyroid hormone receptor response element responsive gene or a peroxisome proliferator-activated receptor (PPAR) response element responsive gene, which method comprises reducing the endogenous level or activity of retinoic acid (RA) in a cell of the patient.

32. A method of treating or alleviating the symptoms of a patient suffering from a disease characterised by an imbalance between proliferation and differentiation, which method comprises reducing the endogenous level or activity of retinoic acid (RA) in a cell of the patient.

33. A method according to any of paragraphs 29 to 32, the method comprising inhibiting the activity of a retinol binding protein receptor in cells of the patient, and/or inhibiting the biosynthesis of retinoic acid in the cells of the patient.

34. A pharmaceutical composition suitable for treating a patient suffering from a hyperproliferative disorder or photoageing, comprising a therapeutically effective amount of a compound capable of reducing the endogenous level of retinoic acid in a cell, together with a pharmaceutically acceptable carrier or diluent.

35. A pharmaceutical composition suitable for treating a patient suffering from a hyperproliferative disorder or photoageing, comprising a therapeutically effective amount of a retinol uptake inhibitor together with a pharmaceutically acceptable carrier or diluent.

36. A pharmaceutical composition suitable for treating a patient suffering from a hyperproliferative disorder or photoageing, comprising a therapeutically effective amount of a retinoic acid synthesis inhibitor together with a pharmaceutically acceptable carrier or diluent.

37. A method for identifying a compound capable of reducing endogenous retinoic acid levels, comprising contacting a cell with a candidate compound, and determining whether the level of retinoic acid within the cell is reduced.

38. A method for identifying a compound capable of inhibiting retinol dehydrogenase, comprising exposing a cell expressing a retinol dehydrogenase to a compound and determining whether the levels of retinal within the cell are reduced.

39. A method for identifying a compound capable of inhibiting retinal dehydrogenase, comprising exposing a cell expressing a retinal dehydrogenase to a compound and determining whether the levels of retinoic acid within the cell are reduced.

40. A method of treating a patient suffering from a disease, disorder or condition, which method comprises lowering the endogenous level or activity of retinoic acid (RA) in a cell of the patient, in which the disease, disorder or condition is selected from the group consisting of: Viral infection, HPV, HIV, HSV, HCV infection, warts, post-operative scarring, hypertrophic and keloid scarring, a disorder of melanogenesis, a disorder of pigmentation, enhanced or compromised epidermal barrier function, a disorder of bone growth, bone fracture, osteoporosis, hyperlipidaemia, hepatotoxicity, cirrhosis, hepatitis infection, cutaneous irritation, alopecia, a disorder of fertility, a disorder of spermatogenesis, a disorder of egg implantation, depression, seasonal affective disorder, atherosclerosis and a disorder of angiogenesis.

APPENDIX 1

VITAMIN D RESPONSE ELEMENT RESPONSIVE GENES AND RETINOIC ACID RESPONSE ELEMENT RESPONSIVE GENES

| | Accession Number | |
|---|---|---|
| | Human | Mouse |
| Vitamin D target genes (Vitamin D Response Elements) | | |
| a3-integrin | XM 008431 | NM 013565 |
| b3-integrin | XM 012636 | NM 016780 |
| c-fos | AF 111167 | — |
| CYP24cip1/waf1 | U 03106 | U 24173 |
| vitamin D receptor | NM 000376 | NM 009504 |
| Retinoic acid target genes (Retinoic Acid Response Element) | Hu man | Mouse |
| eNOS (nitric oxide synthase) | — | — |
| iNOS (nitric oxide synthase) | AF 049656 | NM 010927 |
| platelet-activating facor receptor, human (PAFR) (cDNA encoding a putative DNA-binding protein of the (PTB) domain-contain protein | XM 001857 | — |
| (t-PA) transcription of the human tissue-type plasminogen activator gene | M 15518 | NM 008872 |
| 0ct:3 | AB 011082 | — |
| 0ct:4 | AB 010438 | — |
| 2a | AF 178948 | — |
| 2b | AF 179896 | — |
| 2c | AF 179897 | — |
| 2d | AF 179898 | — |
| 2e | AF 179899 | — |
| 71 Numb (membrane-associated, phosphotyrosine binding- | AF 015040 | U 70674 |
| Acetylated low density lipoprotein | — | — |
| Acetylcholine (Ach) | | |
| ACS (acyl-CoA synthetase) | — | — |
| Acyl-coenzyme A: cholesterol acyltransferase-I (ACAT-1) protein | NM 003101 | — |
| ADD1 (a basic helix-loop-helix leucine zipper-type transcription factor) | XM 003404 | NM 013457 |
| Adipsin | XM 009262 | NM 013459 |
| AFP (alpha-fetoportein) | NM 002777 | NM 011178 |
| Albumin | NM 000477 | — |
| aldoketoreductase family1, member C1 (HAKRe) | NM 030611 | — |
| Alpha (8)-integrin | XM 042813 | — |
| Alpha 1 (I) procollagen | NM000088 | — |
| Alpha 1,3 GT (UDP-Gal:beta-D-Gal alphaI1,3-galactosyltransferase) | — | — |
| Alpha Fetoprotein (AFP) | XM 031318 | AH 001842 |

APPENDIX 1-continued

VITAMIN D RESPONSE ELEMENT RESPONSIVE GENES AND RETINOIC ACID RESPONSE ELEMENT RESPONSIVE GENES

| | Accession Number Human | Mouse |
|---|---|---|
| alpha form | XM 034737 | NM 011101 |
| AML 2, a member of the acute myelogenous leukemia | — | U85644 |
| Androgen-binding protein (ABP) | — | NM 013473 |
| Annexin VIII | M 81844 | NM 013473 |
| AP 2 alpha | NM 003220 | |
| AP-2 gamma | — | BC 0037798 |
| Apolipoprotein AI | XM 052108 | NM 009692 |
| Apolipoprotein CIII | XM 052117 | — |
| Apolipoprotein D (apo D) | XM 003067 | NM 007470 |
| Apolipoprotein(a) Apo(a) | BC 005380 | X 64262 |
| Aryl hydrocarbon receptor | XM 004988 | AF 325111 |
| ATP-binding cassette transporter 1 (ABC1) | NM 005502 | NM 013454 |
| B cell CLL lymphoma (Bcl-2) variant alpha | NM 000633 | M16506/L31532 |
| B cell CLL lymphoma (Bcl-2) variant beta | NM 000657 | AH 001858 |
| b-myb | XM 11125 | NM 009263 |
| B94 (TNFalpha-induced protein 2) | NM 006291 | NM 009396 |
| Bcl2 | — | — |
| Bdm-1 | — | — |
| beta 1 | XM 005297 | NM 007843 |
| Beta 1,4 galactosyltransferase gene | NM 001497 | — |
| Beta 1-adrenergic receptor | XM 0005827 | NM 007419 |
| beta 2 | XM 031794 | NM 010030 |
| Beta 2-integrin genes (CD18) | XM 004285 | — |
| beta 3 | — | NM 013756 |
| beta 4 | — | NM 019728 |
| beta 5 | — | AF 318068 |
| beta form | XM 047186 | NM 008855 |
| Beta(1)-integrin subunit | — | NM 010330 |
| Beta-2 microglobulin | NM 002350 | M 57696 |
| Beta-amyloid precursor protein (beta APP) | NM 000484 | NM 007471 |
| Beta-galactoside-binding lectin (14K type) | X 14829 | U 55060 |
| biglycan | XM 010384 | NM 007542 |
| Bmp-2 | AF 040249 | NM 007553 |
| Bone morphogenic protein (BMP-7) | XM 012943 | NM 007557 |
| Bone morphogenic protein 2 | XM 009629 | NM 007553 |
| Bone morphogenic protein 4 | XM 051690 | XNM 007554 |
| BP (a secreted binding protein for fibroblast growth factors) | — | — |
| Brn-3.2 (homology of mammalian POU gene) | XM 003736 | NM 011938 |
| C-erbB-2 | AH 001455 | — |
| C-erbB-3 | AH 009647 | — |
| C-fos | K 00650 | V 00727 |
| C-Jun | — | — |
| C-kit (receptor typrosin kinase) | X 06182 | Y 00864 |
| C-myc | XM 015267 | NM 011146 |
| C/EBP epsilon | — | — |
| caesin kinase II alpha subunit | X 69951 | — |
| caesin kinase II beta subunit | — | X 56502 |
| Calbindin (28K) | XM 005308 | NM 009788 |
| Carbonic anhydrase II gene | XM 045077 | NM 009801 |
| Cartilage-derived retinoic acid-sensitive protein (CD-RAP) | — | NM 019394 |
| Cathespin-L | XM 041601 | NM 009984 |
| CD14 | NM 005529 | NM 008305 |
| CD23 | XM 006302 | — |
| CD34 (leukosialin, sialophorin) | XM 002007 | U49383 |
| CD38 antigene | XM 007650 | NM 009735 |
| CD43 (leukosialin, sialophorin, GL115) | XM 018290 | NM 009259 |
| Cek-8 (Eoh-related receptor tyrosine kinase gene) | — | — |
| CerbB-4/HER4 | — | — |
| Ceruloplasmin (ferroxidase) | XM 051423 | NM 007752 |
| ChAT (choline acetyltransferase) | XM 0011847 | — |
| Chondromodulin-I | — | — |
| chorionic gonadotrophin hormone | — | — |
| Chromogranin B | XM 009625 | NM 007694 |
| Collagenase-1 (matrix metalloproteinase-1 (MMP-1) | XM 006270 | — |
| collagenase-3 | XM 006274 | NM 008607 |
| Connexin 43 | XM 027460 | — |
| Cornifin (small proline rich protein 1B/SPRR1B) | XM 048112 | NM 009265 |
| COUP-TFI | XM 003879 | NM 010151 |
| COUP-TFII | NM 021005 | NM 009697 |
| CRBP II (cellular retinol-binding protein type II | U 13831 | X 74154 |
| CRIPTO | AF 312925 | NM 007685 |
| Cyclin D1 | M 64349 | — |
| Cyclin D1 | NM 001758 | NM 007631 |
| Cyclin D2 | AH 002631 | |
| Cyclin D3 | M 92287 | |

APPENDIX 1-continued

VITAMIN D RESPONSE ELEMENT RESPONSIVE GENES AND RETINOIC ACID RESPONSE ELEMENT RESPONSIVE GENES

| | Accession Number | |
|---|---|---|
| | Human | Mouse |
| Cyclin D3 | XM 036381 | NM 007632 |
| Cyclin-dependent kinase 3(Cdk3) | XM 008130 | — |
| Cyclooxygenase-2 (Cox-2) | XM 001734 | NM 011198 |
| CYP19 (produce aromatase P450) | XM 007568 | NM 007810 |
| DEAD box protein p72 | U 59321 | — |
| Decorin | XM 0112239 | NM 007833 |
| Defensin | | |
| delta form | XM 003106 | NM 011103 |
| Dopamin D2 | — | — |
| Dual specificity tyrosine (Y) phosphorylation regulated kinase 4 (DYRK4) | XM 034551 | — |
| E3 | — | — |
| Early growth response 1 (EGR1) | NM 001964 | NM 007913 |
| Early retinoic acid transcipt-1 alpha (Era-1) | — | NM 009016 |
| Early retinoic acid transcipt-1 beta (Era-1) | — | NM 009017 |
| Early retinoic acid transcipt-1 gamma (Era-1) | — | NM 009018 |
| EC1 | — | — |
| Elastin | XM 004897 | NM 007925 |
| Embigin | XM 004063 | AH 003568 |
| Endolyn (CD164) | AF 263279 | AF 299345 |
| Engrailed 1 | XM 002479 | NM 010133 |
| Engrailed 2 | XM 001427 | NM 010134 |
| eosinophil major protein 2 (MBP2) | — | AF 202533 |
| EphrinB1 receptor tyrosine kinase ligand | — | — |
| epidermal growth factor receptor | — | NM 007912 |
| Epithelin | — | — |
| epsilon form | XM 010814 | NM 011104 |
| Ets 1 | XM 009073 | X 53953 |
| Eurkaryotic elongation factor alpha 1(EF-1 alpha) | NM 001402 | XM 009445 |
| Eurkaryotic elongation factor alpha 2(EF-1 alpha) | — | NM 007906 |
| Eve1 (an even-skipped gene) | — | — |
| Evx2 (an even-skipped gene) | AH 002690 | — |
| F52/MacMARCKs | — | X61399 |
| FABP5 (psoriasis-associated fatty acid-binding protein) | XM 002542 | NM 008275 |
| FATP-1 (fatty acid transport protein) | — | NM 011977 |
| Fgf-3 | — | NM 008007 |
| Fgf4 | XM 012011 | NM 010202 |
| Fibroblast growth factor-4 (Fgf-4) | — | U 43515 |
| Fibroblast growth factor-8 (Fgf-8) | NM 006119 | Z 48746 |
| Fibronectin | | |
| FPR1 (formyl peptide receptor1) | XM 009375 | NM 013521 |
| Fra-1 | — | — |
| Fructose-1,6-bisphosphatase (FBPase) | AH 006619 | — |
| Galectin-1 | XM 009971 | NM 008495 |
| Galectin-1 (gal-1) a galactoside-binding protein | XM 038715 | NM 008495 |
| Galectin-3 | XM 007333 | — |
| GATA-4 | NM 002052 | NM 008092 |
| Gb110 | NM020963 | X 75819 |
| Gbx1 | — | — |
| GDAP1 (ganglioside-induced differentiation-associated protein 1) | XM 005273 | NM 010267 |
| GDAP10 (ganglioside-induced differentiation-associated protein 10) | — | NM 010268 |
| gelatinase A | BC 002576 | — |
| gelatinase B | BC 006093 | X 72795 |
| Gelatinase B (MMP-9) | XM 009491 | NM 013599 |
| Gene 33 (Mig-6) | XM 010612 | — |
| Ghox-7 (chicken homeobox-containing gene) | — | — |
| Glial cell line-derived neurotrophic factor (GDNF) | NM 000514 | NM 010275 |
| Glucose transporter protein type 3 (GLUT 3) | — | X 69698 |
| Gont 1 (a Notochord family homeobox gene) | — | — |
| Goosecoid | XM 009832 | NM 010351 |
| GPRK6 (G-protein-coupled receptor kinase) | NM 001444 | NM 010634 |
| GPT (UDP-N-acetylglucosamine:dolichyl-phosphate- | XM 051420 | — |
| Gpx2 (encoding selenium-dependent glutathione peroxidase) | AF 199441 | U 62658 |
| GRIM-19 (retinoid-interferon-induced mortality-19) | AF 286697 | AF 286698 |
| Gs alpha (a subunit of the stimulatory coupling protein of adenylate cyclase) | — | |
| H1 | XM011804 | — |
| H2 | XM005512 | — |
| H218 (guanine nucleotide-binding protein (G-protein)-coupled receptor | — | — |
| HAIR-62 (Hoxal regulated-62) | — | — |
| HBNF (heparin-binding neurite-promoting factor) | NM 002825 | |
| HBV (human hepatitis B virus) | X 74497 | — |
| hck | — | — |

APPENDIX 1-continued

VITAMIN D RESPONSE ELEMENT RESPONSIVE GENES AND RETINOIC ACID RESPONSE ELEMENT RESPONSIVE GENES

| | Accession Number | |
|---|---|---|
| | Human | Mouse |
| Heat stable antigen | — | X 53825 |
| Heparin-binding EGF like growth factor (HB-EGF) | — | AH 006539 |
| hepatic nuclear factor 1 (HNF1) | XM 012120 | — |
| hepatic nuclear factor 4 (HNF4) | XM 029795 | — |
| HMGI(Y) | XM 004327 | — |
| HNF-3alpha (hepatocyte nuclear factor-2alpha) | XM 007300 | — |
| Homeobox B2 (HOX B2) | NM 002145 | — |
| Homeobox D4 (HOXD4) | XM 042818 | NM 014621 |
| Homo sapiens dipeptidylpeptidase IV (DPP4/CD26) | XM 002211 | NM 010074 |
| Hox 3D | — | — |
| Hox a 5 | NM 000612 | NM 010514 |
| Hox A1 | NM 005522 | — |
| Hox b-5 | NM 002147 | NM 008268 |
| Hox D13 | NM 003239 | NM 009368 |
| Hox-4.2 (Homolog to human HOX4B) | — | — |
| Hoxa4 | XM 004917 | — |
| Hoxb-8 | — | — |
| HSD17B1 (17 beta-hydroxsteroid dehydrogenases) | XM 012644 | NM 010475 |
| HSP90 | — | — |
| HuD (RNA binding protein) | — | D 31953 |
| Human 1,25-dihydroxyvitamin D3 receptor (hVDR) | NM 000376 | NM 009504 |
| Human A1 (a Bcl-2 homologue) | — | — |
| Human BRE gene (brain and reproductive organs gene) | AF 015767 | |
| Human growth-differentiation factor 3 (hGDF3) | XM 006615 | — |
| Human retinal fascm gene (FSCN2) | — | — |
| ICAM-1 (human intercellular adhesion molecule-1) | NM 000201 | AH 001921 |
| IDE (insulin-degrading enzyme) | XM 005890 | NM 031156 |
| IGF II (insulin-like growth factor II) | XM 011971 | — |
| IGFBP insulin-like growth factor-binding protein 6 | XM 012161 | NM 008344 |
| IGFBP-3 (insulin-like growth factor binding protein 3) | X64875 | NM 008343 |
| IGFBP-5 (insulin-like growth factor binding protein 5) | NM 000599 | NM 010518 |
| IL-15 (interleukin-15) | XM 003529 | NM 008357 |
| Importin alpha 1 | — | — |
| Importin alpha 2 | — | — |
| Importin alpha 3 | XM 011015 | NM 008466 |
| Importin alpha 4 | XM 007195 | NM 008467 |
| Importin alpha 5 | XM 032659 | — |
| Importin alpha 6 | XM 004308 | NM 008468 |
| Importin alpha 7 | XM 034510 | — |
| Inositol triphosphate (InoP3) | — | — |
| Int-2 | XM 002498 | — |
| Interacellular fibronectin (FN) | M 10905 | — |
| interferon-gamma | XM 052526 | — |
| interstial collgagenase | XM 006270 | — |
| Involucrin | XM 001677 | NM 008412 |
| j-acetylglucosamine-1 phosphate transferase | | |
| J6 (a heat shock protein) | XM 017384 | NM 010810 |
| JEM-1 | XM 001573 | — |
| Jun N-terminal kinase 1 (JNKKI) | U 17743 | — |
| Jun N-terminal kinase 2 (JNKK2) | AF 022805 | — |
| Krox-24 | — | — |
| KS:CS-PG (large keratan sulfate/chondroitin- | — | — |
| Lactate dehydrogenase B | XM 050073 | NM 008492 |
| Laminin | | |
| Lefty-1 | — | AJ000082 |
| Leptin | NM 000230 | NM 008493 |
| leptin | XM 045426 | NM 008493 |
| Leukocyte adherence protein beta subunit | — | — |
| Low-affinity nerve growth factor receptor | — | — |
| Low-affinity nerve growth factor receptor (LNGFR) | XM 016142 | — |
| Lyna | XM 009806 | NM 008404 |
| Lynb | XM 009539 | NM 010407 |
| Lysozyme | XM 006858 | NM 017372 |
| Mac 25 | | |
| Malic enzyme 1 | — | — |
| Malic enzyme 2 | XM 003593 | NM 007646 |
| Malic enzyme 3 | XM 004367 | — |
| MAPK (mitogen-activated protein kinase) | — | — |
| matrilysin 1 (MMP7) | NM 006206 | M 84607 |
| matrilysin 2 (MMP26) | X 13293 | X 70472 |
| mDab2 (mouse disabled 2) | AF 071062 | — |
| Meis 1 | X 14445 | Y 00848 |
| Meis 2 (homeodox gene) | — | L 157343 |
| MEK | — | — |
| Mel1/EAT | L02533 | — |

APPENDIX 1-continued

VITAMIN D RESPONSE ELEMENT RESPONSIVE GENES AND RETINOIC ACID RESPONSE ELEMENT RESPONSIVE GENES

| | Accession Number | |
|---|---|---|
| | Human | Mouse |
| Membrane-spanning mucin ASGP(Muc4) | XM 010936 | AF161256 |
| MGP (Matrix Gla protein) vitamin K dependent | XM 006585 | — |
| MHC class I (major histocompatibility complex) | | M 57697 |
| Microfibril-associated gylcoprotein 2 | NM 003480 | — |
| Midkine (neurite growth promoting factor 2) | XM 006297 | NM 010784 |
| MK gene (embyronic cytokine gene) | — | — |
| Mouse TRH gene | NM 007117 | NM 009426 |
| MROR | — | S 82720 |
| MRP-8 9migration inhibitory factor-related protein-8) | X 06234 | — |
| MSMP-30 | — | — |
| Mst-1 | — | — |
| Msx 1 | XM 003469 | NM 010835 |
| Msx 2 | NM 002449 | NM 013601 |
| MT78 (homology to human thioredoxin) | — | — |
| MUC4 (mucin gene) | XM 010936 | AF 296636 |
| MUC8 | U 14383 | — |
| Mucin (Muc5AC) | AJ001403 | L42292 |
| Mucin 2 (MUC2) gene | NM 002457 | AF 221746 |
| Murine epididymal retinoic acid binding protein (mE-RABP) | — | NM 007947 |
| Murine homolog of COUP-TF1 | — | X 74134 |
| Murine Hoxb-1 | — | — |
| Murine Ptx (paired-like class of homeobox gene) | — | — |
| mWnt 8 | — | — |
| Myeloblastin | AB 005999 | U 43509 |
| Myeloperoxidase gene (MPO) | XM 008160 | NM 010824 |
| MyoD1 | — | — |
| Myogenin | — | NM 031189 |
| N-bhh (newt homologue of Xenopus banded hedgehog | — | — |
| N-myc | AF 320053 | X 03919 |
| N52 | — | — |
| Ncx (Enx, hox11L1) | XM 035224 | — |
| Nedd-1 | — | D 10712 |
| neural cell adhesion molecule 1 (NCAM1) | XM 041414 | — |
| neural cell adhesion molecule 2 (NCAM2) | XM 009705 | NM 010954 |
| Neurofibromin 1 | NM 000267 | AH 002052 |
| Neurofibromin 2 | NM 000268 | — |
| Neuronal cadherin (cadherin 2, type I) | XM 008776 | NM 007664 |
| Neuropeptide Y (NPY) | XM 004941 | — |
| Neurturin (NTN) | NM004558 | NM 008738 |
| neutrophil collagenase | XM 006273 | NM 008611 |
| Newt connective tissue growth factor | — | — |
| Nm23-H1 (a metastasis suppressor gene) | X 75598 | — |
| Notch 1 | AF 308602 | L 02613 |
| Notch 2 | NM 024408 | D 32210 |
| Notch 3 | NM 000435 | NM 008716 |
| Novel retinal pigment epithelial gene (NORPEG) | NM 015577 | — |
| Nucleophosmin/B23 | XM 018324 | NM 008722 |
| NvKJI (type II keratin) | — | — |
| Oct6 (octamer binding factor) | — | — |
| OPN (osteopontin) | | |
| ornithine aminotransferase (OAT) | XM 043659 | NM 016978 |
| Osteocalcin (bone gamma-carboxyglutamate protein) | XM 002069 | NM 031368 |
| Otx 1 | — | — |
| oxidized LDL receptor (LOX-1) | AF 035776 | AF 303744 |
| P21ras-GTP | — | — |
| P27 (cyclin-dependent kinase (cdk) inhibitor | AF 247551 | U 09968 |
| P300 (E1A-associated 300 KDa protein) | XM 010013 | — |
| p38 | — | — |
| P53 | XM 043212 | — |
| PACAP1 (pituitary adenylate cyclase activating peptide1) | XM 012740 | NM 009625 |
| PAF receptor (human platelet-activity factor) | D 10202 | AF 004858 |
| Patched | XM 005574 | NM 008957 |
| Pax 6 | XM 010880 | NM 010789 |
| Pax-2 a | NM 003987 | XM 011933 |
| Pax-2 b | NM 000278 | — |
| Pax-2 c | NM 003988 | — |
| Pax-2 d | NM 003989 | — |
| Pax-2 e | NM 003990 | — |
| PDGF alpha receptor | L 19182 | AB O12886 |
| PEA3 (polyomavirus enhancer activator 3) | — | NM 008815 |
| Perlecan | NM 002396 | — |
| PGD 2 synthetase (prostaglandin D2 synthetase) | XM 003695 | NM 010728 |
| PGD2 synthetase (PGD-S) | — | — |
| Phosphoenolpyruvate carboxykinase (PPCK) mitochondrial | XM 007298 | — |
| Phosphoenolpyruvate carboxykinase (PPCK) soluble | XM 009672 | NM 011044 |

APPENDIX 1-continued

VITAMIN D RESPONSE ELEMENT RESPONSIVE GENES AND RETINOIC ACID RESPONSE ELEMENT RESPONSIVE GENES

| | Accession Number Human | Mouse |
|---|---|---|
| Phospholipase C beta 2 | XM 007610 | AF022802 |
| Phospholipase C beta 3 | XM 012108 | NM 008874 |
| placental lactogen hormone variant 1 | NM 020991 | — |
| placental lactogen hormone variant 2 | NM 022644 | — |
| placental lactogen hormone variant 3 | NM 022645 | — |
| placental lactogen hormone variant 4 | NM 022646 | — |
| Platelet-derived growth factor-BB(PDGF-BB) | — | — |
| PPAR (peroxisome proliferator-activated receptor) alpha | NM 005036 | X 89577 |
| PPAR (peroxisome proliferator-activated receptor) delta | XM 010049 | NM 011144 |
| PPAR (peroxisome proliferator-activated receptor) gamma | NM 015869 | U 01664 |
| Prolactin gene (PRL) | XM 004269 | NM 011164 |
| ProT alpha (prothymosin alpha) | XM 009595 | NM 009378 |
| protein kinase C; | | |
| Purkinje cell protein 2 (Pcp-2) | — | NM 008790 |
| Pyruvate kinase | — | — |
| Rae28/mph1 | — | U 63386 |
| Raf | — | — |
| RAIG-2 | — | — |
| RAIG-3 | — | — |
| RALDH (retinal dehydrogenase II) | — | AF375057 |
| RARP (poly (ADP-ribose) polymerase 1 | XM 010732 | NM 007415 |
| RARP (poly (ADP-ribose) polymerase 2 | NM 005484 | NM 009632 |
| RARP (poly (ADP<_ -ribose) polymer | NM 005485 | — |
| Ras-like GTP-binding protein (Rad) | L 24564 | AF 084466 |
| Rat Ski oncogene | X 15218 | — |
| RB1 (retinoblastoma tumor suppressor gene) | XM 007211 | NM 009029 |
| Relaxin (protein human) | — | — |
| Retinoic acid 4-hydroxylase | — | — |
| rex-1 | — | NM 009556 |
| Rex-1 (Zfp-42) | — | AH 000847 |
| RI-HB, an extracellular heparin binding protein | — | — |
| RIG-E | Z68179 | — |
| Rry/lysyl oxidase | XM 006776 | — |
| RZR (retinoid Z receptor beta) | — | — |
| SF1 | U 76388 | AF 220454 |
| Shh | NM 000193 | X76290 |
| SHP-1, a cytosolic Src homology region 2 domain-containing PTP | — | — |
| SLPI (secretory leukocyte protease) inhibitor | XM 002542 | NM 008275 |
| Slug | XM 011634 | — |
| Snydecan-1 | NM 002690 | NM 011519 |
| SOX9 | BC 007951 | — |
| Sp110 | AF 280095 | — |
| Spermidine/spermine N-1-acetyltransferase | — | — |
| SPR1 (small, proline-rich gene) 1 | XM 004565 | U 66820 |
| Src Suppressed C Kinase Substrate | — | — |
| StAR (steroidogenic acute regulatory gene) | U 17280 | L 36062 |
| STAT 1 | XM 010893 | NM 009283 |
| Stathmin (LAP18) | — | S52658 |
| Stoned B/TFIIA alpha/beta-like factor | XM 042828 | — |
| Stra | — | — |
| Stromelysin 1 | XM 006271 | NM 010809 |
| stromelysin 3 (MMP 11) | XM 037675 | NM 008606 |
| sulfate proteoglycan core protein | | |
| Surfactant B (SP-B) | XM 002565 | — |
| Survivin (SVV) | U 75285 | — |
| T3 receptor (nuclear triiodothyronine receptor) | XM 006394 | NM 010866 |
| TAT (tyrosine aminotransferase) | XM 008081 | — |
| Tau proteins | — | — |
| Tazarotene-induced gene 2 (TIG 2) | NM 002889 | — |
| Tbx 5 | XM 006833 | AF140427 |
| TCF17 (human homologue of the rat zinc finger gene 1) | NM 005649 | NM 009329 |
| Testicular transferrin | XM 039846 | — |
| TGF-beta 3 | — | — |
| Thrombomodulin | — | — |
| thrombomodulin (TM) | XM 009595 | NM 009378 |
| Thy-1 | XM 006076 | NM 009382 |
| Thymosin beta 10 | XM 002498 | — |
| Thymosin beta 4b | — | X16053 |
| Thymposin-beta-10 | XM 002003 | — |
| Thyroid hormone receptor alpha 1 | X 55074 | X 51983 |
| Thyroid hormone receptor TR beta 2 | XM 003822 | NM 009841 |
| TIMP1 | XM 033879 | — |
| TIMP2 | XM 027036 | NM 011594 |
| TIMP3 | XM 009943 | NM 011595 |

APPENDIX 1-continued

VITAMIN D RESPONSE ELEMENT RESPONSIVE GENES AND RETINOIC ACID RESPONSE ELEMENT RESPONSIVE GENES

| | Accession Number Human | Mouse |
|---|---|---|
| TIMP4 | XM 003061 | AF 345865 |
| Tissue factor (TF) | J 02846 | M 57896 |
| Tissue transglutaminase (TGM2) | AF 311286 | AF 114266 |
| Tissue-nonspecific alkaline phosphatase (TNAP) | — | — |
| Tissue-type plasminogen activator (t-PA) | XM 032501 | NM 008872 |
| Tr2-11 (orphan receptor) | M 29960 | Y 11436 |
| TR4(Human TR4 orphan receptor) | L27586 | U32039 |
| Transferrin | XM 002793 | — |
| Transglutaminase-tissue type (TGM2) | AF 311286 | NM 009373 |
| Trk A receptor (NTRK1) | XM 010570 | — |
| Trk B receptor (NTRK2) | NM 006180 | NM 008745 |
| TtT-97 thyroprotes | — | — |
| Type 1 GAP120 | — | — |
| Type II collagen (Col2a1) | XM 038396 | NM 031163 |
| Type II human IMP dehydrogenase | — | — |
| Type X collagen (Col10A1) | NM 000493 | X65121 |
| UAS (upstream activator sequence) | XM 004918 | NM 010453 |
| Unc-33-like phosphoprotein gene (hULip) | Y07818 | X87817 |
| Uncoupling protein 1 (UCP 1) | NM 021833 | NM 009463 |
| Uncoupling protein 3 (UCP3) | U 84763 | AB 010742 |
| Uncoupling protein-2 (UCP2) | — | — |
| Urokinase-type plasmingogen activator (uPA) | D 11143 | NM 008873 |
| Vacht (vesivular Ach transporter) | XM 005733 | NM 021712 |
| vasoactive intestinal peptide receptor 1 (VPAC1) | XM 003226 | NM 011703 |
| VCAM-1 | X 53051 | NM 011693 |
| VCAM-1 (vascular cell adhesion molecule-1) | XM 001500 | NM 011693 |
| Vgr-2 (homology of transforming growth factor-beta superfamily) | — | — |
| Vimentin | XM 042952 | NM 011701 |
| VIP (neuropeptides vasocative intestinal peptide) | XM 004381 | X 74297 |
| VL 30 retrotransposons | ? | ? |
| Wnt 3a | — | X 56842 |
| Wnt-1 | XM 003498 | NM 007423 |
| Wnt-7a | — | M89801 |
| XAG-2 (secreted cement glans protein XAG-2 homolog) | AF 03845 | AF 044262 |
| Xgbx-2 (homeobox gene) | — | — |
| Xgbx-2 (xenopus) | — | — |
| ZAN75 cDNA (codes for a DNA-binding protein) zinc-finger type) high homology to orphan receptor Tr2-11 | — | AB 012725 |

The invention claimed is:

1. A method of treating a hyperproliferative disease of the skin consisting of administering to a patient in need of treatment for a hyperproliferative disease of the skin a pharmaceutical composition consisting of carbenoxolone and one or more pharmaceutically acceptable excipients, wherein the hyperproliferative disease of the skin is selected from the group consisting of psoriasis, acne vulgaris, actinic keratosis, solar keratosis, squamous carcinoma in situ, ichthyoses, hyperkeratosis and Darier's disease.

2. The method of claim 1, wherein said hyperproliferative disease of the skin is selected from the group consisting of psoriasis, acne vulgaris, and hyperkeratosis.

3. The method of claim 1, wherein said hyperproliferative disease of the skin is psoriasis.

4. The method of claim 1, wherein the hyperproliferative disease of the skin is Darier's disease.

5. The method of claim 1, wherein the pharmaceutical composition is administered topically to an affected area of the skin of the patient in need of treatment for a hyperproliferative disease of the skin.

6. The method of claim 5, wherein the hyperproliferative disease of the skin is selected from the group consisting of psoriasis, acne vulgaris, and hyperkeratosis.

7. The method of claim 5, wherein the hyperproliferative disease of the skin is psoriasis.

8. The method of claim 5, wherein the hyperproliferative disease of the skin is Darier's disease.

* * * * *